US012758327B1

(12) United States Patent
Akallal et al.

(10) Patent No.: US 12,758,327 B1
(45) Date of Patent: Oct. 13, 2026

(54) SYSTEM, APPARATUS AND METHODS FOR INTRAOPERATIVE REGISTRATION AND TRACKING

(71) Applicant: SpineCraft, LLC, Westmont, IL (US)

(72) Inventors: Mohammed Akallal, Naperville, IL (US); Wagdy W. Asaad, Burr Ridge, IL (US)

(73) Assignee: SpineCraft, LLC, Westmont, IL (US)

( * ) Notice: Subject to any disclaimer, the term of this patent is extended or adjusted under 35 U.S.C. 154(b) by 0 days.

(21) Appl. No.: 19/236,308

(22) Filed: Jun. 12, 2025

(51) Int. Cl.

| | |
|---|---|
| ***A61B 34/20*** | (2016.01) |
| ***A61B 8/00*** | (2006.01) |
| ***A61B 8/08*** | (2006.01) |
| ***A61B 17/70*** | (2006.01) |
| ***A61B 34/10*** | (2016.01) |
| ***A61B 90/00*** | (2016.01) |
| ***G16H 30/40*** | (2018.01) |

(52) U.S. Cl.
CPC ............ *A61B 34/20* (2016.02); *A61B 8/0875* (2013.01); *A61B 8/5215* (2013.01); *A61B 17/7082* (2013.01); *A61B 34/10* (2016.02); *A61B 90/361* (2016.02); *G16H 30/40* (2018.01); *A61B 2034/102* (2016.02)

(58) Field of Classification Search
CPC ... A61B 34/20; A61B 34/10; A61B 2034/102; A61B 90/361; A61B 8/0875; A61B 8/5215; A61B 17/7082; G16H 30/40
See application file for complete search history.

(56) References Cited

U.S. PATENT DOCUMENTS

| | | | |
|---|---|---|---|
| 5,531,520 | A | 7/1996 | Grimson et al. |
| 5,921,992 | A | 7/1999 | Costales et al. |
| 5,999,840 | A | 12/1999 | Grimson et al. |
| 6,061,644 | A | 5/2000 | Leis |
| D720,851 | S | 1/2015 | Yang et al. |
| 8,933,935 | B2 | 1/2015 | Yang et al. |
| D727,497 | S | 4/2015 | Yang et al. |
| 9,125,624 | B2 | 9/2015 | Dekel et al. |
| D768,296 | S | 10/2016 | Corrao, Jr. et al. |
| 9,513,113 | B2 | 12/2016 | Yang et al. |
| D778,441 | S | 2/2017 | Corrao, Jr. et al. |
| 10,034,713 | B2 | 7/2018 | Yang et al. |
| 10,143,523 | B2 | 12/2018 | Mariampillai et al. |
| 10,799,315 | B2 | 10/2020 | Leung et al. |
| 10,806,525 | B2 | 10/2020 | McGinley et al. |
| 10,973,581 | B2 | 4/2021 | Mariampillai et al. |

(Continued)

FOREIGN PATENT DOCUMENTS

| | | |
|---|---|---|
| CA | 3061807 C | 10/2023 |
| EP | 3820396 | 5/2021 |
| WO | 2020012479 | 1/2020 |

OTHER PUBLICATIONS

Gueziri, HE., Drouin, S., Yan, C.X.B. et al. Toward real-time rigid registration of intra-operative ultrasound with preoperative CT images for lumbar spinal fusion surgery. Int J CARS 14, 1933-1943 (2019). (Year: 2019).*

(Continued)

*Primary Examiner* — Chao Sheng
(74) *Attorney, Agent, or Firm* — Law Office of Alan W. Cannon

(57) ABSTRACT

Systems, apparatus and methods for intraoperative registration and tracking for surgical procedures.

18 Claims, 44 Drawing Sheets

(56) References Cited

U.S. PATENT DOCUMENTS

| | | | | |
|---|---|---|---|---|
| 11,000,335 | B2 | 5/2021 | Dorman | |
| 11,369,436 | B2 | 6/2022 | Kula et al. | |
| 11,464,580 | B2 | 10/2022 | Kemp et al. | |
| 11,483,532 | B2 | 10/2022 | Quiles Casas | |
| 11,547,488 | B2 | 1/2023 | Yang et al. | |
| 11,564,752 | B2 | 1/2023 | Leung et al. | |
| 11,605,185 | B2 | 3/2023 | Mariampillai et al. | |
| 11,712,304 | B2 | 8/2023 | Leung et al. | |
| 11,754,267 | B2 | 9/2023 | Mariampillai et al. | |
| 11,944,390 | B2 | 4/2024 | Mariampillai et al. | |
| 11,950,852 | B2 | 4/2024 | Leung et al. | |
| 12,029,527 | B2 | 7/2024 | Mak et al. | |
| 12,137,985 | B2 | 11/2024 | Yang et al. | |
| 2018/0049622 | A1 | 2/2018 | Ryan et al. | |
| 2018/0279913 | A1 | 10/2018 | Frasier et al. | |
| 2018/0338799 | A1 | 11/2018 | Hladio et al. | |
| 2019/0090955 | A1 | 3/2019 | Singh et al. | |
| 2019/0321108 | A1 | 10/2019 | Ghanam et al. | |
| 2020/0197100 | A1* | 6/2020 | Leung | A61B 34/25 |
| 2020/0273169 | A1 | 8/2020 | Mauldin et al. | |
| 2021/0030479 | A1 | 2/2021 | Marti et al. | |
| 2021/0236212 | A1 | 8/2021 | Ghanam et al. | |
| 2022/0092800 | A1* | 3/2022 | Toporek | A61B 6/4266 |
| 2022/0156966 | A1 | 5/2022 | Chen et al. | |
| 2022/0202507 | A1 | 6/2022 | Siegler et al. | |
| 2022/0361955 | A1 | 11/2022 | Signoretti et al. | |
| 2022/0387129 | A1 | 12/2022 | Kinrot | |
| 2023/0041207 | A1 | 2/2023 | Bhandari | |
| 2023/0149096 | A1 | 5/2023 | Mariampillai | |
| 2024/0130797 | A1 | 4/2024 | Boddington et al. | |
| 2024/0265667 | A1 | 8/2024 | Luciano et al. | |

OTHER PUBLICATIONS

Alatise et al., "Pose Estimation of a Mobile Robot Based on Fusion of IMU Data and Vision Data Using an Extended Kalman Filter", Sensors 2017, 17, 2164; doi:10.3390/s17102164, pp. 1-22.

Eirik et al., "Registration of MR Images to Ultrasound Images of the Spine", SINTEF Technology and Society, Trondheim, Norway; Norwegian University of Science and Technology, Trondheim, Norway; The Central Norway Regional Health Authority, Trondheim, Norway; The Intervention Centre, Oslo University Hospital, Oslo, Norway; May 19, 2014; pp. 1-11.

Fu et al., "The Future of Endoscopic Navigation: A Review of Advanced Endoscopic Vision Technology", IEEE Access, vol. 9, 2021, Mar. 10, 2021, pp. 41144-41167.

Garrido-Jurado et al., "Automatic generation and detection of highly reliable fiducial markers under occlusion", Pattern Recognition 47 (2014) 2280-2292.

He at al., "An Inertial and Optical Sensor Fusion Approach for Six Degree-of-Freedom Pose Estimation", Sensors 2015, 15, 16448-16465.

Hinterstoisser et al., "Model Based Training, Detection and Pose Estimation of Texture-Less 3D Objects in Heavily Cluttered Scenes", 2013; Computer Vision—ACCV 2012. ACCV 2012. Lecture Notes in Computer Science, vol. 7724. Springer, Berlin, Heidelberg. https://doi.org/10.1007/978-3-642-37331-2_42.

Hoff, "Fusion of Data from Head-Mounted and Fixed Sensors", Submitted to the First International Workshop on Augmented Reality, Nov. 1, 1998, San Francisco, California; pp. 1-20.

Newcombe et al., "KinectFusion: Real-Time Dense Surface Mapping and Tracking", 2011 10th IEEE International Symposium on Mixed and Augmented Reality, Oct. 26-29, 2011, 10 pages.

Oh et al., "Pose estimation of surgical instrument using sensor data fusion with optical tracker and IMU based on Kalman filter", MATEC Web of Conferences, 32, 04008 (2015), pp. 1-5.

Okamura, "Lecture 4: Cooperative manipulation", Stanford University, ME 328: Medical Robotics Winter 2019, pp. 1-16.

Okamura, "Lecture 2: Kinematics of medical robotics", Stanford University, ME 328: Medical Robotics Winter 2019, pp. 1-25.

Okamura, "Lecture 6: Medical imaging and image-guided interventions", Stanford University, ME 328: Medical Robotics Winter 2019, pp. 1-38.

Okamura, "Lecture 10: Port placement in robot-assisted minimally invasive surgery", Stanford University, ME 328: Medical Robotics Winter 2019, pp. 1-26.

Okamura, "Lecture 8: Registration", Stanford University, ME 328: Medical Robotics Winter 2019, pp. 1-31.

Okamura, "Lecture 5: Robot dynamics and simulation", Stanford University, ME 328: Medical Robotics Winter 2019, pp. 1-39.

Okamura, "Lecture 7: Tracking for surgical navigation", Stanford University, ME 328: Medical Robotics Winter 2019, pp. 1-13.

Peng et al., "Robust Tightly Coupled Pose Measurement Based on Multi-Sensor Fusion in Mobile Robot System", Sensors 2021, 21, 5522, pp. 1-19.

Ren et al., "Multisensor Data Fusion in an Integrated Tracking System for Endoscopic Surgery", IEEE Transactions On Information Technology in Biomedicine, vol. 16, No. 1, Jan. 2012, pp. 106-111.

West et al., "Designing Optically Tracked Instruments for Image-Guided Surgery", IEEE Transactions On Medical Imaging, vol. 23, No. 5, May 2004, pp. 533-545.

* cited by examiner

SYSTEM, APPARATUS AND METHODS FOR INTRAOPERATIVE REGISTRATION AND TRACKING

FIELD OF THE INVENTION

The present invention relates to the field of orthopedic surgery, in particular to devices and methods for registration, tracking and patient-specific 3D surgical planning and procedures. Specific applications to spine surgery and minimally-invasive surgery are provided.

BACKGROUND OF THE INVENTION

Image-guided target tracking and surgical guidance can be used to locate a specific target within three-dimensional (3D) space. These techniques can be used in medical procedures to locate an object in the human body, such as the spine, brain or other organ structures, during surgery.

One technique for tracking and surgical guidance uses fiducial markers that are attached to the body with a clamp, an adhesive, or through other means. Generally, these fiducial markers are aligned to a 3D representation of the body, which may be acquired by different imaging modalities. This 3D representation, usually acquired before surgery, may include a specific region, such as a vertebral column, to a scan of the entire body. Within this 3D representation, areas of interest are located and matched to the fiducial markers in the real surgical space. This results in a coordinate system transform that maps the relative position of the region of interest to the location of the fiducial markers to provide visual feedback to the clinician during surgery. The surgeon can then use this information to facilitate guidance to a specific location in the body that is related to the region of interest in the image.

Optical-based surgical navigation has been used to guide spinal surgeries and for placement of screws in the spine. These systems are typically based on two cameras that detect light that is either emitted (mounted with LEDs), or passively reflected from surgical tools and probes. Using the signal detected by the cameras combined with the knowledge of the dimensions of the navigation probes, a computer workstation is able to precisely determine where the tip of the surgical instrument lies. However, these techniques require the tool or probe being tracked to be constantly held in an orientation that keeps the active or passive indicators in the direction of the camera(s) in direct line of sight in order to maintain the inputted visual data that is used to determine where the tip of the tool or probe lies. Also, while these techniques allow for the tip position to be tracked, they typically do not provide the capability for tracking the rotation position about the Z-axis (yaw) of the instrument or probe for full directional tracking.

SUMMARY OF THE INVENTION

According to one aspect of the present invention, a method of tracking and registration for a spine surgery includes: providing volumetric image data obtained from a preoperative scan of at least a portion of a spine including preselected vertebrae of the spine; processing the volumetric image data, including extracting surface data characterizing bone surfaces of the preselected vertebrae; extracting partial surface data that can be captured by ultrasound from the extracted surface data characterizing boned surfaces of the preselected vertebrae; sweeping, from locations external of a body in which the spine is located, at least the preselected vertebrae and processing data obtained therefrom to provide ultrasound volumetric image data; correlating the ultrasound volumetric image data and the extracted partial surface data and identifying ultrasound surface data characterizing the bone surfaces of the preselected vertebrae that correspond to the surface data extracted from the volumetric image data from the preoperative scan and coarsely registering the identified ultrasound surface data with the surface data extracted from the volumetric image data for each vertebra of the preselected vertebrae by calculating rotation matrices and translation vectors that transform the surface data extracted from the volumetric image data to correlate with the ultrasound volumetric data; making a least one incision to provide access to the preselected vertebrae; obtaining post-incision image data for each of the preselected vertebrae; for each of the preselected vertebrae, performing a registration refinement comprising processing the post-incision image data obtained after incision, calculating refinement of the rotation matrices and translation vectors, based on the post-incision image data obtained; applying the rotation matrices and translation vectors and generating and displaying at least one model of an instrument, screw or device overlaid on an image generated from the volumetric image data obtained from the preoperative scan.

In at least one embodiment, the registration refinement includes: inserting an ultrasound probe through one or more incisions on left and right sides of the preselected vertebrae to capture local ultrasound volumetric image data; tracking the ultrasound probe during the capture process; extracting local surface data characterizing bone surfaces corresponding to the bone surfaces of the local ultrasound volumetric data from the volumetric image data; and for each of the preselected vertebrae, refining the registering of the ultrasound surface data with the surface data by calculating refinement of the rotation matrices and translation vectors, based on the local surface data extracted; wherein image resolution of the local ultrasound volumetric image data is higher than image resolution of the ultrasound volumetric image data.

In at least one embodiment, the spine surgery is an MIS surgical procedure.

In at least one embodiment, the registration refinement includes: obtaining the post-incision image data by imaging exposed bony structures of the preselected vertebrae via a camera system; and wherein the registration refinement includes matching a 3D surface of the post-incision imaging data of exposed bony structures to the surface data characterizing bone surfaces of the preselected vertebrae extracted from the volumetric image data.

In at least one embodiment, for each of the preselected vertebrae, the post-incision image data comprises a 3D point cloud.

In at least one embodiment, the spine surgery is an open surgical procedure.

In at least one embodiment, the volumetric image data obtained from the preoperative scan is provided from a CT preoperative scan.

In at least one embodiment, applying the refinement rotation matrices and refinement translation vectors and generating and displaying includes displaying a 3D image of at least the preselected vertebrae, the method further including: installing navigation caps having directional navigation modules on pedicle screws; for each of the pedicle screws, inserting a screw driving instrument through a bore of the navigation cap installed on the pedicle screw, and driving the pedicle screw into one of the preselected vertebrae; calculating positions and orientations of the pedicle screws installed in the preselected vertebrae, based on inputs received from image data of the navigation caps and data received from the directional navigation modules, respectively; calculating a rod length, rod bends in a coronal plan at each location of each of the pedicle screws and reduction needed at each of the pedicle screws, based on the calculated positions and orientations of the pedicle screws to create a rod bending template; and outputting the rod bending template for use in making a custom bent rod.

In at least one embodiment, the method further includes: overlaying a model of a rod bent according to specifications of the rod bending template, a rod inserter and the pedicle screws on an image of the selected vertebrae generated from the volumetric image data obtained from the preoperative scan; and advancing the rod while tracking advancement of the rod by the rod inserter through heads of the pedicle screws via the overlaid models of pedicle screws and the rod.

In at least one embodiment, the method includes confirming, by viewing on the display, whether reductions to be accomplished at each of the pedicle screws are within predefined acceptance levels, and when one or more of the reductions is not within the predefined acceptance level, for each of the pedicle screws where reduction is not within the predefined acceptance level, introducing a screw driver through the bore of the navigation cap, adjusting the pedicle screw insertion level, viewing the screw having been adjusted and the resultant reduction having been achieved, and repeating the adjusting and viewing as needed, until reductions accomplished by each of the pedicle screws are within the predefined acceptance levels.

In at least one embodiment, the sweeping from locations external of the body is performed using an ultrasound probe tracked at least in part by using a directional navigation module integral therewith or attached thereto.

In at least one embodiment, the method further includes manually bending a rod according to specifications of the rod bending template having been outputted.

In at least one embodiment, the rod bending template is outputted to a rod bending machine, and the method further comprises automatically bending a rod according to specifications of the rod bending template.

In at least one embodiment, ultrasound sweep acceptance criteria is checked as the sweeping is performed and size, coverage, and percentage of bright points of the ultrasound volumetric image data are calculated.

In at least one embodiment, the sweeping is performed manually.

In at least one embodiment, the sweeping is performed by a robotic arm.

In at least one embodiment, a rod bent by the manual bending method is provided.

In at least one embodiment, a rod bent by the automatic bending method is provided.

According to another aspect of the present invention a system for tracking and registration during a spine surgery is provided that includes: an ultrasound imaging system; a directional navigation module integral with or mountable to at least one element of the ultrasound imaging system; a camera system configured to perform imaging; and computer hardware operatively coupled to the ultrasound imaging system and the camera system, wherein the computer hardware comprises memory coupled with one or more processors to store instructions, which when executed by the one or more processors, causes the one or more processors to perform operations comprising: processing volumetric image data obtained from a preoperative scan of at least a portion of the spine including preselected vertebrae of the spine to include extracting surface data characterizing bone surfaces of the preselected vertebrae from the volumetric image data; processing ultrasound volume (USV) image data obtained prior to incision, by sweeping at least the preselected vertebrae with the element of the ultrasound imaging system as it is tracked, facilitated by the directional navigation module; identifying partial surface data characterizing the bone surfaces of the preselected vertebrae that can be captured by ultrasound and correspond to the surface data extracted from the volumetric image data from the preoperative scan; for each of the preselected vertebrae, performing a coarse registration comprising registering the partial surface data with the ultrasound volume (USV) image data by calculating rotation matrices and translation vectors that transform the partial surface data to correlate with the ultrasound volume (USV) image; for each of the preselected vertebrae, performing a registration refinement comprising processing post-incision image data obtained after incision, calculating refinement of the rotation matrices and translation vectors, based on the post-incision image data obtained; applying the rotation matrices and translation vectors to generate and display at least one model of an instrument, screw or device overlaid on an image generated from the volumetric image data obtained from the preoperative scan.

In at least one embodiment, the element of the ultrasound imaging system comprises a first element, the ultrasound imaging system further comprising a second element comprising the directional navigation module mountable to the second element, or a second directional navigation module mountable to, or integral with the second element, wherein the second element comprises a probe configured to be inserted through one or more incisions on left and right sides of the preselected vertebrae to capture local ultrasound volumetric image data as the second element is tracked using the directional navigation module or second directional navigation module, wherein the post-incision image data comprises the ultrasound volumetric image data; and the performing a registration refinement comprises the one or more processors performing operations comprising: extracting local surface data characterizing bone surfaces corresponding to the bone surfaces of the local ultrasound volumetric data from the volumetric image data; for each of the preselected vertebrae, refining the registering of the ultrasound surface data with the surface data by calculating refinement of the rotation matrices and translation vectors, based on the local surface data obtained; wherein image resolution obtained using the second element is higher than image resolution obtained using the first element.

In at least one embodiment, the spine surgery is an MIS surgical procedure.

In at least one embodiment, the post-incision image data obtained comprises imaging data of exposed bony structures of the preselected vertebrae obtained by the camera system; and wherein the registration refinement comprises matching a 3D surface of the imaging data of exposed bony structures to the surface data characterizing bone surfaces of the preselected vertebrae extracted from the volumetric image data.

In at least one embodiment, for each of the preselected vertebrae, the post-incision image data comprises a 3D point cloud.

In at least one embodiment, the spine surgery is an open surgical procedure.

In at least one embodiment, the system further includes: a plurality of navigation caps configured to be mounted to a plurality of pedicle screws, respectively, each of the navigation caps provided with another of the directional navigation modules integral therewith or mounted thereto and a bore passing therethrough coaxially a longitudinal axis of the navigation cap; and a screw driving instrument configured to be inserted through the bore to engage with the respective pedicle screw; wherein the instructions when executed by the one or more processors, causes the one or more processors to further perform operations comprising: calculating positions and orientations of the pedicle screws during installation in the preselected vertebrae via driving by the screw driving instrument, based on inputs received from image data of the navigation caps having been installed on the pedicle screws and data received from the directional navigation modules for each of the navigation caps, respectively; calculating a rod length, rod bends in a coronal plane at each the pedicle screw and an amount of reduction needed at each of the pedicle screws, based on image data received from the camera system and the calculated positions and orientations of the pedicle screws to create a rod bending template; and outputting the rod bending template for use in making a custom bent rod.

In at least one embodiment, the instructions when executed by the one or more processors, causes the one or more processors to further perform operations comprising: overlaying a model of a rod bent according to specifications of the rod bending template and a rod inserter on an image generated from the volumetric image data obtained from the preoperative scan.

In at least one embodiment, the instructions when executed by the one or more processors, causes the one or more processors to further perform operations comprising: after securement of at least one rod to multiple vertebral levels with pedicle screws, confirming and displaying whether reductions accomplished by each of the pedicle screws are within predefined acceptance levels.

In at least one embodiment, upon viewing, wherein, when the reductions accomplished by at least one of the pedicle screws is/are not within the predefined acceptance levels, the system is configured so that the screw driving instrument can adjust the at least one of the pedicle screws, while continuing the calculating positions and orientations, as the navigation caps remain fixed to the pedicle screws.

In at least one embodiment, the navigation caps are configured to remain fixed to the pedicle screws during navigation of the rods and attachment of the rods to the pedicle screws.

In at least one embodiment, the directional navigation module integral with or mountable to the at least one element of the ultrasound imaging system comprises: a shell configured to continuously circumscribe a longitudinal axis of the at least one element; retroreflective disks or pattern-based markers on external faces of the shell, configured and positioned to be visualized by the camera system; and an inertial measurement unit mounted inside of the shell; wherein the one or more processors perform operations comprising: receiving image data of the retroreflective disks or pattern-based markers from the camera system; receiving data from the inertial measurement unit; and calculating orientation and tip direction and location of the element using a deep learning algorithm and fusion algorithm or by using a fusion algorithm to fuse the image data and the data from the inertial measurement unit.

In at least one embodiment, the shell comprises a cross-sectional shape that is pentagonal, hexagonal or octagonal.

In at least one embodiment, the inertial measurement unit comprises at least 9 degrees of freedom.

In at least one embodiment, the inertial measurement unit comprises 10 degrees of freedom.

In at least one embodiment, a shape of the shell is a prism, frustum or double-sided frustum.

In at least one embodiment, each face of the shell comprises at least one of the retroreflective disks or pattern-based markers thereon.

In at least one embodiment, at least one of a top and bottom of the shell has at least one of the retroreflective disks or pattern-based markers thereon.

In at least one embodiment, the pattern-based markers are on the external faces of the shell, and wherein the pattern-based markers comprise concentric or eccentric squares, concentric or eccentric rectangles, concentric or eccentric circles, concentric or eccentric ellipses, or a regular polygon with an alternating pattern of black and white.

In at least one embodiment, the alternating pattern comprises at least three of the patterns, the patterns having constant thicknesses or decreasing thicknesses from innermost to outermost of the patterns, with the thicknesses decrease according to a predefined ratio.

In at least one embodiment, a direction and/or a norm of a vector starting from a center of an outermost of the patterns to a center of an innermost of the patterns of each of the pattern-based markers is different from the direction and/or the norm of each of the other of the pattern-based markers on each the face of the shell.

In at least one embodiment, centers of outermost shapes of the retroreflective disks or pattern-based markers are equidistant to orthogonal projections of the outermost shapes on the longitudinal axis and equidistant to a distal tip of the at least one instrument.

In at least one embodiment, centers of outermost shapes of the retroreflective disks or pattern-based markers on the at least one of a top and bottom of the shell are equidistant to the longitudinal axis and equidistant to a distal tip of the at least one instrument.

In at least one embodiment, the at least one element comprises a shaft extending along the longitudinal axis and a key feature on the shaft at at least one predetermined radial position about a cross-section of the shaft; the shell comprising a mating key feature that fits with the key feature to fix the shell in a predefined orientation rotationally with respect to the shaft.

In at least one embodiment, the inertial measurement unit is mounted in the shell so that one axis of an X-Y-Z three dimensional axis reference of the inertial measurement unit is parallel to the longitudinal axis when the directional navigation module is integral with or mounted to the at least one element.

In at least one embodiment, a Z axis of the inertial measurement unit is parallel to the longitudinal axis when the directional navigation module is integral with or mounted to the at least one element.

In at least one embodiment, the inertial measurement unit communicates with the one or more processors wirelessly.

In at least one embodiment, the inertial measurement unit communicates with the one or more processors via BLUETOOTH BLE®.

In at least one embodiment, the one or more processors track tip edge orientation of the at least one element, using image data received from the camera system and data received from the inertial measurement unit.

In at least one embodiment, the one or more processors use known geometric relationships of eccentric or concentric shapes of each of the retroreflective disks or pattern-based markers on the faces and known geometric relationships between the retroreflective disks or pattern-based markers on the faces, and/or known geometric relationships of eccentric or concentric shapes of the retroreflective disks or pattern-based markers on the at least one of a top and bottom, and/or known geometric relationships between the retroreflective disks or pattern-based markers on the at least one of a top and bottom, that are in a line of detection by the camera system, in conjunction with data received from the inertial measurement unit using a deep learning algorithm and fusion algorithm to identify and track orientation and the location of the at least one element.

In at least one embodiment, the at least one element is an ultrasound transducer and the directional navigational module aligns a plane of capture of the transducer with an axis of symmetry defined by the key feature to enable pose estimation and ultrasound volume construction by the processing ultrasound volumetric image data.

In at least one embodiment, the directional navigation modules integrally provided with the navigation caps or mounted to the navigation caps each comprise a marker and an inertial measurement unit wherein the directional navigation modules are provided integrally or mounted at proximal end portions of the navigation caps, and distal end portions of the navigation caps are configured to mate with heads of respective ones of the pedicle screws.

According to another aspect of the present invention, a directional navigation module is provided, including: a shell configured to continuously circumscribe a longitudinal axis of at least one element that the directional navigation model is configured to be attached to or integrated with; retroreflective disks or pattern-based markers on external surfaces of the shell, configured and positioned to be detected by a camera system; and an inertial measurement unit mounted inside of the shell and configured to provide real-time directional position information for a tip of the at least one element.

In at least one embodiment, the shell comprises a cross-sectional shape that is pentagonal, hexagonal or octagonal.

In at least one embodiment, the inertial measurement unit comprises at least nine degrees of freedom.

In at least one embodiment, the inertial measurement unit comprises ten degrees of freedom.

In at least one embodiment, a shape of the shell is a prism, frustum or double-sided frustum.

In at least one embodiment, the external surfaces comprise faces and wherein each of the faces comprises at least one of the retroreflective disks or pattern-based markers thereon.

In at least one embodiment, at least one of a top and bottom of the shell has at least one of the retroreflective disks or pattern-based markers thereon.

In at least one embodiment, the pattern-based markers are on the external surfaces of the shell, and wherein the pattern-based markers comprise concentric or eccentric squares, concentric or eccentric rectangles, concentric or eccentric circles, concentric or eccentric ellipses, or a regular polygon with an alternating pattern of black and white.

In at least one embodiment, the alternating pattern comprises at least three of the patterns, the patterns having constant thicknesses or decreasing thicknesses from innermost to outermost of the patterns, with the thicknesses decreasing according to a predefined ratio.

In at least one embodiment, a direction and/or a norm of a vector starting from a center of an outermost pattern of one of the pattern-based markers to a center of an innermost pattern of the one of the pattern-based markers is different from a direction and/or norm of a vector of any other one of the pattern-based markers.

In at least one embodiment, centers of the retroreflective disks or pattern-based markers are equidistant to their orthogonal projections on the longitudinal axis and equidistant to a distal tip of the at least one element.

In at least one embodiment, centers of the retroreflective disks or pattern-based markers on the at least one of a top and bottom of the shell are equidistant to the longitudinal axis and equidistant to a distal tip of the at least one element.

In at least one embodiment, the at least one element comprises a shaft extending along the longitudinal axis and a key feature on the shaft at at least one predetermined radial position about a cross-section of the shaft; the shell comprising a mating key feature that fits with the key feature to fix the shell in a predefined orientation rotationally with respect to the shaft.

In at least one embodiment, the inertial measurement unit is mounted in the shell so that one axis of an X-Y-Z three dimensional axis reference of the inertial measurement unit is parallel to the longitudinal axis when the directional navigation module is integral with or mounted to the at least one element.

In at least one embodiment, a Z axis of the inertial measurement unit is parallel to the longitudinal axis when the directional navigation module is integral with or mounted to the at least one element.

In at least one embodiment, the inertial measurement unit is configured to communicate wirelessly with one or more processors.

In at least one embodiment, the inertial measurement unit communicates with the one or more processors via BLUETOOTH BLE®.

In at least one embodiment, the inertial measurement unit comprises a fusion sensor and the real-time directional position information is configured to be fused with image data from a camera system.

According to another aspect of the present invention, a navigation cap is provided that includes: a directional navigation module as described above; a connector at a distal end portion of the directional navigation module, the connector configured to attach to a pedicle screw or tabs extending proximally from a pedicle screw; and a bore passing through the directional navigation module, coaxial with a longitudinal axis of the navigation cap.

In at least one embodiment, the connector comprises a collar.

In at least one embodiment, the connector is cylindrical with threads provided on at least a distal end portion thereof.

In at least one embodiment, when the navigation cap is attached to the tabs or pedicle screw, the navigation cap is configured to be scanned with a camera system, and rod length and reduction needed in regard to the screw is configured to be calculated using a deep learning algorithm and a fusion algorithm of a navigation software on data received from the camera system and data received from the inertial measurement unit.

In at least one embodiment, the at least one element is an ultrasound probe and the directional navigation model is attached to or integrated with the ultrasound probe.

In at least one embodiment, the at least one element comprises a surgical instrument and the directional navigation model is attached to or integrated with the surgical instrument.

These and other advantages and features of the invention will become apparent to those persons skilled in the art upon reading the details of the embodiments as more fully described below.

BRIEF DESCRIPTION OF THE DRAWINGS

In the course of the detailed description to follow, reference will be made to the attached drawings. These drawings show different aspects of the present invention an, where appropriate, reference numerals illustrating like structures, components, materials and/or elements in different figures are labeled similarly. It is understood that various combinations of the structures, components, materials and/or elements, other than those specifically shown, are contemplated and are within the scope of the present invention.

DETAILED DESCRIPTION OF THE INVENTION

Figure 1A:
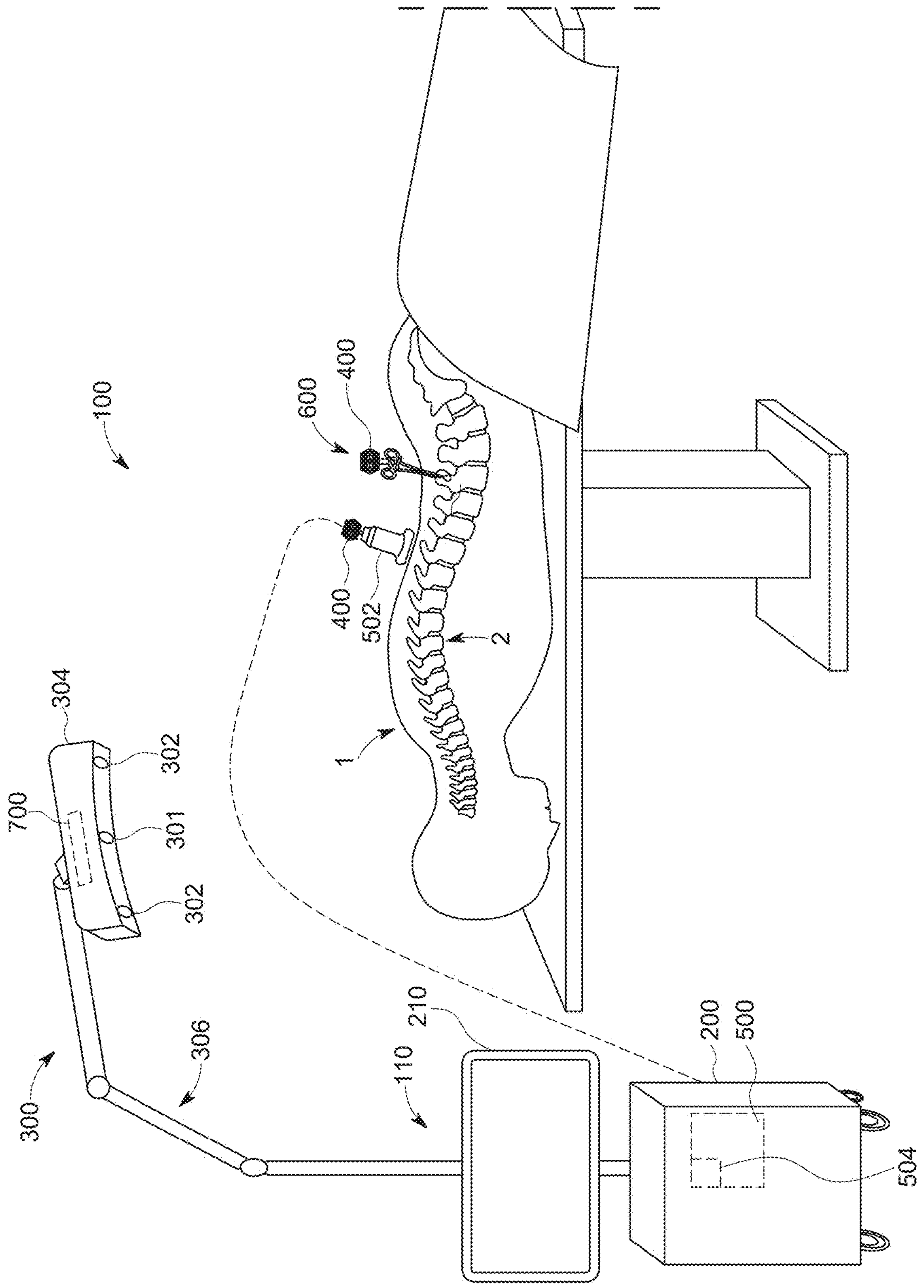
FIGS. 1A-1B illustrate a surgical operating room equipped with variations of a system for tracking and registration, according to an embodiment of the present invention.

Before the present embodiments are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a marker" includes a plurality of such markers and reference to "the screw" includes reference to one or more screws and equivalents thereof known to those skilled in the art, and so forth.

The publications discussed herein are provided solely for their disclosure prior to the filing date of the present application. The dates of publication provided may be different from the actual publication dates which may need to be independently confirmed.

Definitions

A "fiducial marker" or "fiducial" as used herein, refers to a light emitting or retroreflective element such as a light emitting diode, infrared-emitting diode, retroreflective spheres, disks or pattern markers that can be used by an optical system for calculation of localization information of an instrument or probe to which the fiducial or fiducials are attached.

"Fiducial localization error" (FLE), as used herein, refers to the distance between the true position of a fiducial and its measured position, i.e., the error of localizing the fiducial. In the case of optically tracked instruments, FLE is the error the optical tracking system makes when it measures the position of a fiducial marker attached to the surgical instrument in the physical space coordinate system of the optical position sensor (OPS) that is measuring the position of the fiducial marker.

"Fiducial registration error" (FRE), as used herein, refers to the distance between corresponding fiducial points after registration. In the case of optically tracked instruments, the tracking system aligns the measured positions of the fiducial markers attached to the surgical instrument in the physical space coordinate system of the OPS with the known (calibrated) positions of the fiducial markers in the instrument coordinate system. FRE is the residual distance between corresponding fiducial positions after this alignment.

"Target registration error" (TRE), as used herein, refers to the distance between corresponding points other than the fiducial points after registration. In the case of optically tracked instruments, the tracking system uses the transformation obtained by aligning the measured and known (calibrated) fiducial marker positions to map the instrument tip position from the instrument coordinate system to the physical space coordinate system of the OPS. TRE, which is the error of this mapping, is the tip position tracking error.

"Intraoperative", as used herein, refers to an action, process, method, event or step that occurs or is carried out during at least a portion of a medical procedure.

"Preoperative", as used herein, refers to an action, process, method, event or step that occurs or is carried out before the medical procedure begins.

The acronym "MIS", as used herein, refers to "minimally invasive spine surgery" and is an acronym that is commonly used in the art. MIS uses smaller incisions than procedures that are typically referred to as "open" spine surgical procedures, and uses specialized tools to treat spinal conditions while minimizing tissue damage and potentially leading to faster recovery and less pain compared to traditional open surgery.

The term "ResNet18 Backbone" as used herein, refers to a well-known deep learning subnetwork used for high level feature extraction trained on ImageNet Dataset. "ImageNet" is an ongoing research effort to provide researchers around the world with image data for training large-scale object recognition models.

The acronym "CNN", as used herein, refers to a convolutional neural network, which is a known type of artificial neural network that uses raw pixel data to process images and videos, and recognize objects. CNNs are a subset of machine learning and a core component of deep learning algorithms. CNN may be used to learn features via filter optimization.

The acronym "MLP", as used herein, refers to a "multilayer perceptron", which is name for a known modern feedforward neural network consisting of fully connected neurons with nonlinear activation functions.

The acronym "PnP", as used herein, refers to "Perspective-n-Point", which is a known problem of estimating the pose of a calibrated camera given a set of n 3D points in the world and their corresponding 2D projections in the image.

FIG. 1 illustrates a surgical operating room equipped with a system for tracking and registration 100, which a healthcare worker (or team) such as a surgeon (or surgeons and team) (not shown), can employ to facilitate operating on a patient 1, in accordance with an embodiment of the present invention. An equipment stand 110 supports a computing system 200, which may include, but is not limited to a desktop computer, laptop computer and/or other computing devices equipped with navigation software and one or more displays 210 for displaying visualizations of the patient 1 both preoperatively, if desired, and intraoperatively.

System 100 is further provided with an optical camera system 300 configured to take images of (image) the patient 1 and, more specifically, directional navigation modules 400 for use in optically tracking locations on the patient 1 and/or specific locations of elements, which directional navigation modules are attached to or integral with. Camera system 300 is provided with a pair of cameras 302 (stereo camera configuration), but may alternatively be provided with only one camera 302 or more than two cameras, typically up to about four cameras. Cameras 302 are mounted on or in a head 304, which is supported by an articulated arm 306 that allows for repositioning the camera head 304 as needed. Optionally, one or more light sources 301 can be mounted on or in head 304 to provide additional lighting to assist image reception by cameras 302. Articulated arm 306 may be mounted to the equipment stand 110 or may be provided with a standalone support (not shown). Camera system 300 also includes an embedded inertial measurement unit 700.

Figure 1B:
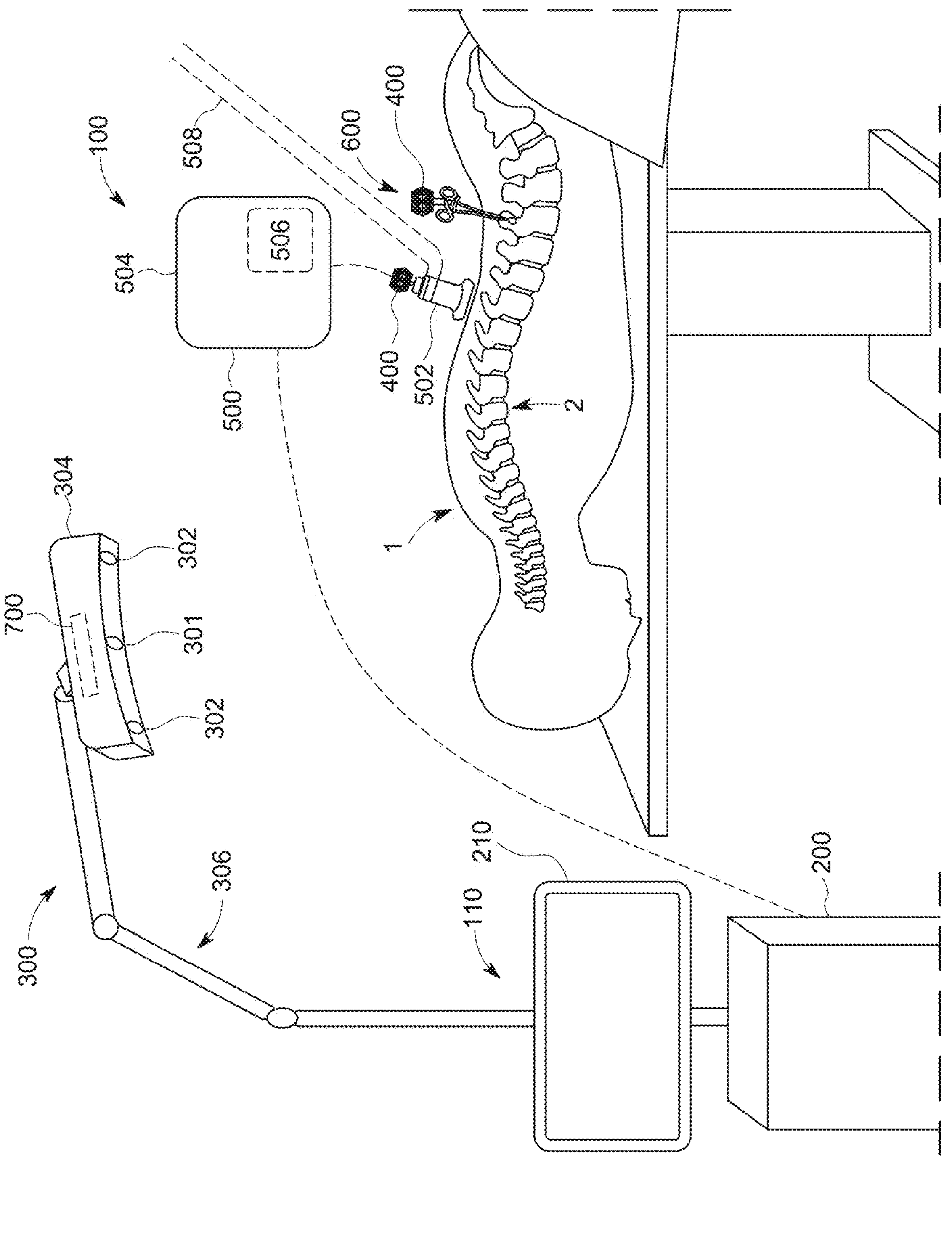

An ultrasound imaging system 500 is further provided for generating ultrasound images of the patient 1. The system 500 is preferably integrated in the computing system 200 as shown in FIG. 1A and the transducer 502 in this case is connected with wire or wirelessly directly to system 200. Alternatively, the ultrasound imaging system 500 may be standalone, as illustrated in FIG. 1B, wherein the transducer is connected with wire or wirelessly to ultrasound imaging system 500 and ultrasound imaging system 500 is connected with wire or wirelessly to computing system 200. In either case, ultrasound image data from ultrasound imaging system 500 or 200 (where computing system 200 and navigation software function as the ultrasound system 500 as in FIG. 1A) are compiled together to form ultrasound volume using the tracking system 100. Thus, in the variant of FIG. 1A, the transducer 502 is connected directly, by wire or wirelessly, to a card installed in the computer system 200. A software Application Programming Interface (API) provided by the transducer manufacturer is integrated into the navigation software to extract and use ultrasound images. In the variation of FIG. 1B, the transducer 502 is connected by wire or wirelessly to an external ultrasound system 500 that communicates with the computer system 200 and the navigation software More details of processing are described below. As shown in FIG. 1A-1B, an instrument for scanning with ultrasound waves (ultrasound transducer) 502 can be swept over a target to be imaged (at least a portion of the spine 1 as illustrated in FIGS. 1A-1B). Transducer element 502 is provided with a directional navigation module (DNM) 400 that can be either integrated with element 502 or mounted thereto, at a proximal end portion in both instances. The transducer 502 may be connected to ultrasound computer/generator 504 which sends instructions to the transducer 502 to generate ultrasound that is applied to the patient and receives data from transducer 502 that is produced from reflections of ultrasound waves from structures in the patient, according to known practice. System 500 may optionally be provided with a display 506 to display ultrasound images processed by computer/generator 504, and/or images may be displayed on 210. Ultrasound imaging system 500 is connected to computing system 200 (either wired or wirelessly, preferably wired) or can be part of the computing system 200. The images captured by the transducer 502 are 2D. The tracking of the transducer 502 provides the location in the 3D space of each 2D capture, which in turn allows forming an ultrasound 3D volume from the sweep. The camera system 300 and the DNM 400 are used to track the transducer 502.

The transducer 502 may be manually operated to perform a sweep, with visual feedback provided at either display 506 or 210. Alternatively, transducer 502 may be attached to or integrally provided with a robotic arm 508 that can be controlled via programming provided in computing system 200.

In addition to the ultrasound imaging data, the DNM 400 that is attached to or integrated with element 502 tracks the position and orientation of the transducer element 502 relative to the patient 1, in this case, specifically relative to the features of the patient's spine. This position and tracking data are tagged to the ultrasound image data so that the ultrasound images produced can be properly located and oriented relative to the patient's spine. The position and tracking data can be sent to the computing system 200 by wire or wirelessly. In at least one embodiment, the position and tracking data are provided by the camera system 300 which is connected to the computer system 200 by wire, and the data from the IMU 700 of the DNM 400 are transmitted wirelessly to the computer system 200. More details regarding the functionality of DNM 400 are provided below.

An instrument such as a clamp or the like is placed temporarily to function as a reference frame 600. The reference frame 600 may be attached to a spinous process close to the levels to be instrumented or in some cases may be inserted percutaneously and attached to the posterior superior iliac. The reference frame 600 with the DNM 400 represents a coordinate system attached to the patient 1. The tracking and the navigation are based on finding the transformations between the coordinate system of the camera system 300, the coordinate system of DNM 400 instrument, and the coordinate system of the reference frame 600.

A DNM 400 can be integrated with the reference frame instrument 600, or mounted thereto, as in the case shown in FIGS. 1A-1B. Camera system scanning of the DNM 400 on reference frame 600 provides a reference against which all other measurements of camera scanning results can be measured, since the location and orientation of the spine becomes known once the registration is completed at the location and orientation where the reference frame 600 is attached. Likewise, the orientation and position information transmitted by the DNM 400 of the reference frame 600 to computing system 200 provides a reference against which all other measurements of ultrasound scanning (as measured by DNM 400 connected to transducer 502) can be measured. Similarly, the reference frame provides reference orientation and position information against which data provided from DNMs 400 that may be attached to other instruments and/or apparatus can be measured. Also, other tools and instruments may be manually operated or attached one or more other robotic arms for programmed operation thereof. In either case, such tools and instruments can be provided with DNM's 400 for tracking and navigation thereof, as described herein.

Registration and navigation procedures are carried out using one or more preoperative images of the target site, against which to perform registration. Such preoperative images are typically performed by computed tomography (CT) scan for purposes of spinal surgery procedures, but could be provided by an alternative form of preoperative imaging, including, but not limited to MRI, 3D X-Ray, CBCT or the like.

Figure 2A:
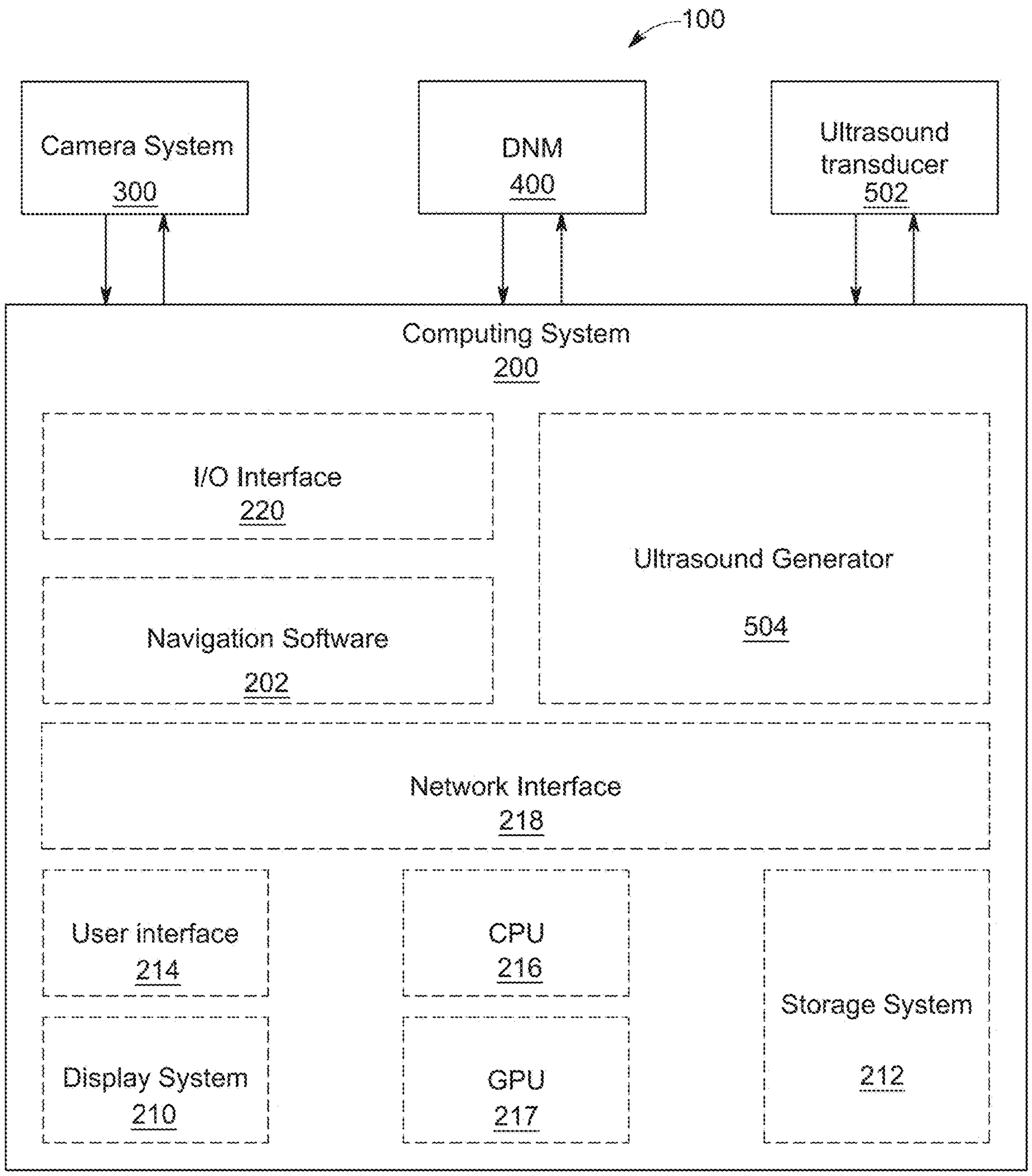
FIGS. 2A-2B are variations of schematic illustrations of a tracking and registration system according to an embodiment of the present invention.
Figure 2B:
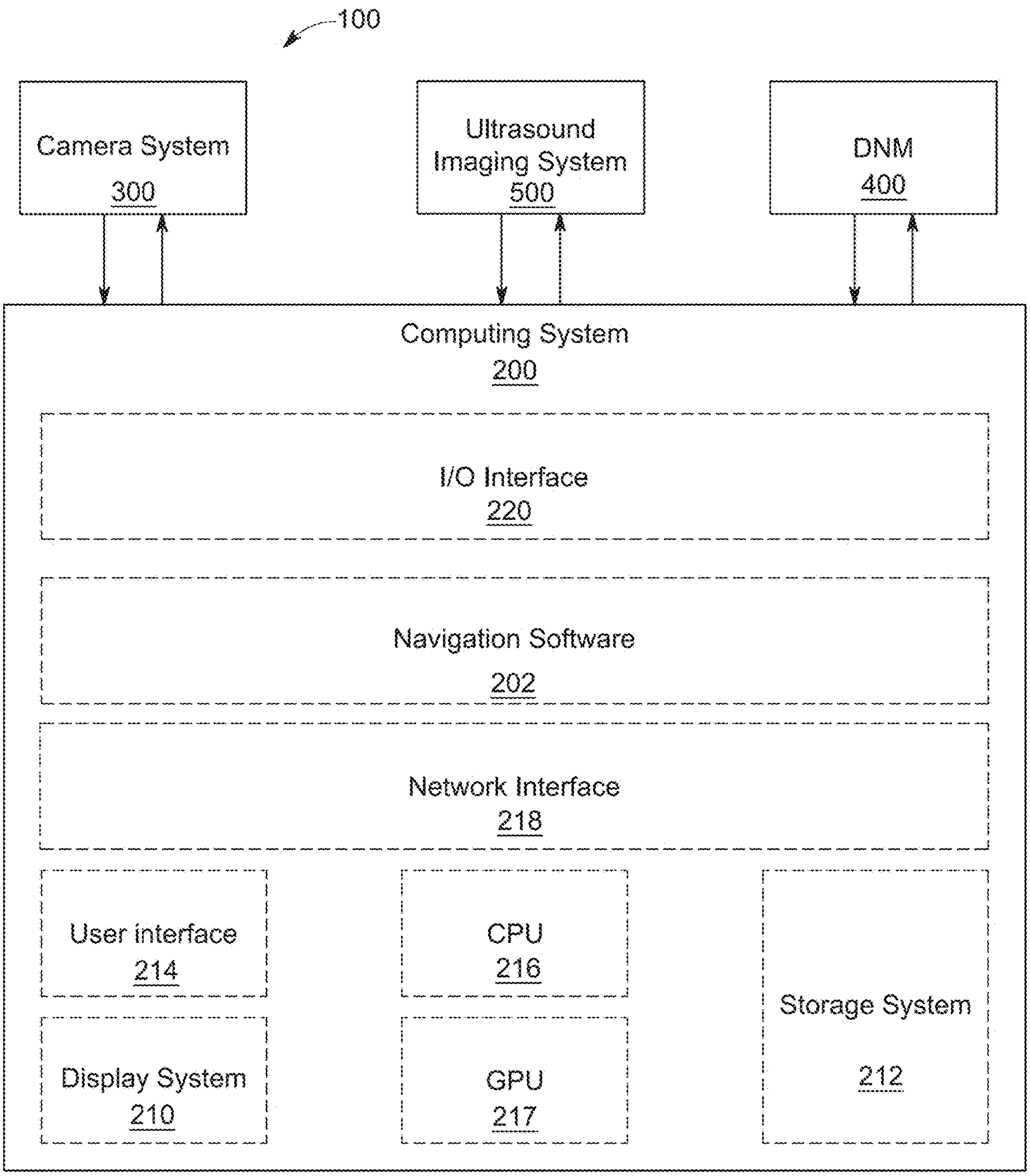

FIGS. 2A-2B are variations of schematic illustrations of a tracking and registration system 100 according to an embodiment of the present invention. Camera system 300 and ultrasound imaging system 500 are intraoperatively connected for two-way communications with computing system 200 in the variation of FIG. 2B. In FIG. 2A, the ultrasound transducer 502 is directly connected (either by wire or wirelessly) to ultrasound generator 504 withing the computing system 200. Camera image data, including images and position and orientation data from camera system 300 and ultrasound image data, including ultrasound images and position and orientation data from ultrasound imaging system 500 (FIG. 2B) or from ultrasound transducer 502 (FIG. 2A) are received by computing system 200 and processed using navigation software leveraging the tracking data from camera system 300, DNM 400 and ultrasound image data to register it with preoperative image data, including images such as CT images. All image data, either separately or in overlaid fashion can be displayed on display 210. The results of assembling ultrasound images into a volume using the tracking from camera system 300 and data from the DNM 400 can be registered to the preoperative image data and shown on display 210. Position and orientation data from other DNM's 400 such as those attached to or integrated with surgical instrument can be shown on display 210, and such DNM's can also be scanned with camera system 300 and data from the same can be fused with IMU data produced by the DNM's 400 so that models of the instruments, screws and rods, as well as positions and orientations of the same can be shown and tracked in real time.

Data can be stored in storage device/storage system 212, which may be, for example, magnetic, optical or solid state media. Computing system 200 includes at least one central processing unit (CPU) 216 and at least one graphics processing unit (GPU) 217 each interconnected with a non-transitory computer readable storage medium such as storage device/system 212. CPU 216, GPU 217 and storage system 212 each typically comprise at least one integrated circuit, and can have a variety of structures, as known in the art. Storage system 212 can be any suitable combination of volatile, e.g., random access memory ("RAM")) and non-volatile, e.g., read only memory ("ROM"), electrically erasable programmable read-only memory ("EEPROM"), flash memory, magnetic computer storage device, or optical disk) memory. Other types of non-transitory computer readable storage medium are also contemplated, such as compact disks (CD-ROM, CD-RW) and digital video disks (DVD).

Computing system 200 may also include a network interface 218 that allows the computing system to communicate with other computer systems and/or devices over a local network, wide area network or over the internet. An input/output interface 220 can be provided for interconnecting the computing system with additional input and output devices, such as a keyboard, mouse, microphone, robotic arm, or other external device, as typically known in the art.

Computing system may store navigation 202 software in storage device 212 or other memory, the navigation software comprising a plurality of computer readable instructions executable by CPU 216. When CPU 216 executes the instructions of navigation software 202 (or any other software or application stored in storage device 212, CPU 216 performs various functions implemented by those instructions, as will be discussed in greater detail below. CPU 216 or computing system 200 is therefore said to be "configured" or "operating" to perform those functions via the execution of navigation software 202. A user interface 214 which may include, but is not limited to, a keyboard, mouse, touchscreen and/or other device configured to allow a user to manually input signals to the computer system 200 may be provided.

Other data may be stored in storage device 212 such as, but not limited to: preoperative image data for a patient to be registered and operated upon, surgical plans defining various steps of a surgical procedure to be conducted on patient 1, and the like. Computing system 200 can be configured, by execution of navigation software and/or other applications, software and/or instructions, to perform various functions to capture intraoperative images depicting specified locations of the patient 1 to be navigated to and/or operated upon, for example, and to register the same with preoperative images of the patient 1 in corresponding locations, so that positions and orientations of the locations of interest can be displayed, tracked, and, optionally operated upon.

Figure 25:
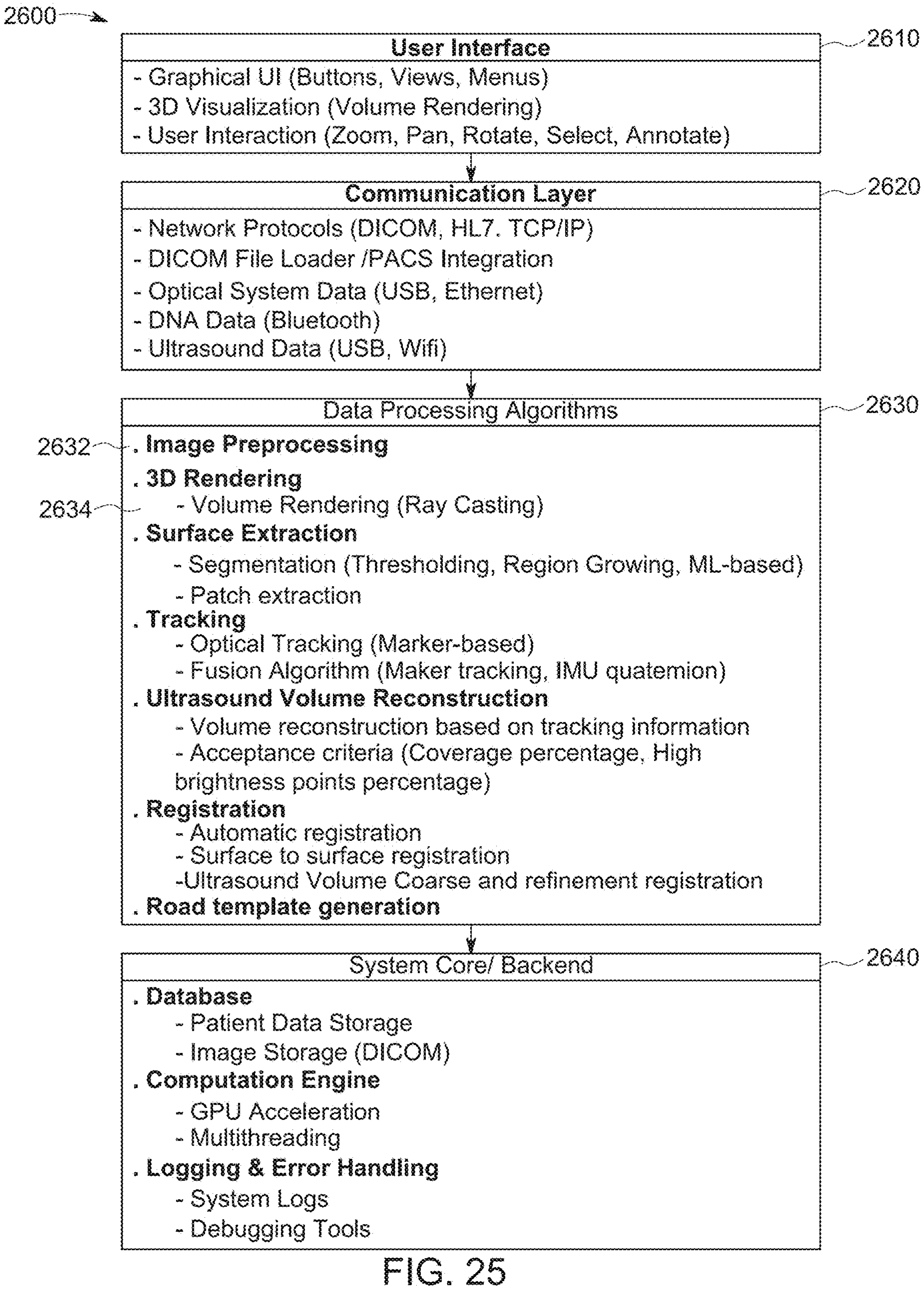
FIG. 25 is a block diagram representing a computing system according to an embodiment of the present invention, including software architecture layers employed therein.

FIG. 25 is a block diagram 2600 representing software architecture layers that may employed by computing system 200, according to an embodiment of the present invention.

A user interface layer 2610 is responsible for managing the interactions between the software and the user by providing views, menus, buttons and tools. This layer is responsible for the display of medical imaging like CT in different views and the volume rendering in the 3D view on display 210

Communication layer implements communication with different component of the system, such as the camera system 400, DNM(s) 400, ultrasound 500 and/or navigation caps 800 and also implements DICOM (Digital Imaging and Communications in Medicine) the standard for handling, storing, and transmitting medical images like the preoperative CT. The DICOM is part of the PACS (Picture Archiving and Communication System) that includes the messaging protocol HL7 (Health Level 7).

Data processing algorithms 2630 layer includes all the algorithms used in the navigation software described herein, as well as those known and common algorithms that are readily accessible. Data preprocessing algorithms (image preprocessing 2632) used on image data before display in views, or before other image processing, like image denoising are also included in this layer. 3D rendering algorithm for volume rendering may include Ray Casting and/or other known algorithm for 3D rendering.

The System Core/Backend layer 2640 is responsible for storing data in databases and also handling events and errors. It also includes computation engine responsible for algorithms acceleration using multithreading or GPU. Many algorithms listed in the data processing like rendering are GPU accelerated.

While some embodiments have been described in the context of fully functioning computers and computer systems, those skilled in the art will appreciate that various embodiments are capable of being distributed as a program product in a variety of forms and are capable of being applied regardless of the particular type of machine or computer-readable media used to actually effect the distribution.

The specific embodiments described herein refer to examples of implementation of the present invention for registration and guidance for use in spinal surgery, such as for planning and implementation of spinal curvature corrections using custom rods facilitated by use of the present invention, as well as use of the present invention to aid in the insertion of pedicle screws, both in regard to depth of insertion and well as orientations of the pedicle screws during and upon completion of insertion.

Some aspects of the present disclosure can be embodied, at least in part, in software. That is, the techniques can be carried out in a computer system or other data processing system in response to its processor, such as a microprocessor or CPU, executing sequences of instructions contained in a memory, such as ROM, volatile RAM, non-volatile memory, cache, magnetic and optical disks, or a remote storage device. Further, the instructions can be downloaded into a computing device over a data network in a form of compiled and linked version. Alternatively, the logic to perform the processes as discussed above could be implemented in additional computer and/or machine-readable media, such as discrete hardware components including large-scale integrated circuits (LSIs), application-specific integrated circuits (ASICs), or firmware such as electrically erasable programmable read-only memory (EEPROMs).

The navigation software can further include instructions for carrying out processing to determine whether acceptance criteria have been met by ultrasound imaging performed, and if acceptance criteria are not met instructing repeating an ultrasound sweep to produce replacement imaging, where this loop is continued until acceptance criteria have been met.

Although the cameras 302 used in the system 100 are typically sensitive to visible light, the wavelength of light which the cameras 302 are sensitive to, and which retroreflective disks or pattern-based markers best reflect, may vary. For example, alternate wavelengths may include, but are not limited to: infrared (IR) or near-infrared (NIR) light, ultraviolet (UV light), or even non-light frequencies, such as radio frequency (RF), wherein camaras would be replaced by antennae tuned to the frequency used. Likewise, the light source 301 when provided is a visible light source, but additionally, or alternatively other light sources, such as a laser blue or red light (or UV, IR, or other wavelengths) could be implemented.

As noted above, fiducial markers that are currently used for optically tracking positions of tools or probes need to be constantly held in an orientation that keeps the active or passive indicators of the fiducial markers in the direction of the camera(s) in direct line of sight in order to maintain the inputted visual data that is used to determine where the tip of the tool or probe lies. Such optical navigation systems are typically based on the registration of multiple fiducial markers. Regardless of the type of these fiducial markers, such as retro reflective spheres or surfaces, active markers, or pattern-based markers, the accuracy of these systems rely on the accuracy of all the elements involved, including camera resolution, calibration accuracy, layout of the fiducial markers and distances of the fiducial markers from the tips of the instruments or probes that they are mounted on.

Figure 3:
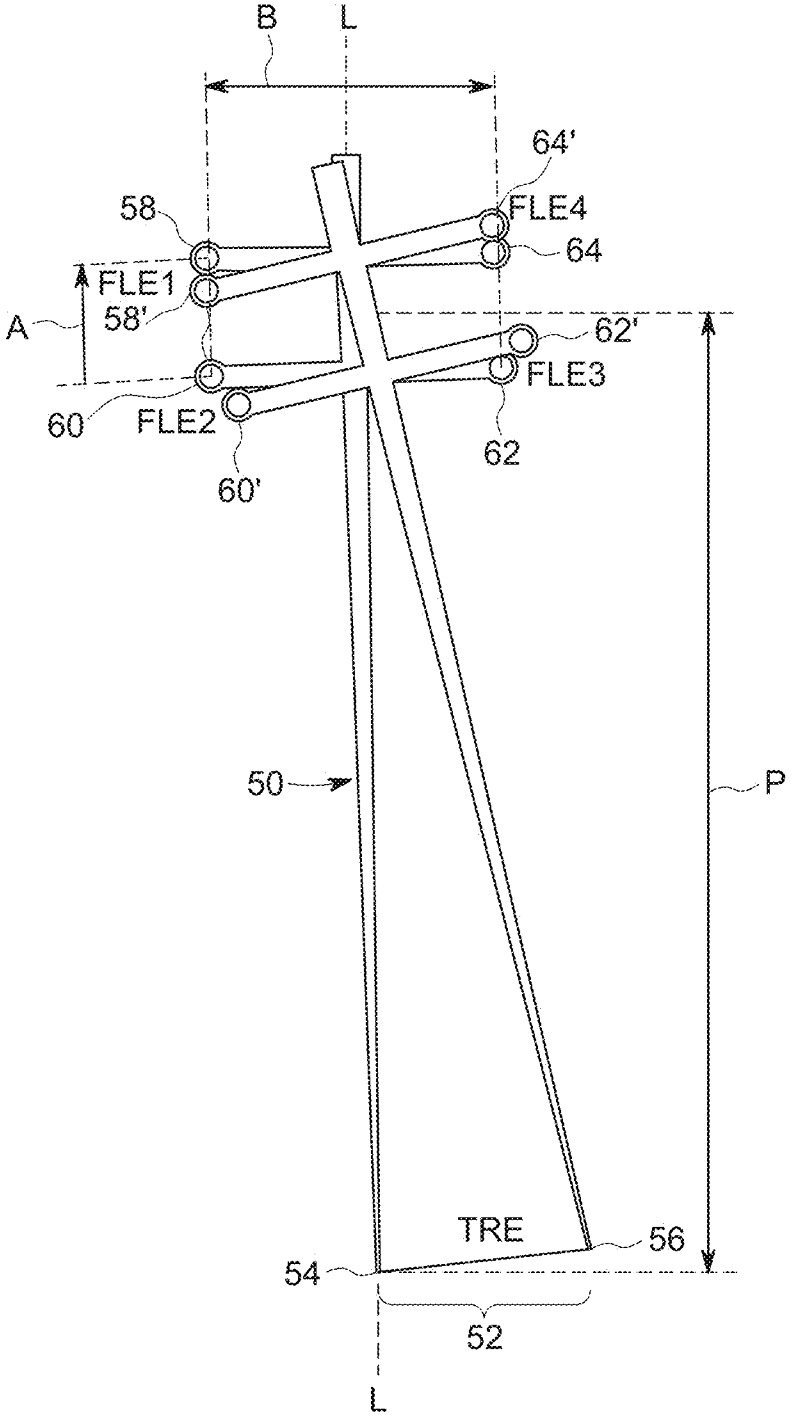
FIG. 3 PRIOR ART
FIG. 3 is a schematic representation illustrating target registration error according to the prior art.

Referring to FIG. 3, the target registration error (TRE) 52 is defined as the distance between the true location 54 and the calculated location 56 of the tip of the instrument 50 or probe to which the fiducial markers are attached. TRE has two components: a translational component and a rotational component.

According to J. B. West et el., "Designing Optically Tracked Instruments for Image-Guided Surgery", IEEE Transactions on Medical Imaging, Vol. 3, No. 5, May 2004, pp. 533-545 (which is incorporated herein, in its entirety, by reference thereto), the translational component is independent of the distribution of the fiducial marker in relation to the instrument and can be expressed as $$\langle FLE^2\rangle/N \tag{1}$$

Where N is the number of fiducial markers used and $$\langle FLE\rangle = \sqrt{FLE1^2 + FLE2^2 + \ldots + FLEN^2} \tag{2}$$

Where FLE1, FLE2, . . . , FLEN are the distances between the true positions (e.g., positions 58, 60, 62 and 64 in FIG. 3) of fiducial markers and their measured positions (e.g., positions 58', 60', 62' and 64' in FIG. 3).

In the case of optically tracked instruments, FLE is the error the optical tracking system makes when it measures the position(s) of a fiducial marker(s) attached to the instrument in the physical space coordinate system.

The rotational component can be expressed as follow:

$$\alpha\frac{P^2}{A^2}\langle FLE^2\rangle \tag{3}$$

Where $$\alpha = \frac{2+\gamma^2}{3(1+\gamma^2)}$$

in the case of four markers with rectangular layout and where $$\gamma = \frac{B}{A}, A, B$$

and P are as described in FIG. 3.

In other situations where for example fiducial marker configurations with three aligned fiducial markers, $$\alpha = \frac{4}{3}, \alpha = \frac{8+3\gamma^2}{2(4+3\gamma^2)}$$

in the case of three fiducial markers arranged in a triangle pattern, and $$\alpha = \frac{2(2+\gamma^2)}{3(1+\gamma^2)}$$

in the case of four fiducial markers arranged in a cross pattern.

A review of all these functions of $\gamma$ can determine that a will always be between $0.33<\alpha<1.33$.

In comparing the rotational component of the TRE with the translational component of TRE, in a case where P=4A, using four fiducial markers and $$\alpha = \frac{1}{2},$$

the $TRE_{Rot}=8<FLE^2>$ while $TRE_{Trans}=<FLE^2>/4$ in this case the $TRE_{Trans}=TRE_{Rot}/32$ or $TRE_{Trans}$ is about 3% of $TRE_{Rot}$, where $TRE_{Trans}$ is the translational component of TRE and $TRE_{Rot}$ is the rotational component of TRE.

$TRE_{Rot}$ can be reduced by reducing the quotient $$\frac{P}{A}$$

and $\alpha$ which can be achieved by using more markers and selecting A, B and P that minimize a and $$\frac{P}{A}.$$

However, a layout of fiducial markers that achieves a reduction of $TRE_{Rot}$ requires that B must be greater than A and the value of P needs to be as close as possible to the value of A. What this means physically is that the fiducial markers should be spread horizontally (transverse relative to the longitudinal axis L-L of the instrument) and as close to the tip 54 of the instrument as possible. These design constraints make the instrument bulky, since the fiducial markers spread horizontally greatly increase the width or cross-sectional area of the instrument in the vicinity of the fiducial markers and, even in the best cases $TRE_{Rot}$ is still about ten time greater than $TRE_{Trans}$.

Figure 4:
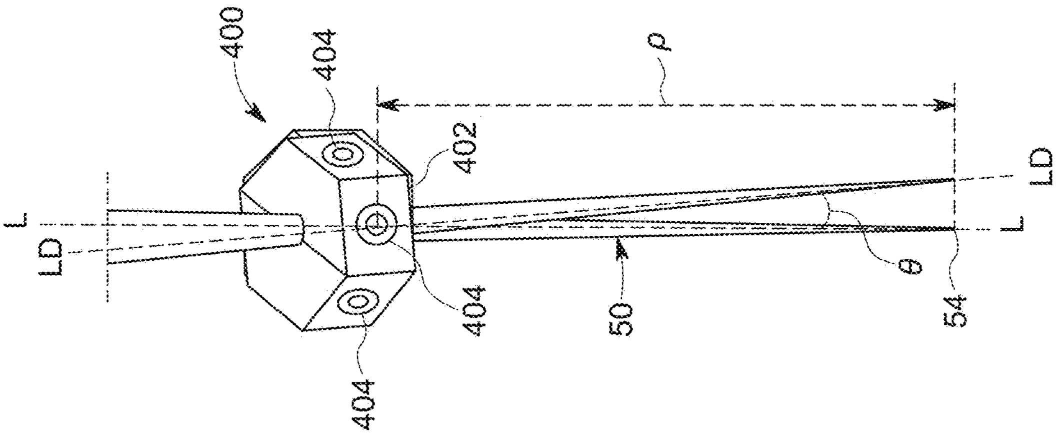
FIG. 4 is a schematic representation illustrating target registration error according to an embodiment of the present invention.

FIG. 4 illustrates advantages in accuracy provided by a directional navigation module (DNM) 400 mounted to an instrument 50, compared to the accuracy when using existing fiducial markers as discussed above with regard to FIG. 3. When using DNM 400, the orientation is provided by signals from inertial measurement unit (IMU) 700 which transmits data to computing system 200 in conjunction with the data from the tracking of the patterns 404, by running the navigation software to calculate the location and orientation. The IMU 700 in DNM 400 communicates with computer system 200, however the axes of the IMU 700 of camera system 300 and the IMU 700 of DNM 400 are aligned prior to integrating the data used from both by the computing system 200. The relative orientation of these IMUs is used in the fusion algorithm.

Figure 5A:
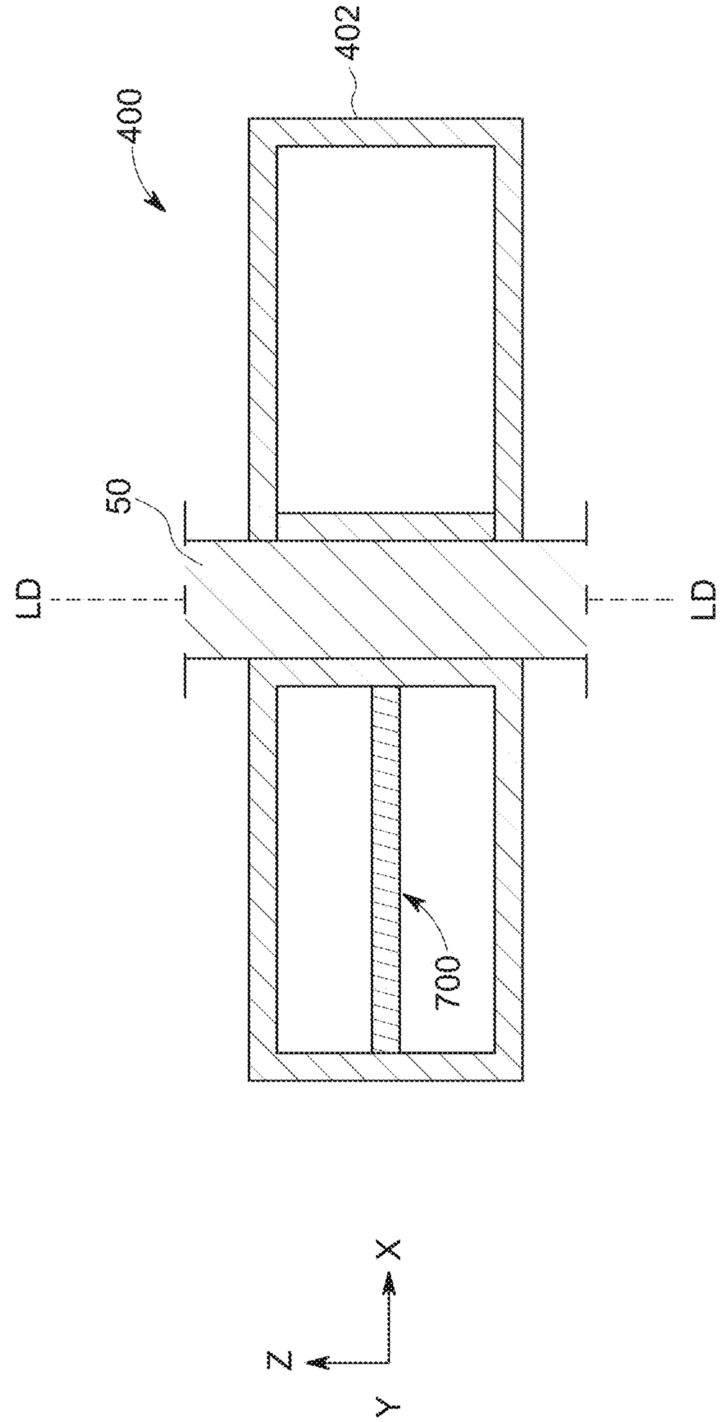
FIG. 5A is a longitudinal sectional view of a directional navigation module taken along line LD-LD in FIG. 4.

FIG. 5A is a longitudinal sectional view of DNM 400 taken along line LD-LD, which shows a longitudinal sectional view of IMU 700 mounted therein.

IMU 700 is a fusion sensor that combines sensors of various physical properties, the values of which can be processed by computing system to calculate characteristics of the instrument or probe to which the IMU 700 is attached or is integral therewith. IMU 700 preferably comprises sensing capability for at least nine degrees of freedom. In a preferred embodiment, IMU comprises sensing capabilities for ten degrees of freedom.

Figure 5B:
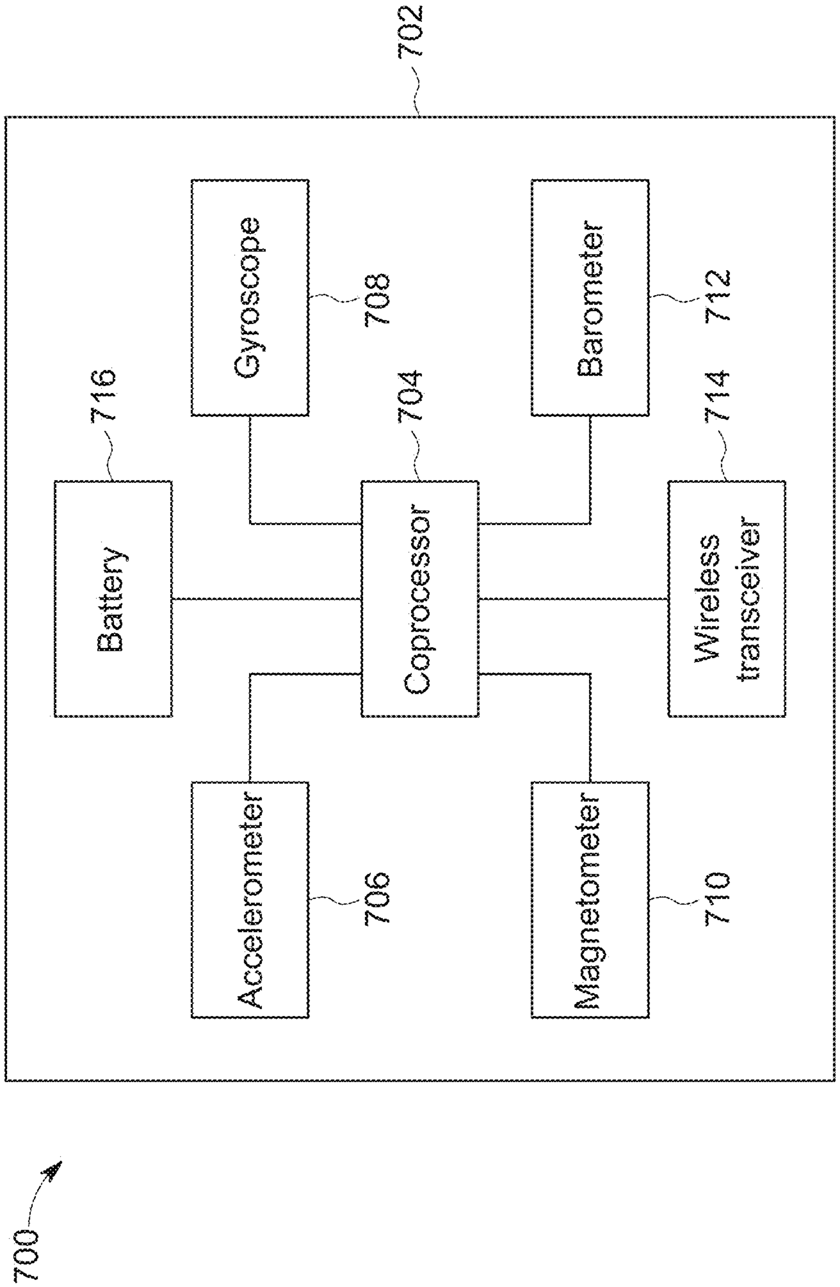
FIG. 5B schematically illustrates one non-limiting embodiment of an inertial measurement unit (IMU) that has ten degrees of freedom, according to an embodiment of the present invention.

FIG. 5B schematically illustrates one non-limiting embodiment of IMU 700 that has ten degrees of freedom (DOF). IMU 700 comprises a fusion sensor having a circuit board 702. Microcontroller Unit (MCU) motion coprocessor 704 is provided to support the functions of a 3 DOF accelerometer 706, a 3 DOF gyroscope 708, a 3 DOF magnetometer 710, and a 1 DOF barometer 712. A wireless transducer is provided for wireless communication to and from coprocessor 704, such as to and from computing system 200, for example. Wireless communication is preferably short range, radio frequency communication, preferably BLUETOOTH BLE®, although other know alternative wireless communication formats could be used. A battery 716 may be provided for powering the components of the IMU 700. Battery 716 may be silver oxide, alkaline or lithium-ion button cell or micro battery, among other possible battery types, as a power source. Battery 716 may be a rechargeable battery. Although not shown, board 702 may be provided with a circuitry for wirelessly charging battery 716 when provided as a rechargeable battery. Alternatively, IMU 700 can be provided as a single use device which is operated with a non-rechargeable battery.

As shown in FIG. 5A, IMU 700 is mounted in the shell 402 so that one axis of an X-Y-Z three-dimensional axis reference of said inertial measurement unit (IMU) 700 is parallel to the longitudinal axis LD-LD when DNM 400 is mounted to the instrument 50. Preferably the Z axis of IMU 700 is parallel to longitudinal axis LD-LD, as shown in FIG. 5A, where the X-axis of IMU 700 is horizontal, the Z-axis of IMU 700 is vertical and the Y-axis of IMU 700 is perpendicular into the drawing page. IMU 700 can be hermetically sealed within the shell 402.

Referring back to FIG. 4, the orientation of the instrument 50 is provided by the embedded high accuracy Inertial Measurement Unit (IMU) 700 along with the camera system 300 by computer system 200 executing a fusion algorithm on data received from IMU 700 and data received from camera system 300. Various fusion algorithms could be used to execute this process, including, but not limited to: Unscented Kalman Filter (UKF), the Cubature Kalman Filter (CKF), the Ensemble Kalman Filter (EnKF), Madgwick Filter and/or Mahony Filter, although the Extended Kalman Filter (EKF) is preferably used.

The data generated by the camera system 300 may be from tracking two to three markers 404 on faces of shell 402. Markers 404 may be retroreflective disks or pattern-based markers, or the like. It is noted that pattern-based markers are used for recognition by visible light cameras 302, but retroreflective disks are preferably used when camaras 302 are sensitive to near infrared (NIR) frequency. Because two to three markers are employed in the calculations, the TRE translational error ($TRE_{Trans}$) when using DNM 400 is similar to that which results when using currently available fiducial markers as described above with regard to FIG. 3. However, as already noted, $TRE_{Trans}$ is the smaller component of TRE and is typically less than 10% of the TRE). However, the $TRE_{Rot}$ that is obtained as result of the fusion algorithm using combined data from the camera system 300 and the IMU 700 is at least as good as the rotational error if only the data from the IMU 700 was used in the calculations, without the data from the camera system 300. This error can be expressed as:

$$\rho \sin \theta \tag{4}$$

Where θ is the combined accuracy of the IMU 700 from the pitch and roll (based on empirical testing of the IMU 700) and ρ is the distance of DNM 400 (measured from the center of marker 404) to the tip 54 of the instrument 50.

The size of the DNM, in at least one embodiment, preferably has a width 400W of 45 mm and a height 400H of 30 mm, (see FIG. 7C) but width 400W could be in a range from 40 mm to 60 mm and a height 400H could be in the range from 15 mm to 35 mm. Because of the size of the DNM 400 the distance p can be much smaller than the P, in the previous example representing the current art, as the DNM 400 can be placed much closer to the tip 54 of the instrument 50 without creating any inconvenience for the user. For example, P in the current art (see FIG. 3) typically is in the range from 250 mm to 300 mm while ρ (see FIG. 4) can be 100 mm to 150 mm depending on the type of the instrument; the only constraint is how much the instrument needs to be inserted in the patient without the DNM 400 getting in the way. For example, IMU 700 that can provide an accuracy for the pitch/roll of 0.1° will provide a combined accuracy of θ=0.141° and ρ=100 mm, and the $TRE_{Rot}$=0.246 mm)/Thus the $TRE_{Rot}$ can be significantly smaller than $TRE_{Rot}$ for systems based uniquely on optical tracking.

Further, use of DNM 400 provides a greater stability in tracking as the orientation and absolute direction are provided by the embedded IMU 700 at a very high refresh rate (can reach 400 Hz) which can eliminate any jitter.

Still further, DNM 400 provides enhanced navigation reliability even in the case of short interruptions of line of sight by the optical tracking system, since the orientation and absolute direction from the IMU 700 are not affected by the line of sight or interruptions thereto.

Figure 6A:
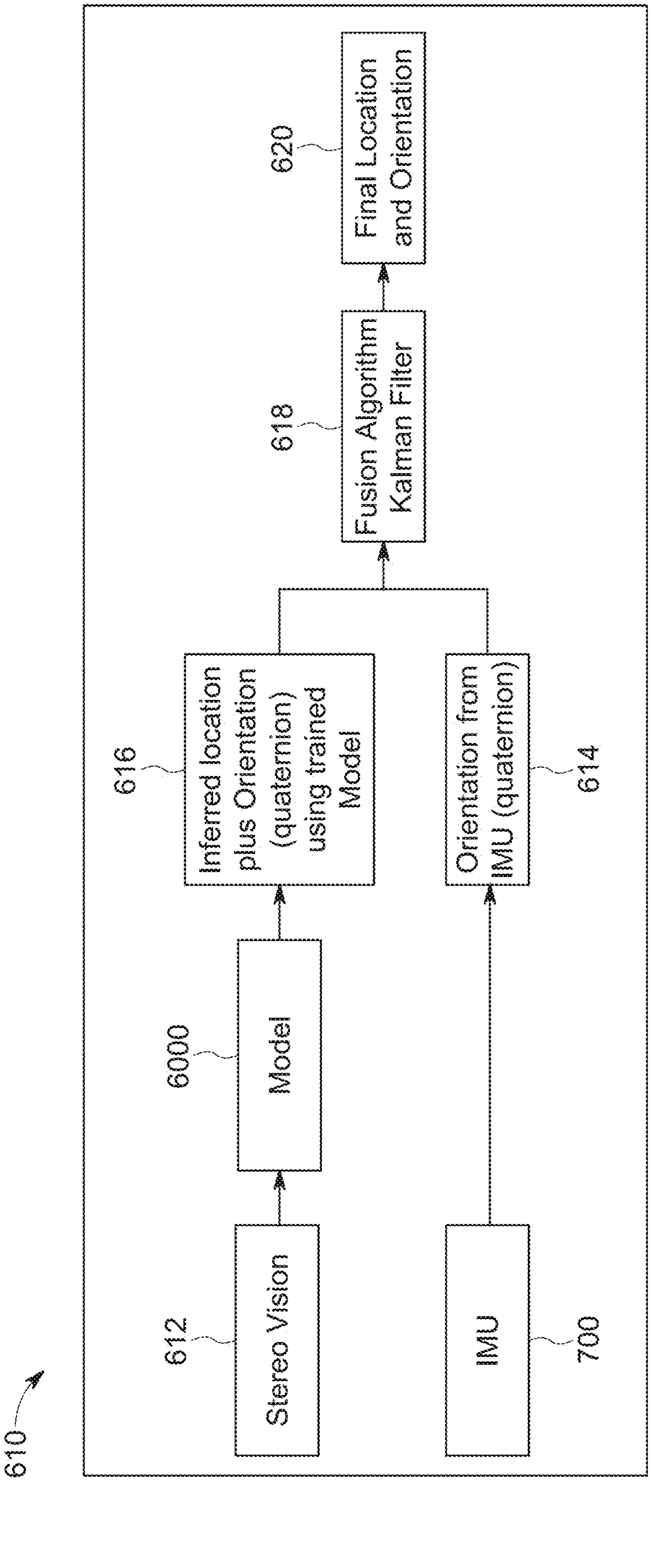
FIG. 6A is a block diagram that schematically describes a tracking algorithm used in navigation software according to an embodiment of the present invention.

FIG. 6A is a block diagram that schematically describes a tracking algorithm used in navigation software of computing system 200 for tracking DNM 400 according to an embodiment of the present invention. In this embodiment, camera system 300 provides stereo vision 612 of the object to be tracked (such as DNM 400). Tracking algorithm 610 has inputs from camera system 300 (stereo vision 612) and the IMU 700 embedded in the DNM 400. The left and right images provided by the stereo vision 612 are used by the model 6000 (described in more detail below) to calculate a pose ("DNM pose") defining the inferred position (location) and orientation 616 of the DNM 400. The inferred location plus orientation (DNM pose calculation) 616 is fused with orientation data 614 from IMU 700 using a fusion algorithm 618 (such as Unscented Kalman Filter (UKF), the Cubature Kalman Filter (CKF), the Ensemble Kalman Filter (EnKF), Madgwick Filter and/or Mahony Filter, or the like, although the Extended Kalman Filter (EKF) is preferably used). The fusion provides the final (optimal) location and orientation 620 of the object being tracked (such as DNM 400) in real-time.

Tracking algorithm 610 leverages the following generating final location and orientation calculations: triangulation made possibly by stereo vision inputs 612; known geometry (such as provided by CAD modeling) of the object being tracked (such as DNM 400) and known geometries and locations of the markers 404 (relative to the object being tracked, such as provided by CAD modeling) of the object (such as DNM 400) being tracked; known eccentricities of the patterns of the markers 404 and the fact that at least portions of at least three markers' patterns 404 are visible due to tracked object (such as DNM 400) geometry; a dataset D of stereo images labeled with measured locations and orientations; and data from IMU 700.

Model 6000 is a deep learning model that uses a hybrid approach that internally triangulates patterns, fuses geometric pose estimates with learned features, and refines the final pose (location and orientation) prediction 620. Differentiable geometric operations (triangulation, PnP (used for the pose, defined as the location and orientation of DNM 400) are integrated with deep learning, enabling robust pose estimation even with partial pattern occlusions. The accuracy is also increased as the model 6000 uses a reprojection loss function based on the DNM 400 CAD model enforcing geometric consistency.

In an embodiment for tracking DNM 400, model 6000 can be trained on a dataset D composed from left and right images of DNM 400 taken using the camera system 300, labeled with the orientation of the DNM 400 and the location of the tip of the instrument to which the DNM 400 is attached, in the coordinate system of the of the camera system 300. Images provided in dataset D are taken while the camera system 300 is in a fixed position and the instrument, with the mounted DNM 400, is fixed to a moving controlled arm. This allows images to be taken from different measured locations and orientations. The images can also be taken in various lighting conditions mimicking the wide variety of surgical lighting that could be present in various real surgical environments. The dataset can be further augmented with images taken with partially hidden patterns (markers 404) on the faces 406, 408, 410) of the DNM 404, mimicking blood stains or any other fluids that may happen in real surgery conditions. The dataset can be still further augmented synthetically by adding, noise, occlusion and artificial lighting according to known techniques of data augmentation. A formula for dataset D according to an embodiment of the present invention as described immediately above is:

$$D=\{(x^{(1)},y^{(1)}),(x^{(2)},y^{(2)}),\ldots,(x^{(N)},y^{(N)})\} \tag{5}$$

where:

$$x^{(i)}=(Img^{i}_{left},Img^{i}_{right})$$

represent the images taken by the system 300 where: left and right cameras and where: $y^{(i)}=(p^i,q^i)$ and $p^i$ is the measured location of the tip of the instrument and $q^i$ represent the quaterniom representing the measured orientation of DNM for the images i.

Figure 6B:
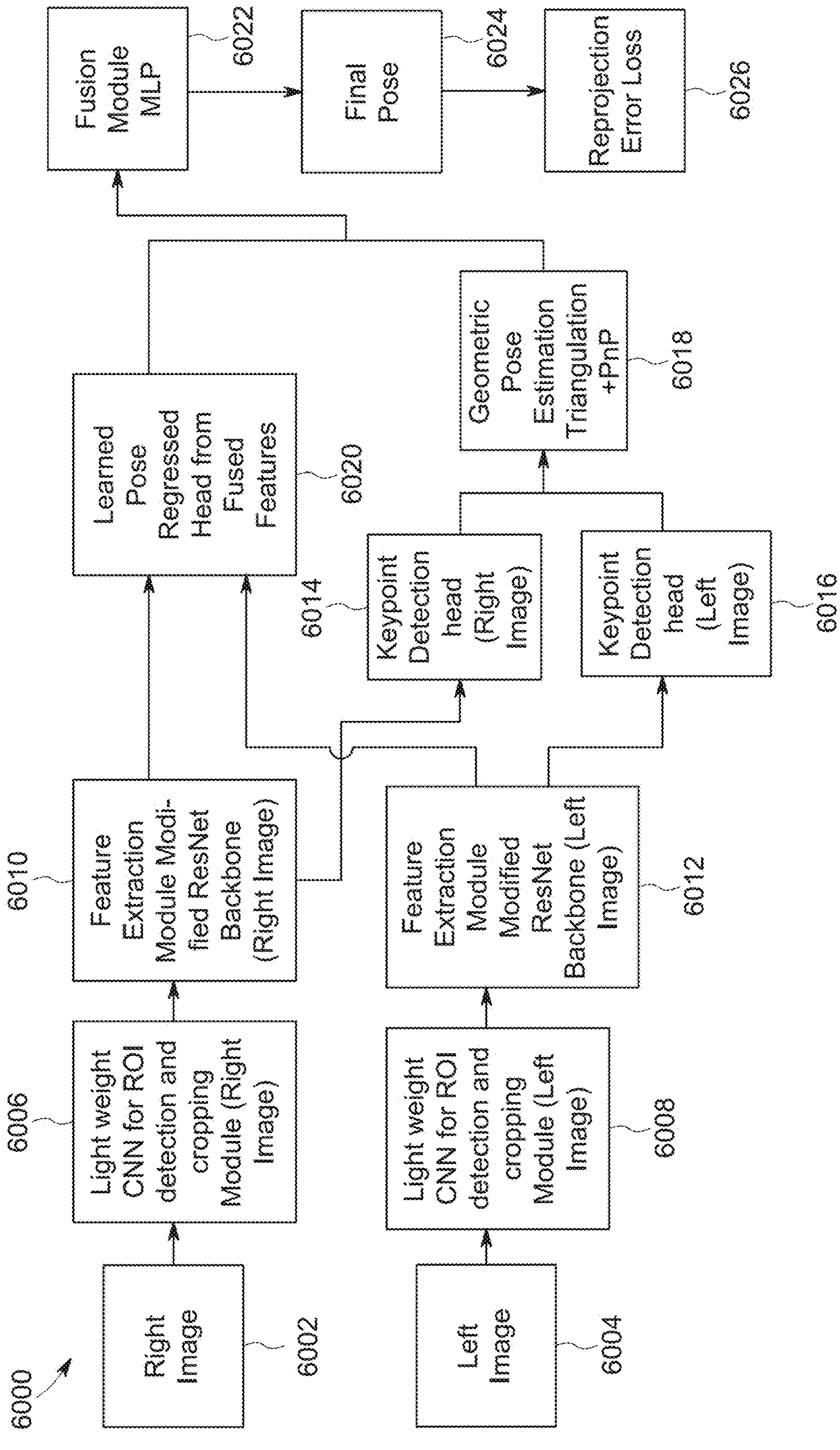
FIG. 6B is a block diagram that schematically describes a deep learning model that can be used in a tracking algorithm according to an embodiment of the present invention.

FIG. 6B is a block diagram that schematically describes a deep learning model 6000 that can be used in a tracking algorithm 610 according to an embodiment of the present invention.

Boxes designated 6002 and 6004 represent right and left image data inputted as stereo vision 612 in FIG. 6A. Right 6002 and left 6004 image data are left and right high-resolution monochrome images. The high resolution images typically have a resolution greater than or equal to 3 mega pixels (MP), typically a resolution in the range from 3 MP to 8 MP. In one preferred embodiment the resolution is 6.3 MP (3072×2048).

Region of Interest (ROI) detection and cropping modules 6006 and 6008 are provided for right and left image data respectively, based on lightweight CNN sub-network to localize the DNM 400 and patterns of markers 404 in both stereo images. The sub-network output of 6006 and 6008 bounds around the DNM 400 and instrument (e.g. 512×512), preserving high-resolution details of patterns/markers 404. Cropping of the high-resolution left and right images is done while preserving stereo alignment (consistent cropping in left/right images to maintain epipolar geometry).

Feature extraction modules 6010 and 6012 each employ a modified ResNet18 backbone to provide a subnetwork that receives the cropped high resolution right and left images, respectively. The right and left ResNet18 backbones are used for features extraction with a first layer modified for grayscale input (1 channel). The rest of the backbone is initialized with weights from ImageNet and trained on left/right ROIs (512×512) independently. The outputs are hierarchical feature maps (e.g., edges, textures, marker boundaries, eccentricity of markers) that encode visual patterns from the input images, and serve as input for the keypoint detection heads 6014 and 6016 and pose regression head 6020.

Keypoint detection heads 6014 and 6016 are provided for right and left images, respectively. Keypoint detection heads 6014 and 6016 receive as input the output of the features extracted by the ResNet backbones of feature extraction modules 6010, 6012 with low spatial resolution. Each keypoint detection head 6014, 6016 comprises a decoder bloc used to restore the spatial resolution and detect the precise location of the 2D patterns and output 2D coordinates of the keypoints on the left and right images.

Outputs of the keypoint detection heads 6014 and 6016 are inputted to a module 6018 that performs geometric pose estimation. Module 6018 uses a differentiable triangulation (e.g., using Kornia library) to compute 3D patterns' positions from 2D keypoints using stereo geometry and a differentiable PnP to solve for the object's pose (t_geo, R_geo) using triangulated 3D markers 404 and the known CAD model.

Module 6020 represents a learned pose regression head, where fully connected layers regress the pose (t_learned, R_learned) directly from fused backbone features, and output the position (XYZ)+orientation (quaternion) making up the pose.

The pose outputted by 6020 and the pose estimation from 6018 are inputted to fusion module 6022. Thus, 6022 takes as input geometric pose (t_geometric, R_geometric) from 6018 and learned pose (t_learned, R_learned) from 6020 and uses MLP subnetwork to dynamically fuse the geometric pose and learned pose into a refined pose ("final pose", t_final, R_final), balancing geometric precision and learned robustness. (t for Translation and R for Rotation). The refined pose, also called the final pose is outputted to 6024.

A reprojection error calculation is performed at 6026. The reprojection error calculation is based on the projection of known 3D patterns for each pose (geometric, learned, final) and projection of the CAD model's 3D patterns into the image using the predicted pose, where the loss function is the Mean Squared Error (MSE) between projected and detected 2D keypoints.

Model 6000 may use any or all of the following loss functions as feedback:

Pose Regression Loss $$\text{Position } \mathcal{L}_{pos}=MSE(t_{pred},t_{gt}) \tag{6}$$

$$\text{Orientation } \mathcal{L}_{geodesic}=\theta=\arccos\left(\frac{\operatorname{trace}(R^{T}_{pred}R_{gt})-1}{2}\right) \tag{7}$$

Reprojection Loss:

$$\mathcal{L}_{reproj-total}=\mathcal{L}_{reproj-geo}+\mathcal{L}_{reproj-learned}+\mathcal{L}_{reproj-final} \tag{8}$$

and $$\mathcal{L}_{reproj}=\frac{1}{N}\sum_{i=1}^{N}\left\|\pi(K(RP_i+t))-p_i^{detected}\right\|_2^2 \tag{9}$$

$P_i$: 3D coordinates of the $i^{th}$ pattern center in the DNM frame (from CAD model)

π: Perspective projection (convert 3D to 2D)

K: Camera intrinsic matrix.

$$p_i^{detected}\text{: Detected } 2D \text{ coordinate } of\ i^{th} \text{ pattern center} \tag{10}$$

and $$\mathcal{L}_{total}=\mathcal{L}_{pos}+\mathcal{L}_{geodesic}+\lambda\mathcal{L}_{reproj-total}$$

Where λ is a tuned hyperparameter.

The loss function ensures cross-modal feedback through all the model components: keypoints detection, triangulation and pose regression; achieving a sub-pixel accuracy by aligning CAD model with observations.

The model architecture can have other variations, for example: while ResNet18 backbone is used in the described model 6000, other ResNet like 34 or 50 or EfficientNet backbones can be used instead. Other modifications to the model 6000 can be used, such as, but not limited to: adding attention mechanisms or using a different sub-network at different stages of the model.

Further, while the algorithm 610 uses fusion algorithm (Kalman filter) at 618 to fuse the pose data from the model 6000 and the IMU 700, a variation of the algorithm 610 and the deep learning model 6000 can integrate the IMU 700 data in the model 6000 to be fused with the geometric pose and the learned pose in the fusion module 6022.

Figure 7A:
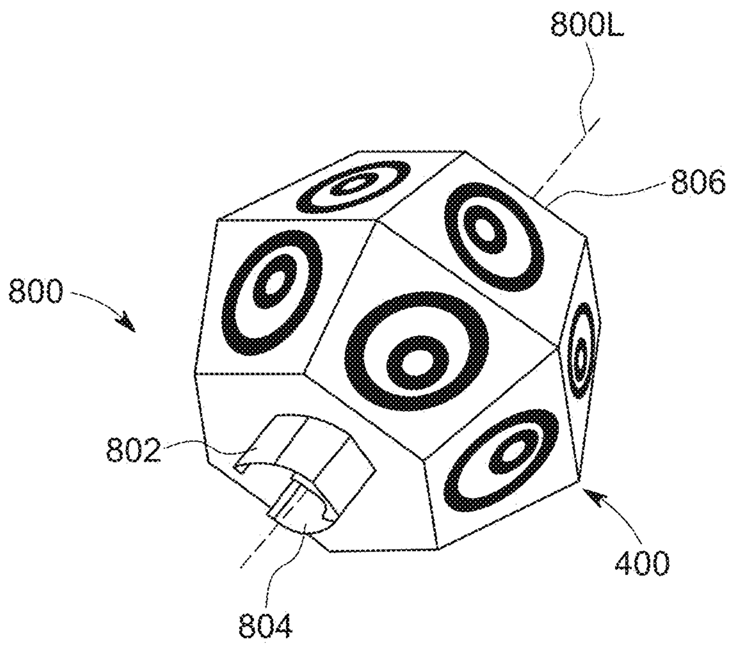
FIG. 7A is a perspective view of a navigation cap according to an embodiment of the present invention.
Figure 7B:
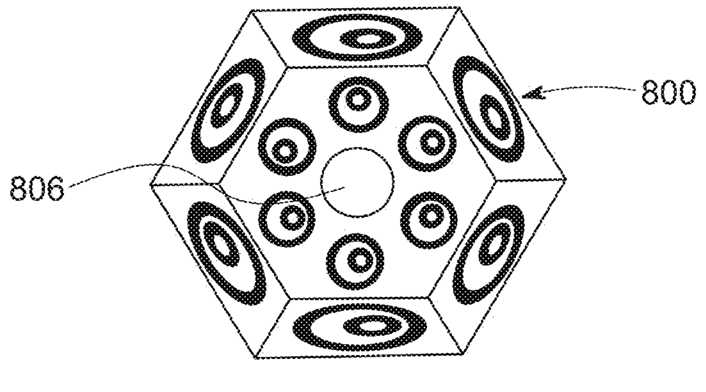
FIG. 7B is a top view of the navigation cap of FIG. 7A.
Figure 7C:
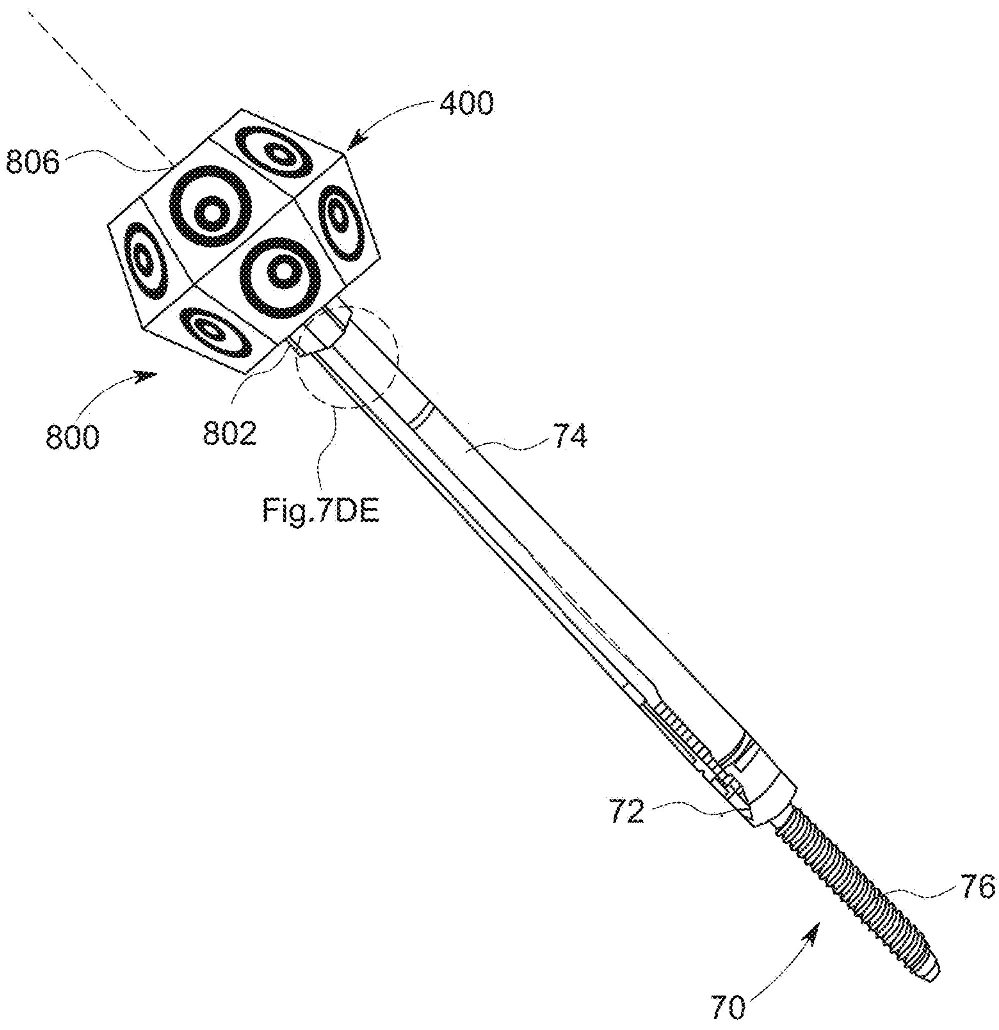
FIG. 7C is a perspective view of a navigation cap that is attached to an extended pedicle screw, according to an embodiment of the present invention.
Figure 7D:
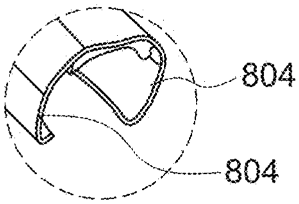
FIG. 7D is a partial view showing a distal end portion of a connector of the navigation cap shown in FIG. 7C.
Figure 7E:
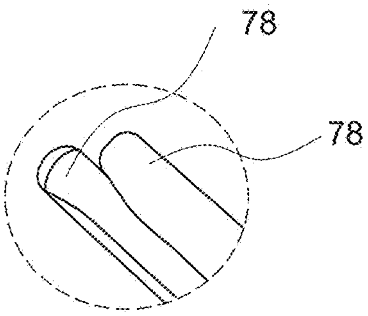
FIG. 7E is a partial view showing a proximal end portion of the extended tabs of FIG. 7C.

FIG. 7A is a perspective view of a navigation cap 800 according to an embodiment of the present invention. Navigation caps 800 may be 3D-printed or machined, devices with a top end portion having an optical marker or plurality of optical markers in addition to an IMU 700 in similar way as for the DNM 400 and with a bore 806 passing therethrough coaxially with the longitudinal axis 800L of navigation cap 800. Preferably, bore 806 is cylindrical in shape with a circular cross-section, but could have various alterative shapes in cross-sections, such as oval, elliptical, rectangular, other polygonal, or irregular shape. Navigation cap 800 further includes a connector, such as collar 802 at a distal portion configured to attach to the proximal end of tabs 74 (i.e., extended parts of the tulip) of a pedicle screw 70, as illustrated in FIG. 7C. The fit has an interior and exterior support to the proximal end of tabs 74 preventing the tabs 74 from collapsing inward or expanding outward. It is noted that the distal end 804 of the navigation cap rod matching features on the screw 70 are not found on the screw tulip 72 but on the screw shaft 76. Although screwing of the distal end 804 into the tulip 72 can be an alternative means of connection, it is typically not the preferred embodiment, particularly with the use of polyaxial screws 70, as such a connection could inhibit the polyaxiality of the screw 70. Therefore connection by threads 808 (see FIG. 7I) into the screw shaft is preferred, to maintain polyaxial functionality. FIGS. 7A, 7C and 7I only show examples of various embodiments/designs that can provide fixed and rigid connection to the screw shaft. Many other embodiments/designs can be used depending on the design of the screw shaft proximal end design, e.g., conical, hexagonal etc.

The navigation cap bore 806 allows for instrument access (such as a screw driver, or other instrument having an elongate shaft) to screw tulip head 72 and the screw shaft proximal end 76 of a pedicle screw 70. Navigation caps 800 are configured to be scanned with the camera system 300 and to send orientation data via IMU's 700 to computing system 200, which, allows for screws 70 to be navigated into position using a screw driver. Additionally, when screws are placed, their locations and orientations obtained using navigation caps 800 are used by the navigation software, to calculate needed rod lengths, coronal bends and a needed reduction at each pedicle screw 70 to carry out a predefined spinal correction. The calculations are made based on the positions and orientations of the pedicle screws 70, and used to create a template for rod bending to produce a customized rod 80 to facilitate a rod insertion process into screw tulips (heads) 72 during an MIS surgery and can also be used to carry out a predefined spinal sagittal correction. Additionally, the navigation caps 800 allow for continuous tracking of the screw heads' 72 orientations, which are used in rod navigations. Navigation caps 800 can be detached from the respective screws 70, at the desired time, by simply pulling/retracting the navigation caps 800 out of engagement with the screws 70/tabs 74.

The navigation cap 800 in FIG. 7A includes a navigation module 400 with a clip-like collar 802 extending from a distal end portion thereof. An interior profile 804 of collar 802 shaped and dimensioned so that it can be fit with a matching proximal end 78 of tabs 74 of pedicle screw 70 (see FIGS. 7C, 7D and 7E). The proximal end portions 78 of tabs 74 of pedicle screw 70 are inserted in the matching shapes 804 of the collar 802. The navigation cap 800 has also a bore 806 (see FIG. 7B) coaxial with the Z axis of the DNM 400.

Directional navigation module (DNM) 400, as noted above, is provided with IMU 700 within shell 402. Shell 402 extends completely (360 degrees) around the shaft or proximal end portion of the instrument or device to which it is attached or integral with. The cross-sectional shape of shell 402 may be pentagonal, hexagonal or octagonal, or other polygonal shape. Triangular, or rectangular shapes can be used, but are less preferable as they will typically not allow enough faces/markers to be seen by the camera system 300 in some orientations. Also increasing the number of faces over six (hexagonal) can necessitate the reduction in the size of the markers 404 contained on each face, making it less desirable.

Shell 402 may have a conical shape, or may not. Each of the side faces 406 (faces located in between the top 408 and bottom 410 surfaces of shell 402) may be provided with a marker 404 such as a retro reflective disk, pattern-based marker, or the like. DNM 400 is equipped with Bluetooth BLE that allows the DNM 400 to communicate the orientation of the instrument to the computing system 200/navigation software. Each IMU 700 is provided with a unique address (such as a MAC address, or the like), uniquely identifying each of the DNM(s) 400 in use during a procedure.

FIG. 7C is a perspective view of a navigation cap 800 attached to an extended pedicle screw 70, according to an embodiment of the present invention. Extended screws 70 are used in MIS procedures and extended tabs 74 allow the surgeon to see the orientations and positions of screws as they extend out of the incisions, and this can be used to guide the rod insertion process.

Figure 7F:
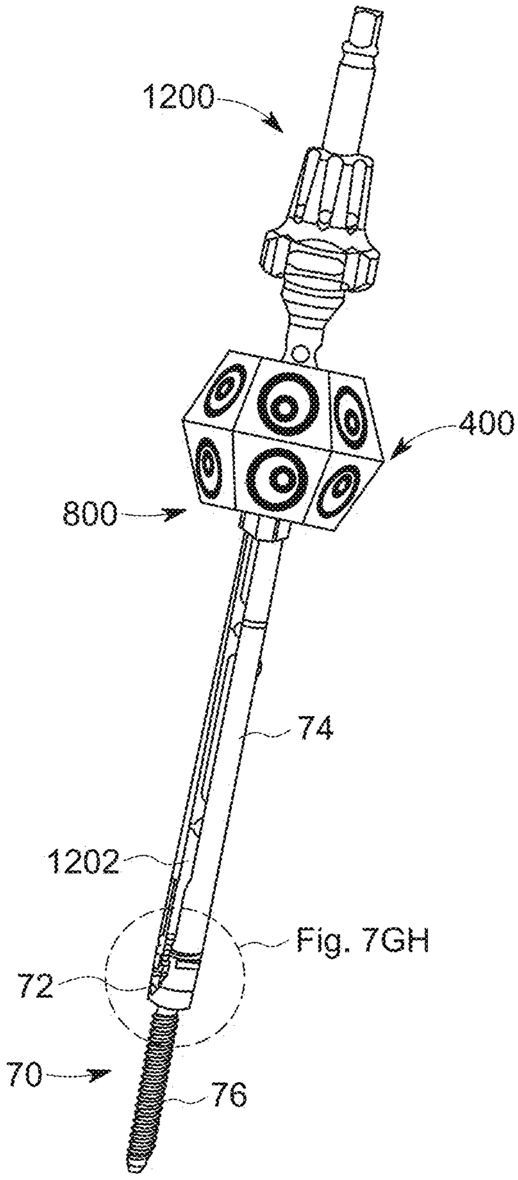
FIG. 7F illustrates a screw driver having been inserted through the bore of a navigation cap and tabs, according to an embodiment of the present invention.
Figure 7G:
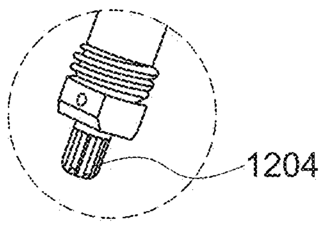
FIG. 7G shows a distal end portion of the screw driver of FIG. 7F.
Figure 7H:
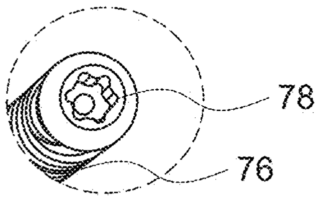
FIG. 7H shows a proximal end portion of the screw shaft of FIG. 7F.
Figure 7I:
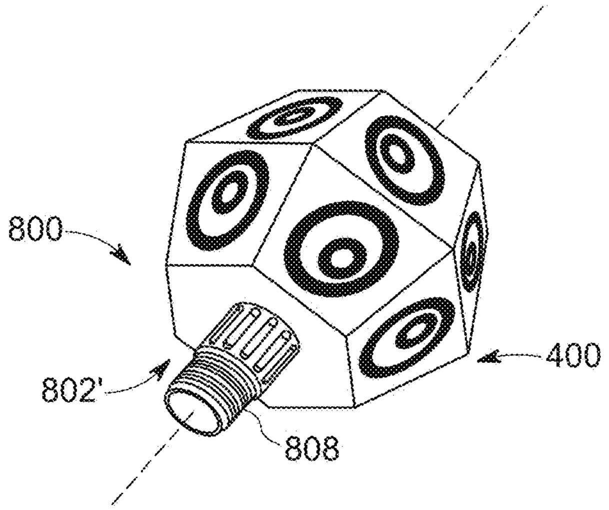
FIG. 7I shows a navigation cap having a connector that is cylindrical with threads, according to an embodiment of the present invention.

FIG. 7F is a perspective view of screw driver 1200 inserted through the bore 806 and the collar 802 of navigation cap 800. The shaft 1202 of screw driver 1200 is also inserted through the tabs 74 and the tulip head 72 of pedicle screw 70 and its distal end 1204 (See FIG. 7G) is inserted into the matching shape 78 on shaft 76 proximal end of pedicle screw 70 (See FIG. 7H). The screw driver 1200 once fully inserted locks coaxially the navigation cap 800 with respect to the screw shaft 76, allowing the navigation software to track the orientation and the position of the screw 70, since the navigation cap is also fixed rotationally and translationally relative to the screw 70. Once a screw 70 is placed, the screw driver 1200 can be pulled away, and the navigation cap 800 can be used to track the orientation of the tulip 72 of pedicle screw 70 which is used to navigate rod insertion.

Figure 7J:
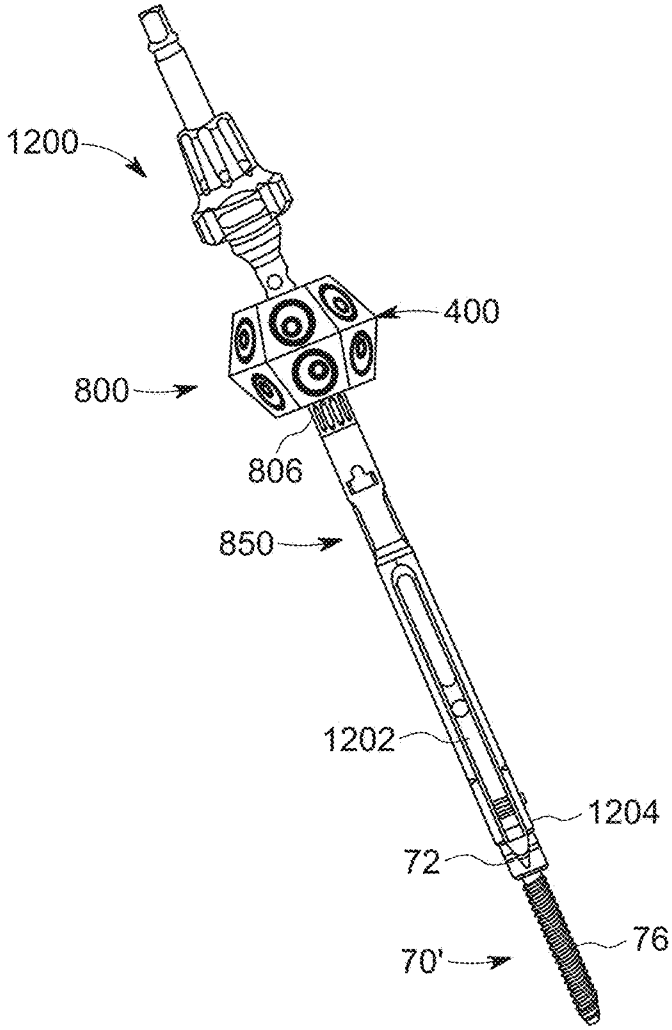
FIG. 7J illustrates a screw driver having been inserted through the bore of a navigation cap of FIG. 7I and an extension tube attached to a non-extended pedicle screw, according to an embodiment of the present invention.

Alternatively, navigation cap 800 may be provided with a connector other than collar 802. For example, the embodiment of FIG. FIG. 7I has a connector 802' that is cylindrical with threads 808 provided on at least a distal end portion thereof. Threads 808 are preferably external, but could alternatively be provided as internal threads. Threads 808 are configured to mate with an extension tube 850 (See FIG. 7J) having mating threads (not shown). The extension tube 850 mated with navigation cap 800 can be attached to a non-extended pedicle screw 70'. Once a screw driver 1200 is inserted through bore 806 of navigation cap 800 and through extension tube 850 and its distal end 1204 is fully inserted in the matching shape on the proximal end of the screw shaft 76 of pedicle screw 70', the tulip 72 of pedicle screw 70' and the navigation cap 800 are locked coaxially to the shaft 76 of the pedicle screw 70', allowing the navigation software to track the orientation and the position of the screw 70', as the navigation cap 800 is fixed both rotationally and translationally relative to the screw 70'. The features of distal end 1204 match the features of the proximal end of the shaft 76 of screw 70. The shaft 1202 of the driver 1200 is inserted through the tulip 72, the bottom of which provides an access to the proximal end of the shaft 76 of screw 70. After the screw driver 1200 is pulled out, the navigation cap 800 can be used to track the orientation of the tulip 72 of the pedicle screw 70'. Many other designs of the connector 802 extending from the distal end portion of the navigation cap 800 can be used in order to attach the navigation cap 800 to the tulip 72 or to the tabs 74 of pedicle screw 70, and allow for inserting a screw driver 1200 to be attached to the screw shaft proximal end, locking coaxially the navigation cap 800 to the screw shaft 76 of pedicle screw 70/70'.

Figure 7K:
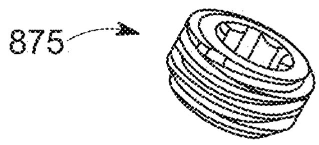
FIG. 7K is a perspective view of a set screw according to an embodiment of the present invention.

FIG. 7K is a perspective view of a set screw 875 according to an embodiment of the present invention. Set screws 875 can be inserted using a screw driver 1200 through the bore 806 of navigation cap 800 and used to secure the rods 80 in a spinal procedure by screwing the set screws 875 into the pedicle screw heads 72 after the rods 80 have been placed into the desired positions.

Figure 8A:
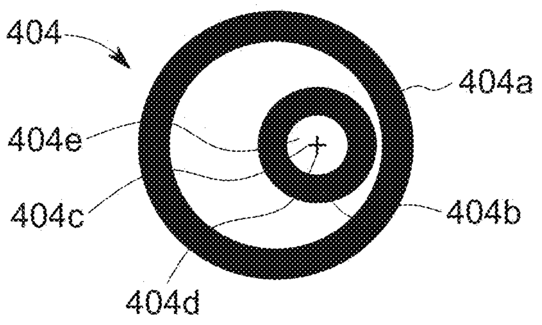
FIG. 8A-8H show examples of various pattern-based markers that can be provided on one or more of side, top and/or bottom faces of various embodiments of DNM's according to embodiments of the present invention.
Figure 8B:
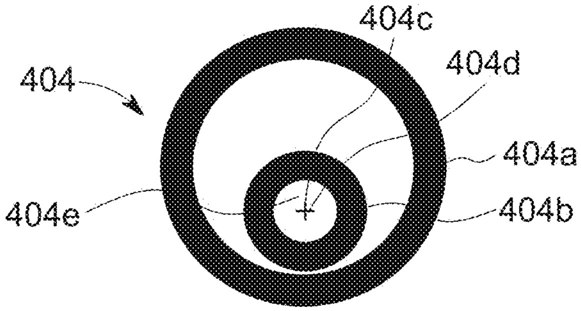
Figure 8C:
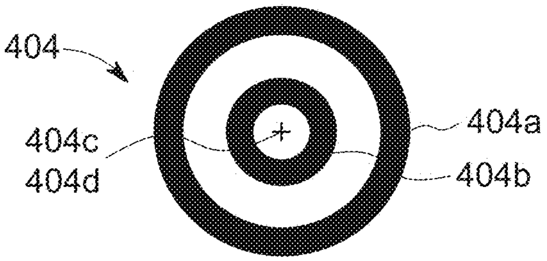

FIG. 8A-8H show examples of various pattern-based markers 404 that can be provided on one or more of side, top and/or bottom faces 408, 408, 410 of various embodiments of DNM's 400 according to embodiments of the present invention. The pattern-based markers 404 are formed from an outer shape 404*a* and an inner shape 404*b*. The outer and inner shapes 404*a*, 404*b* can be either concentric or eccentric. The shapes used in the markers 404 are basic shapes like circles, ellipses, squares, rectangles or triangles. The use of these basic shapes instead of ArUco markers for example is motivated by the small size of the faces 406, 408, 410 and the need for high detectability and occlusion robustness. FIGS. 8A, 8B and 8C are examples of pattern-based markers 404 having an outer black disk with a concentric white disk forming together an outer shape 404*a* with its center 404*c* and an inner shape 404*b* with its center 404*d*. In FIG. 8A the vector 404*e*, defined as the vector originating from the center 404*c* of the outer shape 404*a* to the center 404*d* of the inner shape 404*b*, has a different direction than the vector 404*e* in FIG. 8B. In FIG. 8C the centers of the outer and inner shapes are identical making the vector 404*e* of norm zero, and the shapes 404*a* and 404*b* concentric. The use of different markers 404 on the faces 406 of DNM 400 with vectors 404*e* having either different directions or norms allows for uniquely defining the orientation of the DNM 400. This same principle applies to use of different markers on the tops and bottoms of DNM 400.

Figure 8D:
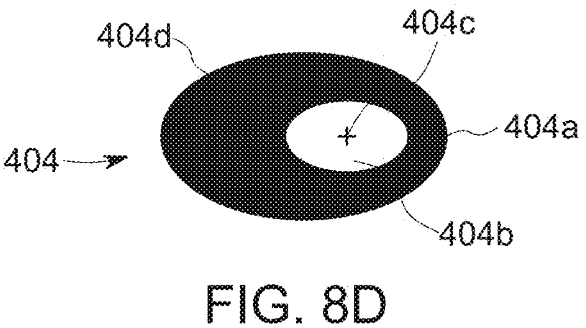

FIG. 8D shows another embodiment of a pattern-based marker 404. In this embodiment, marker 404 has an outer black oval as outer shape 404*a* and eccentric white oval as inner shape 404*b*. A change in the location of the inner white oval 404*b* will produce a different vector 404*e* and a different pattern.

Figure 8E:
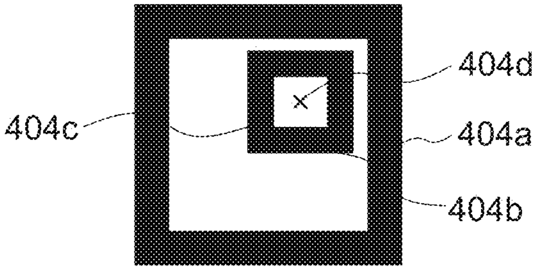

The embodiment of FIG. 8E shows a pattern-based marker 404 having a black outer square with a concentric white square forming together an outer shape 404*a* and eccentric black inner square surrounding concentric white inner square and forming eccentric inner shape 404*b*. A change in the location of the inner square 404*b* will produce a different vector 404*e* and a different pattern.

Figure 8F:
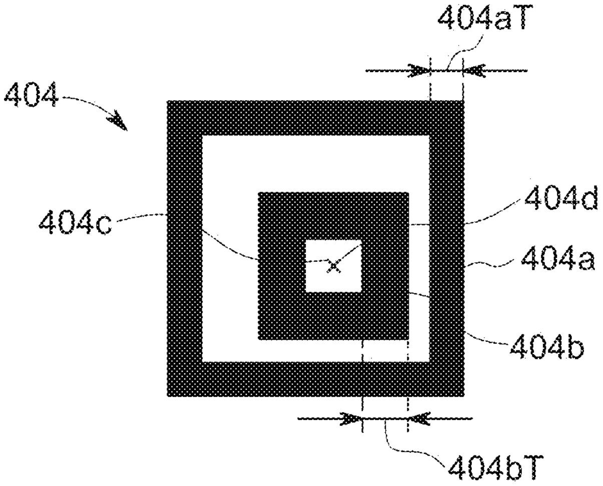

FIG. 8F shows a pattern-based marker 404 having a black outer square 404*a* and eccentric, black inner square 404*b*, according to an embodiment of the present invention. The thickness 404*a*T of the outer square 404*a* is less than the thickness 404*b*T of the inner square 404*b*. A change in the location of the inner square 404*b* relative to the outer square 404*a* will produce a different vector 404*e* and a different pattern.

Figure 8G:
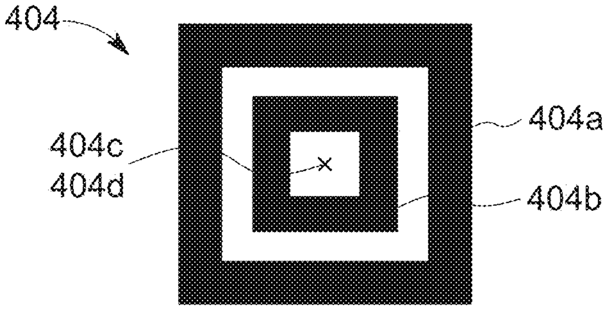

FIG. 8G shows another pattern-based marker 404, according to an embodiment of the present invention. Black outer square 404*a* and black, concentric inner square 404*b* each have the same thickness.

Figure 8H:
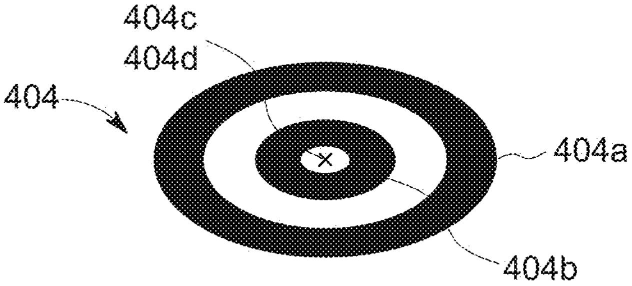

In the embodiment of FIG. 8H, pattern-based marker 404 has a black outer ellipse 404*a* and concentric, black inner ellipse 404*b*. The outer and inner ellipsis are of the same thicknesses.

Figure 8I:
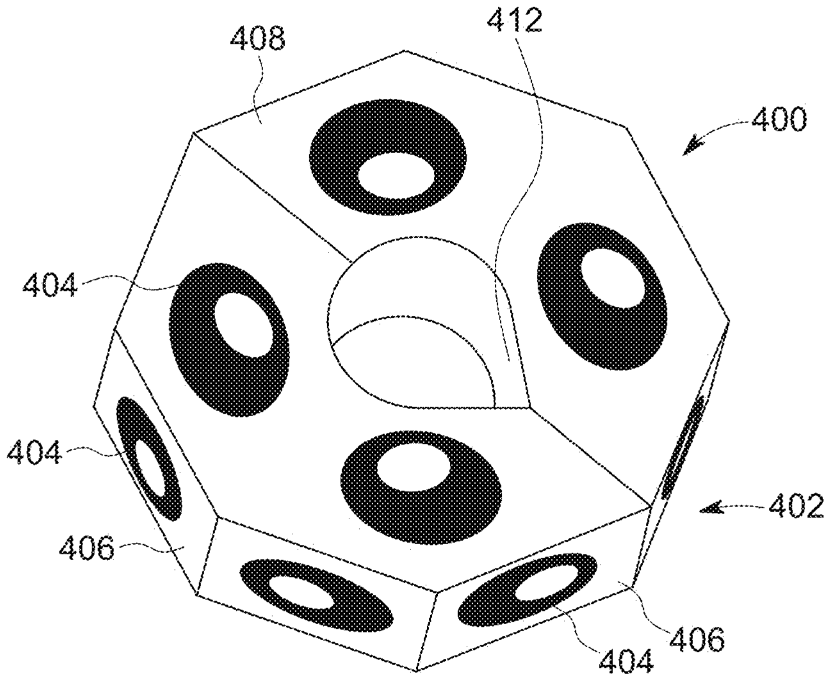
FIGS. 8I-8O show perspective views of various embodiments of directional navigation modules (DNM's), according to embodiments of the present invention.

FIGS. 8I-8O show perspective views of various embodiments of DNM's 400, according to embodiments of the present invention. DNM 400 in FIG. 8I comprises a shell 402 having an octagonal shape in cross-section such that it has eight faces 406. Each face 406 has a pattern-based marker 404 located centrally thereon. It is noted that central placement of the markers 404 on the faces 406 in this and all other embodiments shown presents uniformity for location and orientation calculations, but that such placement is not absolutely necessary. In any of these embodiments, markers 404 could be placed in offset locations and need not even be uniformly placed, relative to each respective face 406, as long as the spatial relationship between each marker 404 and respective face 406 is known and programmed into the navigation software. DNM 400 in FIG. 8I also includes an asymmetric element or key 412 that is configured to mate in a keying fashion with a shaft or instrument element that DNM 400 is mounted on, so that the rotational orientation about the shaft or instrument element is known as the DNM can be fitted on the shaft or instrument element in only one specific orientation relative to a 360-degree circumference about the shaft of instrument element. Thus DNM 400 can be positioned only in one specific, radial position/orientation about a cross-section of the shaft or instrument element. Markers 404 in FIG. 8I are eccentric ellipses where for each face the vectors 404*e*, defined as the vector originating from the center of the outer ellipse to the center of the inner ellipse, directions and/or norms are different.

Figure 8J:
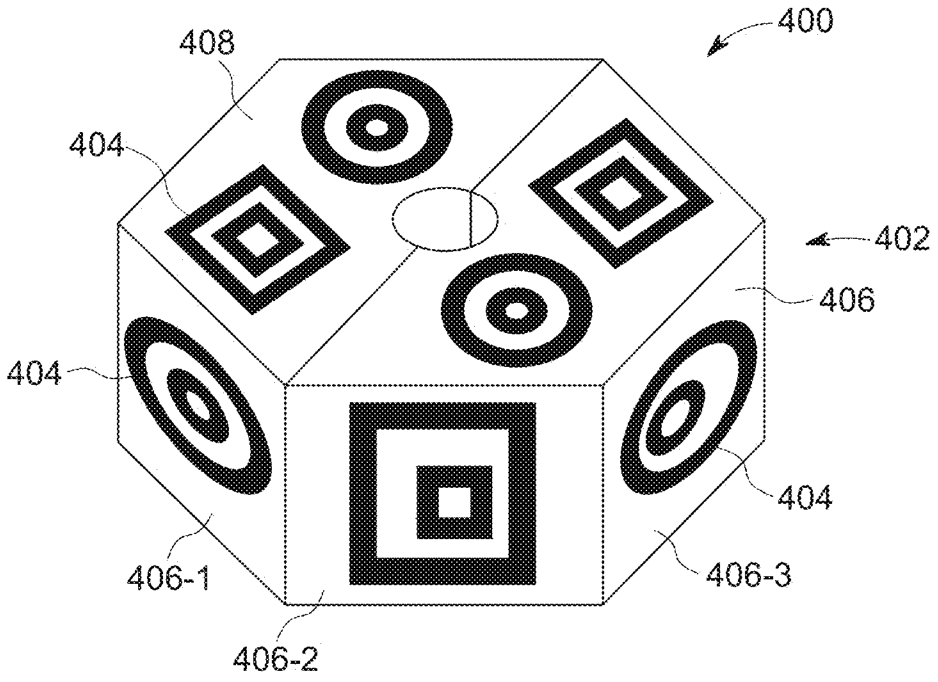

DNM 400 in FIG. 8J comprises a shell 402 having a hexagonal shape in cross-section such that it has six faces 406. Each face 406 has a different pattern-based marker 404 located centrally thereon. Markers 404 in FIG. 8J include, concentric ellipses on face 406-1, eccentric squares with a specific vector 404*e*-1 on face 406-2, and eccentric ellipses with a specific vector 404*e*-2 (different from vector 404-*e*1) on face 406-3. Faces 406-4, 406-5, and 406-6 (not shown) also have differently defined patterns 404. Additionally, face 408 has markers 404 alternating concentric circles with concentric squares.

Figure 8K:
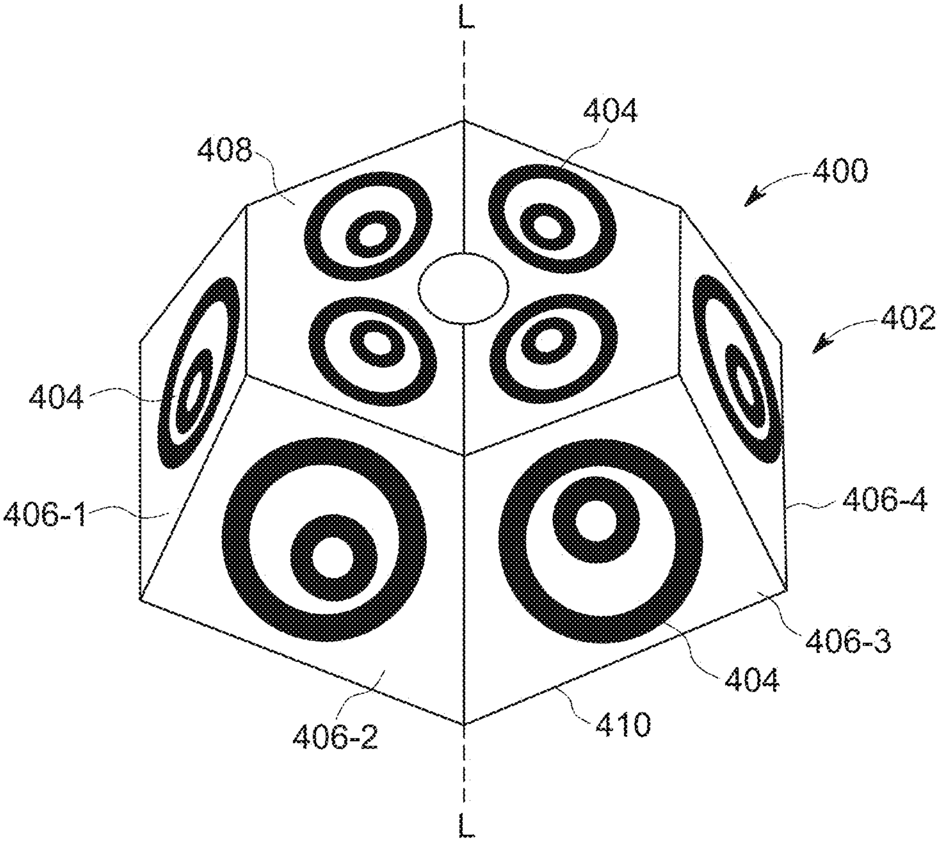

DNM 400 in FIG. 8K comprises a shell 402 having a hexagonal shape in cross-section such that it has six faces 406. The overall shape of shell 402 is a hexagonal frustum. This shape results in the faces 406 to be along planes that are angled toward the longitudinal axis L-L in a direction from the bottom 410 to the top 408 of the shell 402, in contrast with the embodiments of FIGS. 8I-8J, the faces 406 of which are parallel to the respective longitudinal axes of the shells 402. The arrangement of FIG. 8K increases (relative to the embodiments of FIGS. 8I-8J) the ranges of angles about which the markers 400 are visible to the camera system 300 when the DNM 400 is in use. Markers 404 are eccentric circles with different vectors 404*e* on each face 406. The top 408 has four markers 404 having eccentric ellipses with different vectors 404*e*.

Figure 8L:
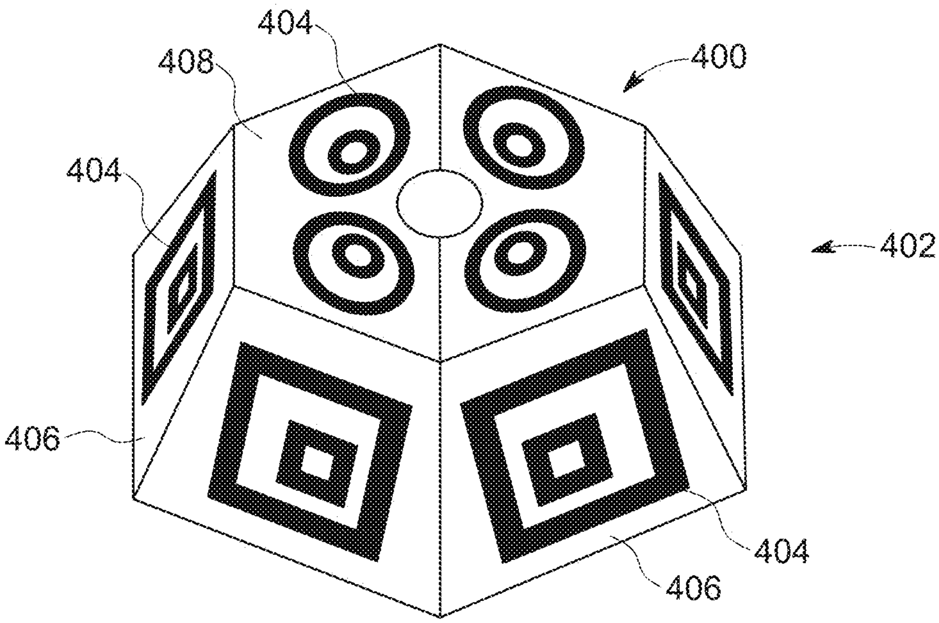

DNM 400 in FIG. 8L comprises a shell 402 having a hexagonal shape in cross-section such that it has six faces 406. The overall shape of shell 402 is a hexagonal frustum, like that of FIG. 8K. Markers 404 on the side faces 406 are eccentric squares each with a different vector 404*e* on each face 406. The top 408 has four markers 404 having eccentric ellipses with different vectors 404*e*. For each marker, the concentric shapes each have a constant thickness equal to one another.

Figure 8M:
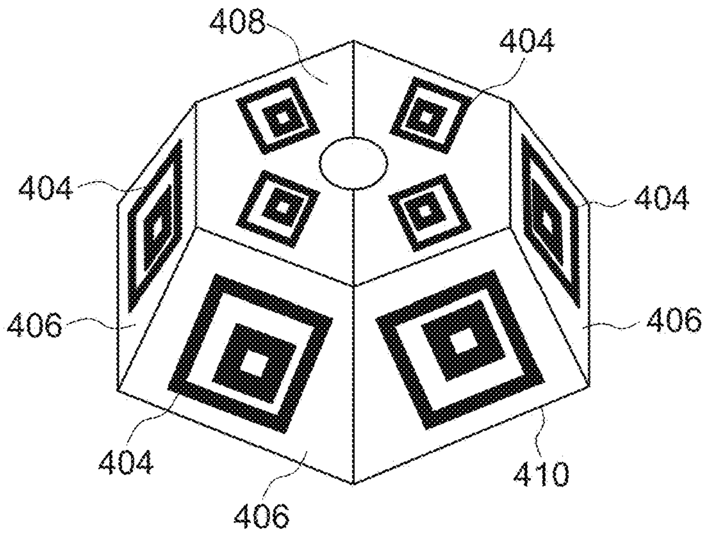

DNM 400 in FIG. 8M comprises a shell 402 having a hexagonal shape in cross-section such that it has six faces 406. The overall shape of shell 402 is a hexagonal frustum, like that of FIG. 8K. Markers 404 on the side faces 406 are eccentric squares with different vectors 404*e* on each face 406. The top 408 has four markers 404 having eccentric squares with each having a different vector 404*e*. The thickness of the outer square 404*a* is less than that of the inner square 404*b* on each of markers 404 in FIG. 8M.

Figure 8N:
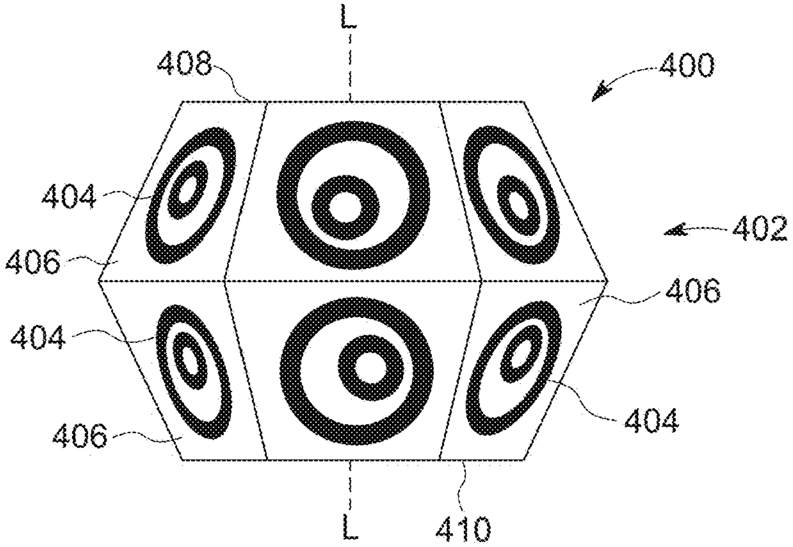

DNM 400 in FIG. 8N comprises a shell 402 having a hexagonal shape in cross-section. The overall shape of shell 402 is a hexagonal double frustum, such that the shell 402 has twelve faces 406. The six upper faces 406 are oriented in planes that are angled toward the longitudinal axis L-L in a direction from the bottom 410 to the top 408 of the shell 402, while the lower faces 406 are oriented in planes that are angled away from the longitudinal axis L-L in a direction from the bottom 410 to the top 408 of the shell 402. The arrangement of FIG. 8N increases the ranges of angles about which the markers 400 are visible to the camera system 300 even more than that provided by the embodiment of FIG. 8K. Markers 404 are eccentric circles with constant thickness and with each of the circles having equal thicknesses. Markers 404 on each of the twelve faces have a different vector 404*e* from that of the others. The top 408 and the bottom 410 also have markers 404 (not shown I FIG. 8N) similar to the markers on the faces 406.

Figure 8O:
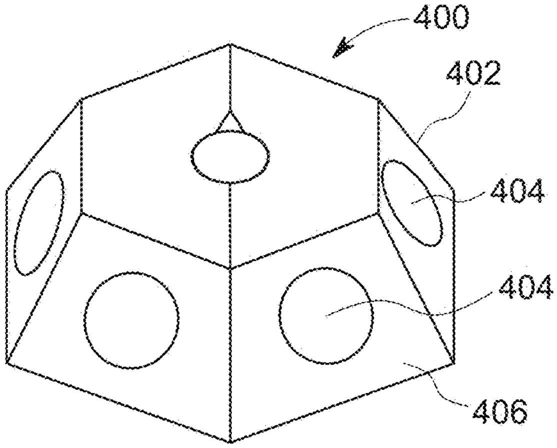

DNM 400 in FIG. 8O comprises a shell 402 having a hexagonal shape in cross-section such that it has six faces 406, like that of the embodiment of FIG. 8K. Markers 404 are retroreflective disks.

Figure 9A:
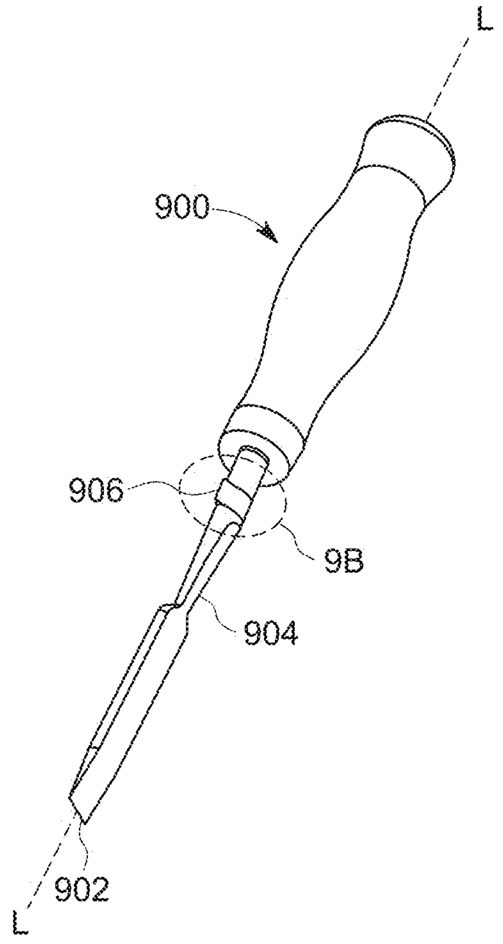
FIG. 9A is a perspective view of a surgical instrument having an asymmetric instrument tip at its distal end, according to an embodiment of the present invention.
Figure 9B:
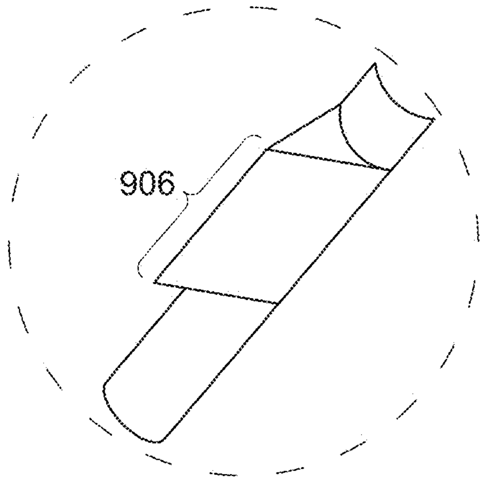
FIG. 9B is an enlarged, detailed view of the portion of FIG. 9A included within circle 9B.

FIG. 9A is a perspective view of a surgical instrument 900 having an asymmetric instrument tip 902 at its distal end. The asymmetric instrument tip is asymmetric relative to all radial directions normal to the longitudinal axis of the shaft 904 of the instrument. As such it is useful to know the relative rotational orientation of the tip 902. By providing a ridge 906 (see detailed inset of FIG. 9B) that has a known rotational orientation relative to the shaft 904, a DNM 400 having a groove or mating feature 412 like shown in FIG. 8I can be mounted to instrument 900 over shaft 904 so that the groove 412 receives ridge 906 and keys DNM 400 to tool 900 in a known rotational orientation relative to the shaft 904 and tip 902 of the instrument 900. In this case, it is ridge 906 that is radially aligned with the instrument edge 902, but it need not be, as any known relationship between the orientations of 906 and 902 will allow the calculation of the orientation of the tip 902, including its relative rotational position about the longitudinal axis L-L. In this way, the user can rely upon the tracking and registration system 100 to calculate and display the position and orientation of tip 902, even in minimally invasive procedures where the tip 902 is not visible to the user or the camera system 300, as the camera system can track the position and orientation of DNM 400

Figure 10A:
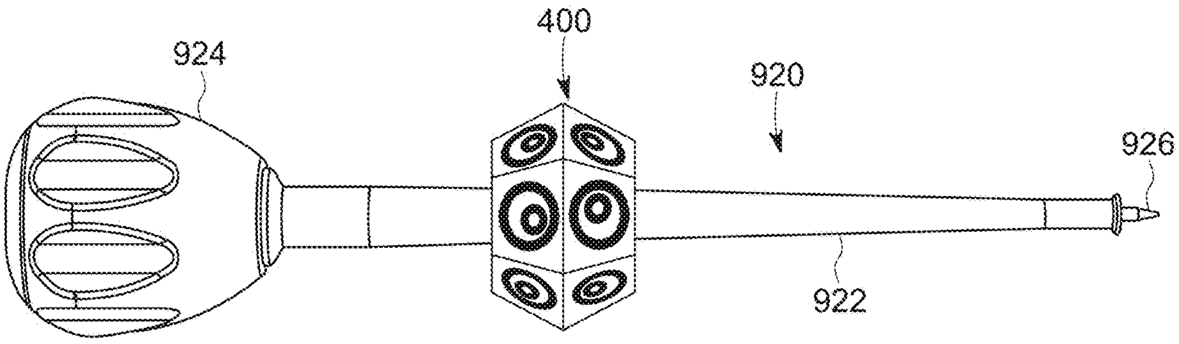
FIG. 10A is a plan view of a surgical instrument having a DNM mounted on a shaft thereof, according to an embodiment of the present invention.

FIG. 10A is a plan view of a surgical instrument 920 having a DNM mounted on a shaft 922 thereof. A handle 924 is provided at the proximal end of instrument shaft 922 of the instrument 920 for manual manipulation of the instrument by a user. Using the camera system 300 to visualize markers on the DNM 400, as well as position and orientation data received from the IMU 700 within the DNM 400, the position and orientation of the distal tip 926 of the instrument 920 can be calculated and displayed.

Figure 10B:
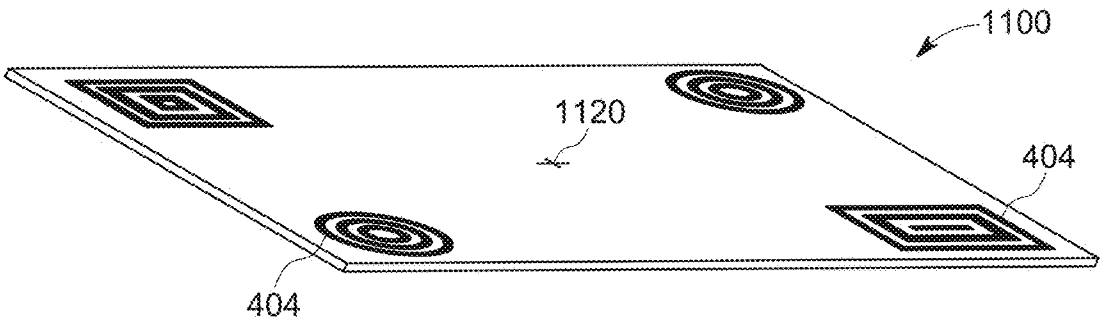
FIG. 10B. illustrates a registration block having a dimple and markers, according to an embodiment of the present invention.

FIG. 10B illustrates a registration block 1100 having a dimple 1120 and markers 404 thereon. Registration block 1100 can be used to check instrument registration (i.e., the distance between the tip 926 of the instrument 920 and the DNM 400) or to register an instrument if the DNM 400 is affixed to an instrument for which the distance from the DNM 400 to the tip of the instrument waws not preconfigured in the navigation software. In this case, once the DNM 400 is affixed to the instrument shaft, the tip of the instrument is placed into the dimple 1120 of the registration block 1100, and the computer system 200, using the camera system 300, the markers 404 on the DNM 400, IMU data and the markers 404 on the registration block 1100, calculates the distance from the DNM 400 to the tip of the instrument.

Figure 11:
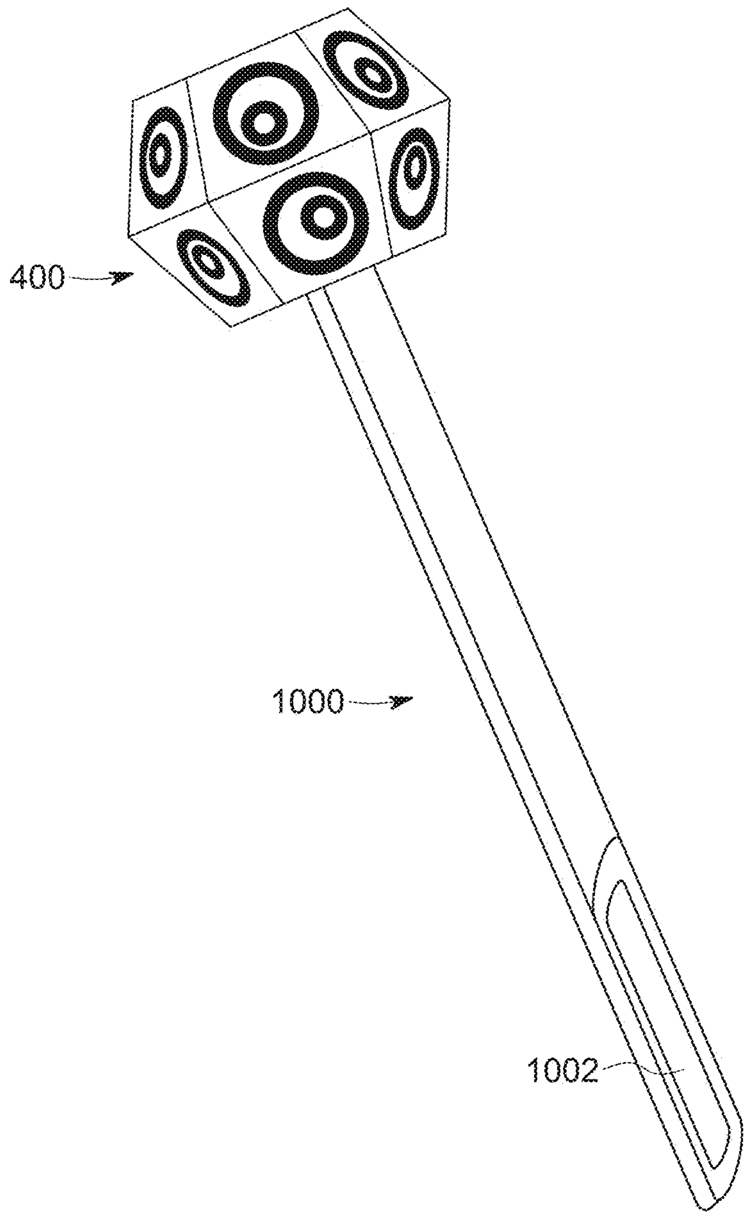
FIG. 11 is a perspective view of a DNM attached to a micro ultrasound transducer instrument, according to an embodiment of the present invention.

FIG. 11 is a perspective view of a DNM 400 attached to a micro ultrasound transducer instrument 1000, according to an embodiment of the present invention. Transducer 1002 is located at a distal end portion of the instrument 1000. The position and orientation of transducer 1002 can be calculated and displayed (numerically and/or visually) using the camera system 300 to visualize markers on the DNM 400, as well and position and orientation data received from the IMU 700 within the DNM 400, such as during an ultrasound sweep performed subcutaneously during an MIS procedure on the spine, as disclosed in more detail below.

A general description of surgical navigation and tracking that is performed during a spinal surgery procedure includes by attaching a DNM 400 in a defined location to each tool or instrument (e.g., 900, 920, 100, or other tool or instrument) be navigated and attaching a DNM 400 to a reference frame 600 (see FIG. 1). The DNMs 400 are associated in the navigation software of computing system 200 with corresponding instruments from a pre-configured list of instruments which may be stored in storage 212, for example. Alternatively, an instrument could be registered using a registration block 1100 with a dimple 1120, as described above.

Each DNM 400 constantly communicates the orientation and absolute direction of the instrument that is attached to using wireless communication (such as BLUETOOTH BLER or similar wireless communication technology) to the computing system 200 navigation software.

Patient registration is next performed. The method of registration is different depending on whether the surgical procedure is an open procedure or a minimally-invasive (MIS) procedure. For an MIS procedure, patient registration is performed without radiation, using a preoperative scan (preferably, but not necessarily a CT scan) and intraoperative ultrasound scanning, as will be described in more detail below. Using pattern-based markers or retro-reflective surface markers on the DNM 400, the camera system 300 and the computing system 200/navigation software compute the location of the instrument tip of an instrument that is being tracked/navigated, in relation to the location of the reference frame 600 and the patient 1.

Using algorithm 610, the navigation software determines the location, orientation, and direction of the instrument tip in relation to the patient anatomy. Using the positioning of the DNM 400 in relation to the instrument 90/92/1000 and the yaw/heading information from the DNM 400, the computing system 200, executing the navigation software, overlays the instrument model in the 3D view of the patient anatomy on display 210. The IMU 700 integrated in the DNM 400 communicates to the computer system 200 the orientation and absolute direction in the form of a quaternion. From this, the computer system 200 extracts the corresponding pitch, roll and yaw. The yaw is often called the heading and is the rotation angle around the Z axis of the IMU 700.

The user selects a screw type and size to be used for insertion into a pedicle, and the system 200 overlays and tracks a navigated driver instrument and the screw 70 as the screw 70 is inserted into the pedicle. The screws 70 are navigated and once the screws 70 are inserted, the computing system 200 overlays a screw model on top of the patient anatomy on display 210. The computing system 200 saves the position and the orientation of each screw 70 after its placement.

The navigation caps 800 are attached to the screw heads 72 or tabs 74 extending therefrom, prior to implanting the screws 70. In this way, navigation caps 800 can be used to track the advancement of the screws 70 into the vertebrae. The computer system 200 using the data from the camera system 300 and from IMUs 700 integrated in the navigation caps 800 along with the tracking algorithm 610 can track pose (orientation and position) of the screws 70 in real time (and optionally, the tracking can be based on fused tracking data from camera system and IMU without using deep learning), and can display models one or more screws at any time during the implantations. The computer system 200 can use the tracking information, in addition to the previously saved locations and orientations of the screws 70 to calculate the final locations and orientations of each screw 70 in relation to the other screws and calculate the needed rod length, the needed reduction and the coronal bends at each screw level, and use this information to create a rod bending template for a custom rod to be used and secured in place using set screws 875, at the locations after reductions having been carried out.

Figure 12:
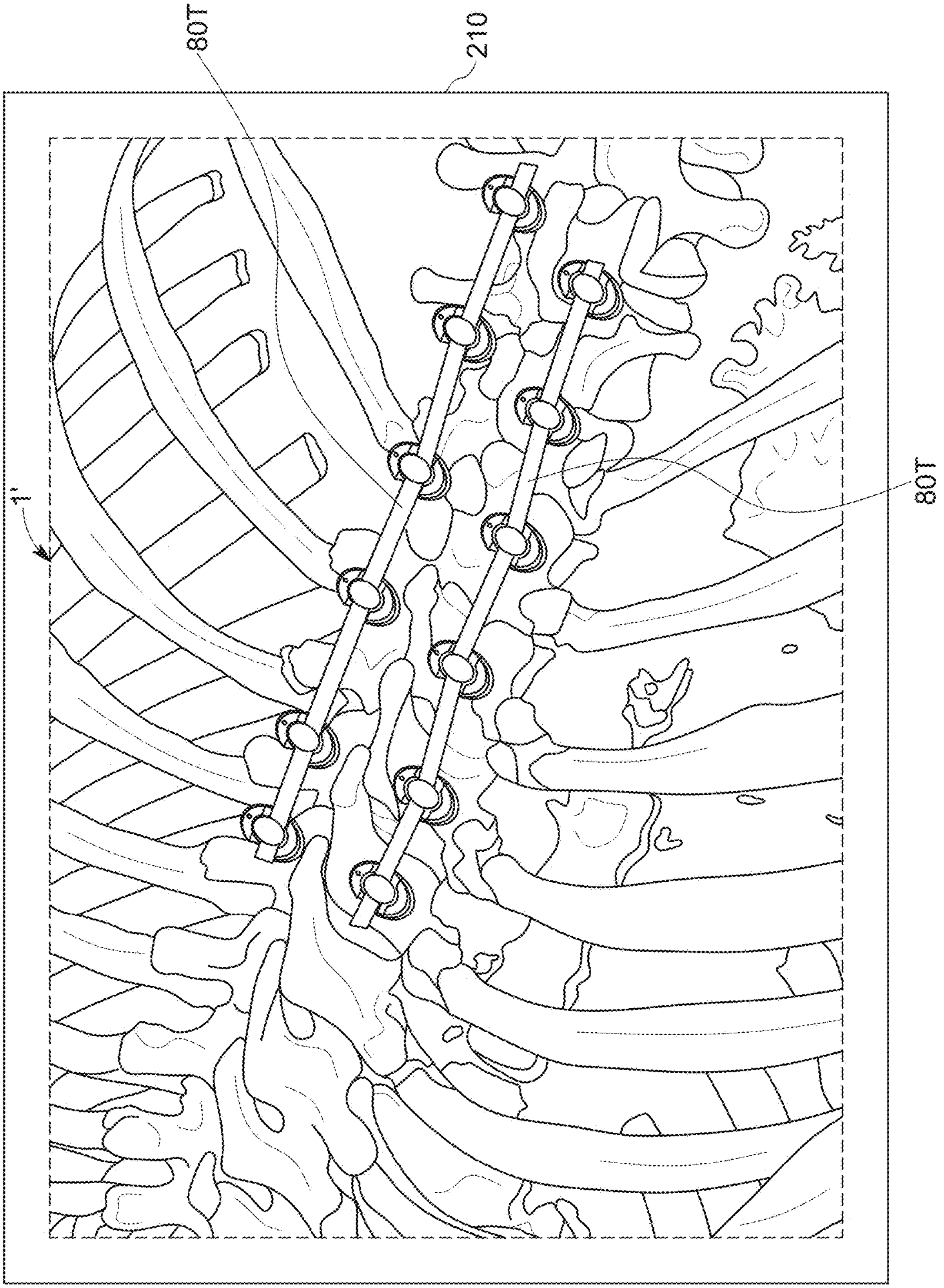
FIG. 12 is a 3D view rendering of the spine of a patient from preoperative imaging, augmented with implanted screw models and rod templates, according to an embodiment of the present invention.

Rod bending templates can be communicated to a tablet or other computing device as 1:1 model for manual bending or can be communicated directly for automated bending, such as by direct communication to a computer numerical control (CNC) rod-bending machine. FIG. 12 is a 3D view rendering of the spine of the patient 1' from preoperative imaging, augmented with implanted screw models and rod templates models, according to an embodiment of the present invention.

Figure 13A:
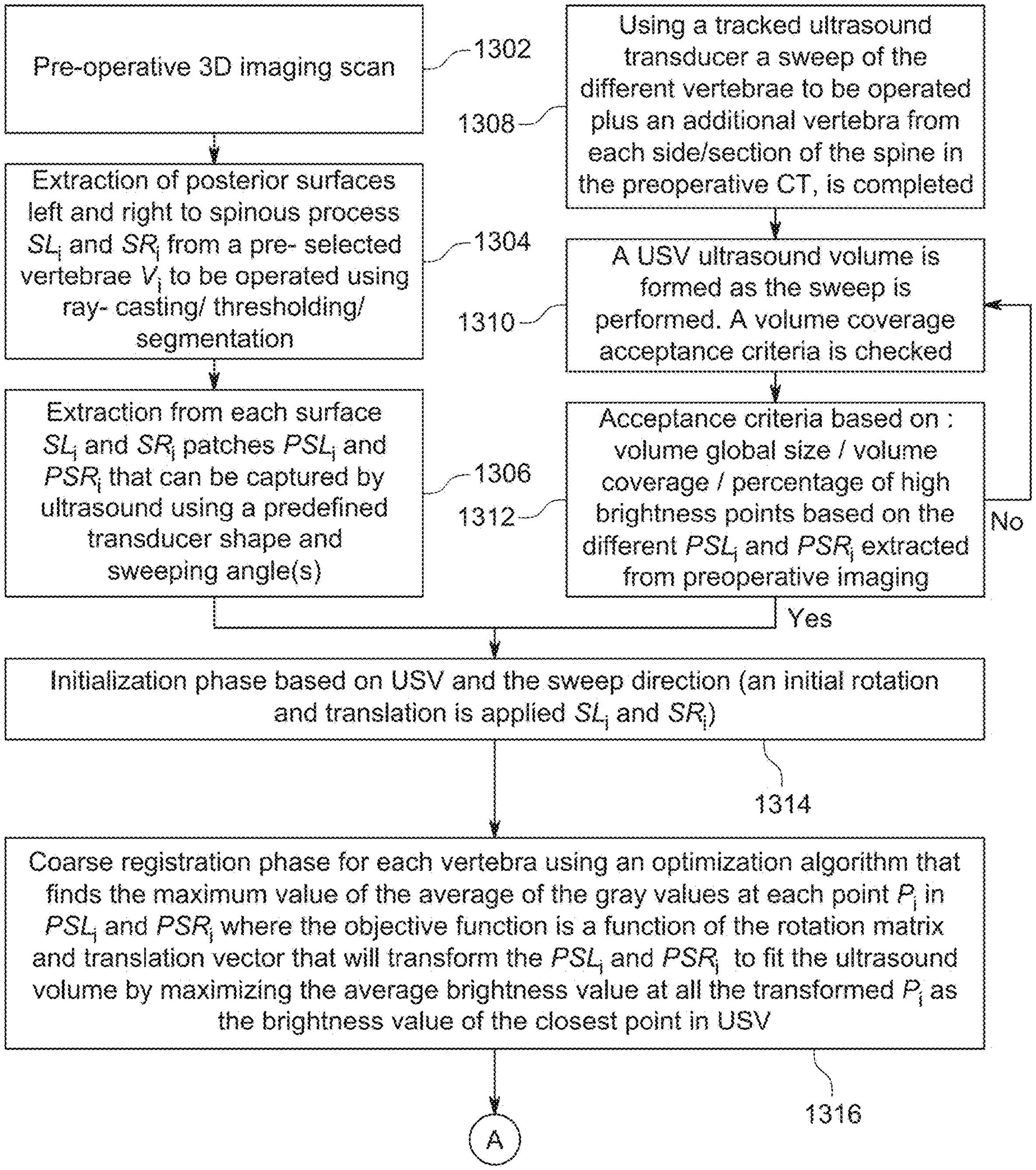
FIGS. 13A-13B show a flowchart illustrating events that may be carried out for registering a patient for an MIS surgical procedure on the spine, according to an embodiment of the present invention.
Figure 13B:
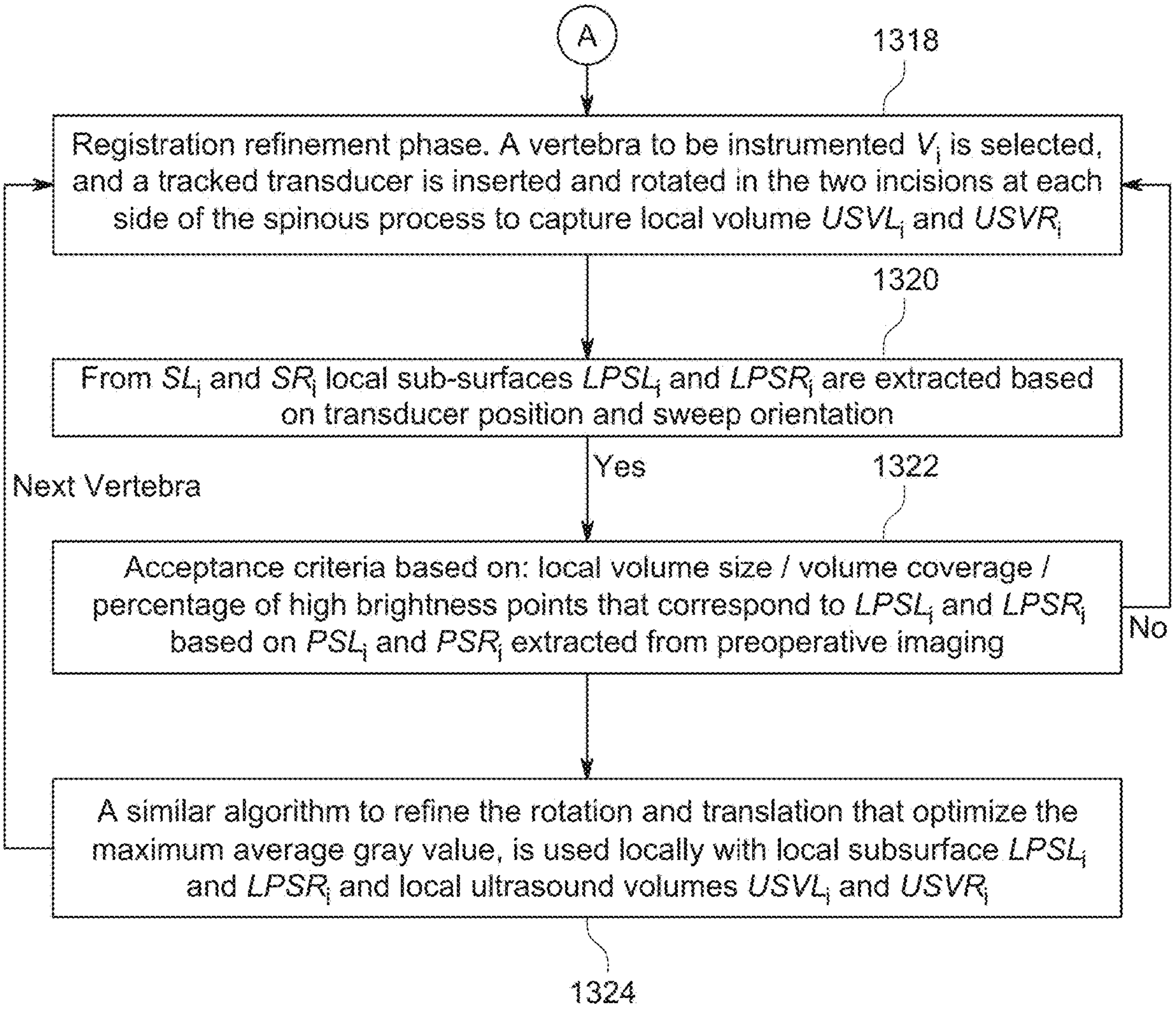

FIGS. 13A-13B show a flowchart illustrating events that may be carried out for registering a patient for an MIS surgical procedure on the spine, according to an embodiment of the present invention. At event 1302 preoperative image data of the spine 2 is obtained as a reference to which intraoperative images of the spine 2 will be registered. As noted previously CT scan images are preferred, but other alternatives could be used.

Figure 14B:
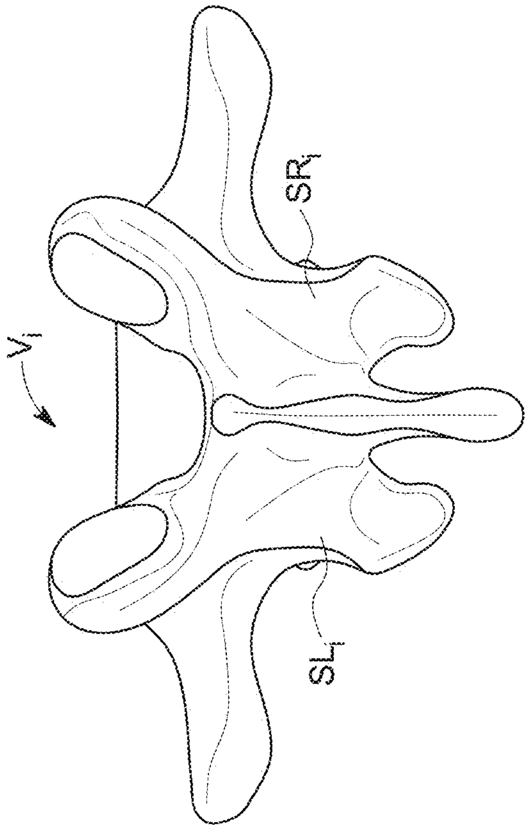
FIG. 14B identifies the left posterior surface $SL_i$ and the right posterior surface $SR_i$ extracted from the vertebra of FIG. 14A, according to an embodiment of the present invention.
Figure 14A:
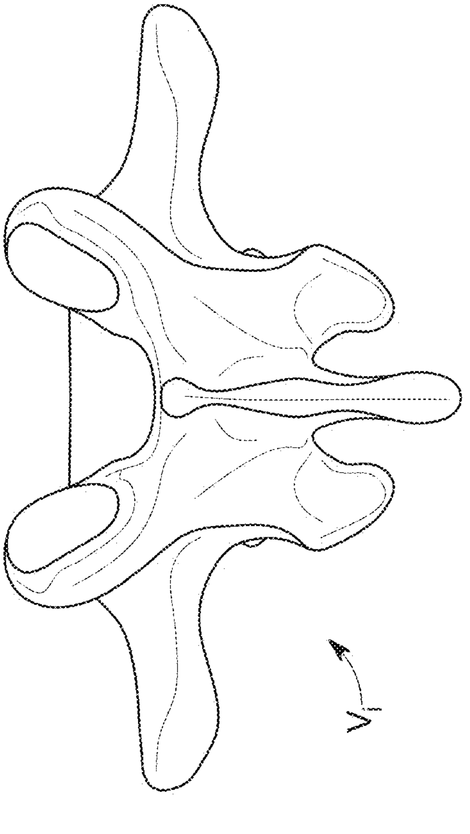
FIG. 14A illustrates an example a prelected vertebra imaged by a preoperative CT scan, according to an embodiment of the present invention.

At event 1304 images of posterior surfaces left and right of spinal processes of the spine are iteratively extracted as $SL_i$ and $SR_i$ from prelected vertebrae $V_i$ respectively, using known techniques such as ray-casting/thresholding/segmentation, etc., where i=1, 2 . . . n and n is the number of vertebrae/spinal processes in the target area to be operated on. FIG. 14A illustrates an example one of the prelected vertebrae $V_i$ imaged by a preoperative CT scan. FIG. 14B identifies the left posterior surface $SL_i$ and the right posterior surface $SR_i$ extracted from the vertebra $V_i$.

Figure 15B:
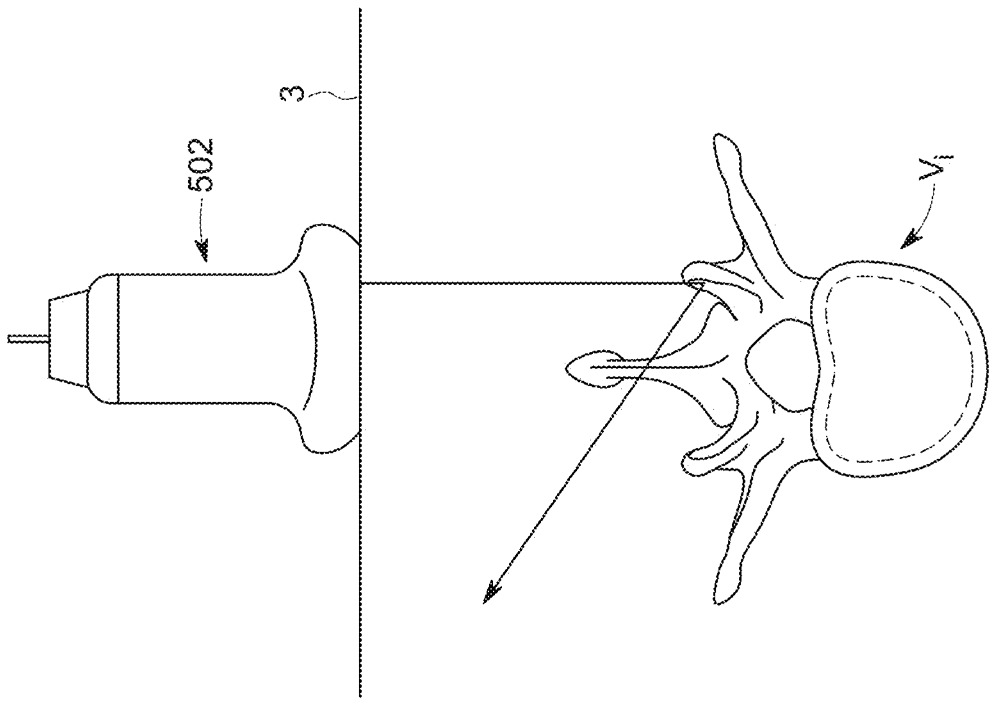
FIGS. 15A-15B illustrate a process of determining if a point from $SL_i$ is in the patch $PSL_i$, based on the ultrasound transducer location, orientation, and geometry, the specular property of ultrasound wave, and the topology of the surface $SL_i$ around the selected point, according to an embodiment of the present invention.
Figure 15A:
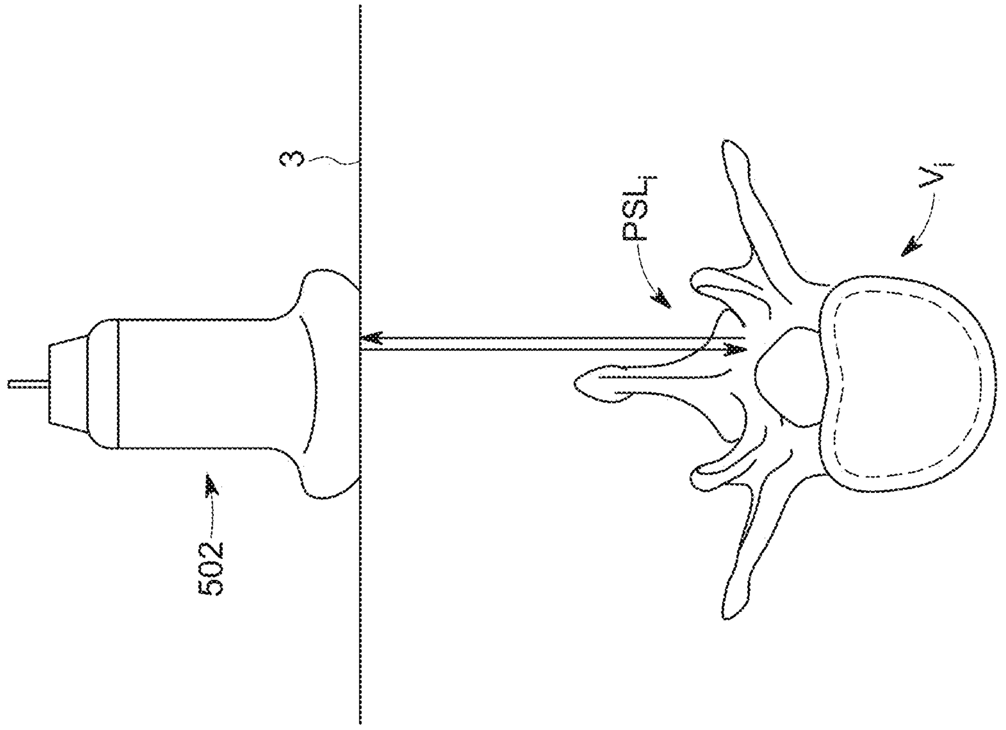

From each surface $SL_i$ and $SR_i$, patches $PSL_i$ and $PSR_i$ are extracted at event 1306, based on an algorithm that uses the known ultrasound shape, the theoretically possible sweeping path and angles, specular property of ultrasound wave, and the topology of the surface $SL_i$ around each point, to determine whether a point can theoretically be captured or not. FIGS. 15A-15B illustrate a process of extracting patch $PSL_i$ using ultrasound transducer 502, like what was previously described with regard to FIG. 1. Note that the algorithm presupposes that ultrasound transducer 502 is swept over the patient 1 from an external location, i.e., outside of the skin 3 and swept over the skin 3 of the patient 1. FIG. 15A illustrates that an ultrasound image point is captured when the target surface being captured is substantially normal to the direction of the ultrasound wave directed to the target surface, so that the reflected wave is directed back to the ultrasound transducer 502, while FIG. 15B shows that when the target surface is angled, relative to the normal to the direction of the ultrasound wave directed to the target surface, the reflected wave angles away from the directed wave and is not received by the transducer 502.

Based on the preoperative scan and user input about the levels (i.e., vertebrae) to be instrumented, a global volume to be covered with the ultrasound sweep is calculated. Also, based on the different $PSL_i$ and $PSR_i$ a percentage of bright point from global volume is calculated. The ultrasound transducer 502 is not involved at event 1306. $PSL_i$ and $PSR_i$ are extracted based on an algorithm that uses the known ultrasound shape and the possible sweeping path and angles, to determine whether a point P on $SL_i$ or $SR_i$ can theoretically be captured or not, based on the topology of vertebrae in the neighborhood of the point P and the specular property of the ultrasound waves when encountering two media with different acoustic impedances (i.e., soft tissue and bone). The possible sweeping angles are based on the theoretically possible level of pressure that can be applied without losing contact with the skin of the patient 1 (a few degrees around the vertical).

As the ultrasound sweep is performed a volume is formed and its size, coverage, and percentage of bright points are calculated and compared to the theoretical information precalculated from the preoperative scan and user input. The acceptance level is defined and the user is alerted once the acceptance level has been reached.

The tracked ultrasound transducer 502 is used to sweep at least the vertebrae $V_i$ to be operated on plus an additional vertebra from each end immediately adjacent to the vertebra $V_i$ at event 1308. FIG. 1 illustrates this event being carried out. The user performing the sweep may need to tilt the transducer 502 while maintaining skin contact within the possible orientations based on the pressure that can be applied to be able to reach the acceptance criteria of high brightness percentage. As the sweep is performed, an ultrasound volume (USV) of the vertebrae being swept is formed at event 1310. Volume coverage criteria are checked at event 1312. Volume coverage criteria are based on volume global size, volume coverage of the vertebrae $V_i$, and/or percentage of high brightness points that correspond to the $PSL_i$ and $PSR_i$ extracted from the preoperative scan. The theoretical $PSL_i$ and $PSR_i$ are compared to the high brightness points in the formed USV. If the acceptance criteria are not met at event 1312, then the ultrasound sweep and formation of USV are repeated at event 1310 and events 1310 and 1312 are iterated until acceptance criteria are met.

Once acceptance criteria of the current USV have been met, an initialization phase is carried out at event 1314, where an initial rotation and translation are applied to $SL_i$ and $SR_i$, wherein the initial rotation and translation values are calculated from values in the USV and sweep direction. An initial rotation and translation is applied to the whole volume of the preoperative CT scan from which $SL_i$ and $SR_i$ are extracted. Next, a coarse registration phase is carried out at event 1316. Coarse registration is performed for each of the vertebrae $V_i$ using an optimization algorithm that finds the maximum value of the average of the gray values at each point $P_j$ in $PSL_i$ and $PSR_i$, where the objective function of the optimization algorithm is a function of the rotation matrix and translation vector that will transform the $PSL_i$ and $PSR_i$ to fit the ultrasound volume (USV) by maximizing the average brightness values at all of the transformed $P_j$ as the brightness values of the closest points thereto in the USV.

For each vertebra $V_i$, the coarse registration phase is based on the following optimization problem: finding the maximum value of the average brightness values at each transformed point $P_j$: where $P_j \in PSL_i$ with $N_i$ points and $P_j \in PSR_i$ with $M_i$ points, and $$P_j \in PSL_i \text{ with } N_i \text{ points and } P_j \in PSR_i \text{ with } M_i \text{ points, and} \quad (4)$$

$$\vec{G}(\alpha, \beta, \gamma, \vec{t}) = \frac{1}{N_i}\sum_{j=1}^{N_i} B(T(P_j)) + \frac{1}{M_i}\sum_{j=1}^{M_i} B(T(P_j))$$

where T is the transformation that represents the full rotation and translation in 3D space using Euler angles ($\alpha$, $\beta$, $\gamma$) and the translation vector $\vec{t}(t_x,t_y,t_z)$; and where B is the brightness value at $T(P_j)$ and defined as the brightness value of the closest point to $T(P_j)$ in the ultrasound volume USV, and G is a function of the Transformation T (Translation+Rotation) as described in the formula (4), it represents the average brightness for $PSL_i$ and $PSR_i$ as the transformation T changes. Maximizing G will allow finding the optimal transformation that will achieve the coarse registration.

Figure 16:
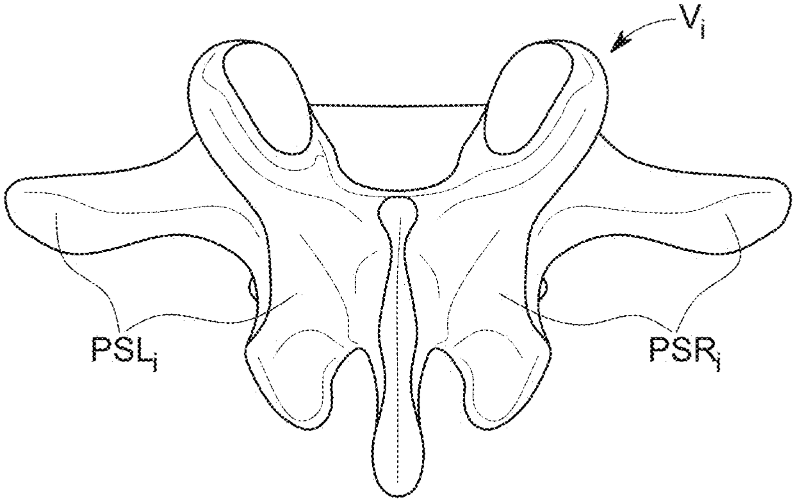
FIG. 16 illustrates vertebra Vi with left posterior surfaces $PSL_i$ and right posterior surfaces $PSR_i$ that are extracted from $SL_i$ and $SR_i$, based on an algorithm, that uses the known ultrasound geometry, the theoretically possible sweeping path and angles, the specular property of ultrasound wave, and the topology of the surface around each point, according to an embodiment of the present invention.
Figure 17:
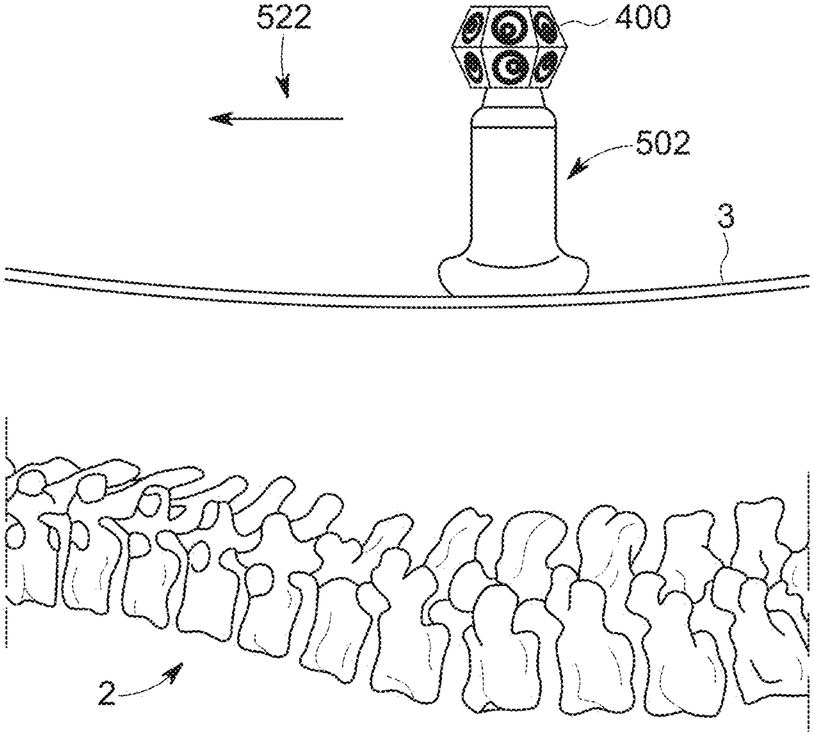
FIG. 17 illustrates a sweep with a tracked ultrasound transducer along a predefined sweep path, according to an embodiment of the present invention.
Figure 18:
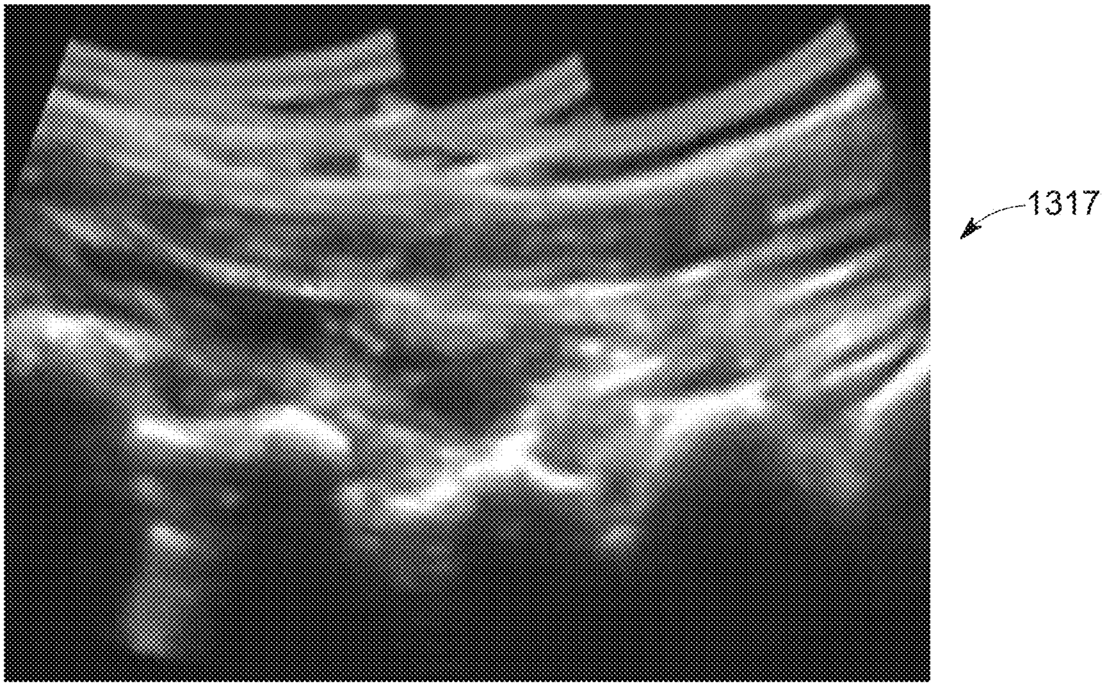
FIG. 18 shows multiple ultrasound 2d captures having been stacked together with assistance of tracking information provided by tracking with tracked ultrasound transducer and DNM to provide USV, according to an embodiment of the present invention.
Figure 19:
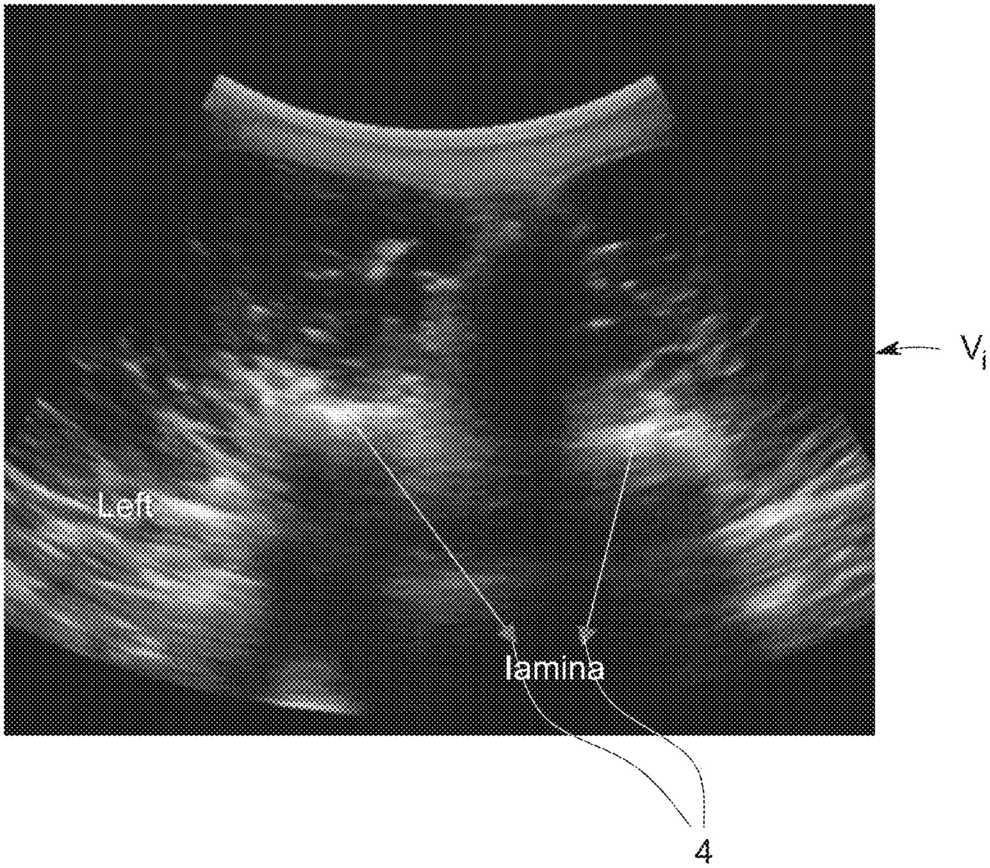
FIG. 19 illustrates that interfaces between soft tissue and bone show up with high brightness on an ultrasound capture according to an embodiment of the present invention.

FIG. 16 illustrates vertebra Vi with left posterior surfaces $PSL_i$ and right posterior surfaces $PSR_i$ that are extracted from $SL_i$ and $SR_i$ based on transducer 502 geometry and predefined sweep path 522 and orientation of the transducer 502. As noted above, this sweep is performed external of the skin, and thus can be performed before any incision is made through the skin 3. FIG. 17 illustrates a sweep with a tracked ultrasound transducer (tracking facilitated by DNM 400 as described previously) along a predefined sweep path. The ultrasound volume (USV) can be formed from staking of the tracked 2D (i.e., two-dimensional) ultrasound captures of slices of $V_i$ to enable the initial and coarse registration phases 1314 and 1316. FIG. 18 shows multiple ultrasound 2d captures having been stacked together with assistance of tracking information provided by tracking with tracked ultrasound transducer 502 and DNM 400 to provide USV 1317. FIG. 19 illustrates that interfaces between soft tissue and bone show up with high brightness on an ultrasound capture. Particularly bright points are noted where soft tissue interfaces with lamina 4 of a vertebra $V_i$ in the capture.

Upon completion of the coarse registration phase at event 1316, a registration refinement phase can next be carried out at event 1318. For each vertebra $V_i$ an incision is performed on each side of the spinous process and a tracked ultrasound transducer instrument 1000 is used to capture local ultrasound volumes $USVL_i$ and $USVR_i$ Based on the location of the tracked ultrasound transducer instrument 1000 and the level to be instrumented, a local volume to be covered with the ultrasound sweep is calculated. Also, using a similar algorithm that was used to extract $PSL_i$ and $PSR_i$ from $SL_i$ and $SR_i$, and initial location of the transducer 1002 of instrument 1000, local surfaces from potentially possible points to be captured by the local sweep are extracted $LPSL_i$ and $LPSR_i$ at event 1320.

As the ultrasound sweep is performed a volume is formed and its size, coverage, and percentage of bright points are calculated and compared to the theoretical information precalculated from the preoperative scan for the selected level. The acceptance level is predefined and the user is alerted once the acceptance level has been reached.

Figures 20A, 20B:
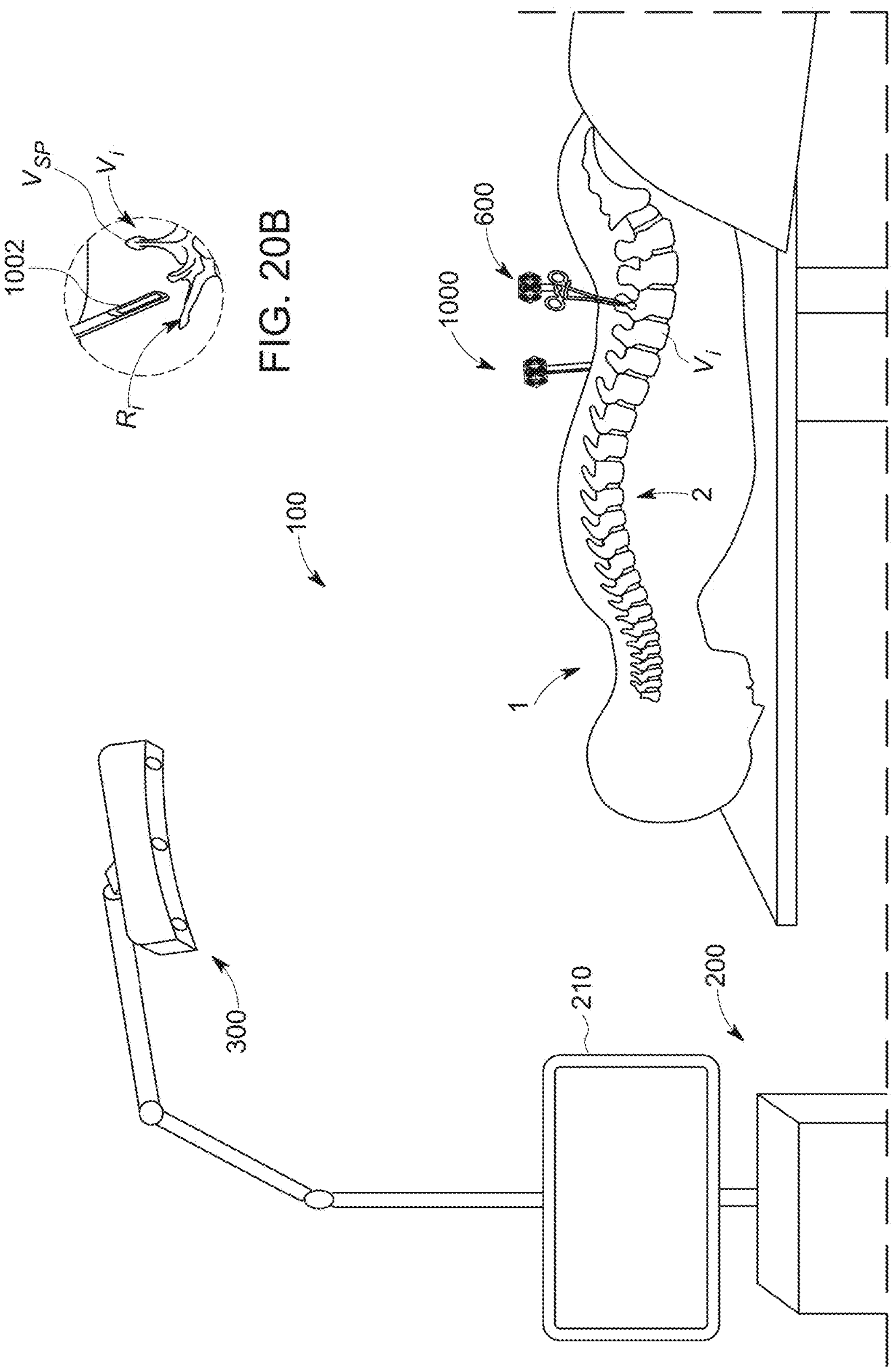
FIG. 20A illustrates an ultrasound transducer being used in an MIS procedure to perform registration refinement, according to an embodiment of the present invention.
FIG. 20B is an enlarged partial view of FIG. 20A that shows the ultrasound transducer having been inserted into the patient, according to an embodiment of the present invention.

For each of the vertebra $V_i$ to be instrumented (where instrumented, refers to a vertebra where one or more screws need to be inserted), the registration refinement is carried out at an individual level. Thus, for each of $V_i$, A tracked ultrasound transducer instrument 1000 is inserted through incisions on right and left sides of the spinous process $V_{SP}$ of vertebra $V_i$, respectively, and rotated to capture local ultrasound volumes $USVL_i$ and $USVR_i$. FIG. 20A illustrates event 1318 being carried out on the right side of a selected vertebra. FIG. 20B is an enlarged partial view of FIG. 20A that shows the ultrasound transducer 1002 of the micro ultrasound transducer instrument 1000 having been inserted into the patient 1 to capture image data of the right-side Ri of the vertebra Vi to be used in calculating $USVR_i$.

At event 1322, local volume coverage criteria are checked to see if they meet acceptance criteria. Local volume acceptance criteria are based on local volume size, local volume coverage of the vertebrae $V_i$, and/or percentage of high brightness points that correspond to the $LPSL_i$ and $LPSR_i$ extracted from the preoperative scan. A theoretical local volume size is calculated based on preoperative imaging and from the tracked ultrasound a volume is formed. Dividing the ultrasound obtained volume from the sweep by the theoretical volume from preoperative imaging defines the percentage of coverage. If the acceptance criteria are not met at event 1322, then the ultrasound capture of the current vertebra $V_i$ being processed is repeated at event 1318, and events 1320 and 1322 are iterated until acceptance criteria are met for the current vertebra being processed.

Once acceptance criteria have been met at event 1322, a similar optimization algorithm to that employed in event 1316 is used to refine the rotation and translation that optimize the average gray value at event 1324, using local surfaces $LPSL_i$ and $LPSR_i$ and local ultrasound volumes $USVL_i$ and $USVR_i$, based on assisted sweep path with the micro transducer 1000 to the left and right of the spinous process of $V_i$. Other algorithms could be used in the registration refinement phase. $USVL_i$ and $USVR_i$ have a higher resolution than USV as a higher frequency is used with the micro transducer 1000 through the incisions is closer to the vertebra and captures more points from the posterior surface than the initial sweep performed for coarse registration, due to vertebrae geometry and higher resolution. More surface area of the top external surface of the vertebrae can be captured as the transducer is in a different location and closer to the parts of the surface that cannot be captured using the initial sweep because of the intricacy of vertebrae shapes and the limitation from the specular property of the ultrasound waves. The interface between bone and soft tissue can be segmented based on the brightness levels in $USVL_i$ and $USVR_i$ and a known algorithm such as Iterative Closest Point Algorithm (ICP) could be used to register $SL_i$ and $SR_i$ to the segmented ultrasound local volumes.

Upon completing the rotation and translation calculations for refining the visualization and mapping of the current vertebrae, events 1318-1324 are repeated for the next vertebra $V_i$, and this processing continues until all vertebrae $V_i$ have been processed for registration refinement. Once the registration refinement is completed the surgeon can navigate an instrument like a probe, tap, and/or driver and place screws accurately.

Figure 21A:
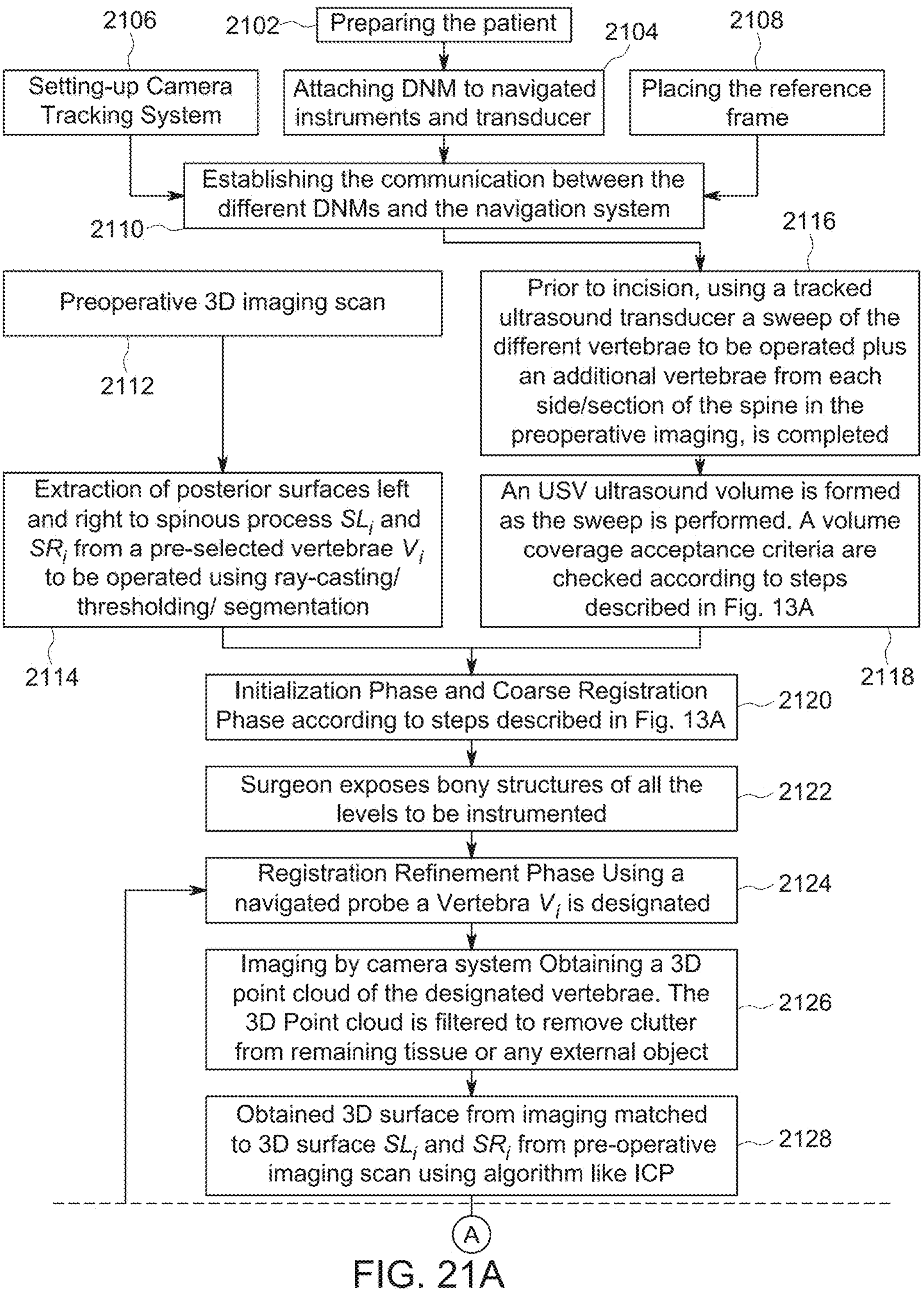
FIGS. 21A-21B show a flowchart illustrating events that may be carried out for registering a patient and tracking for an open surgical procedure on the spine, according to an embodiment of the present invention.
Figure 21B:
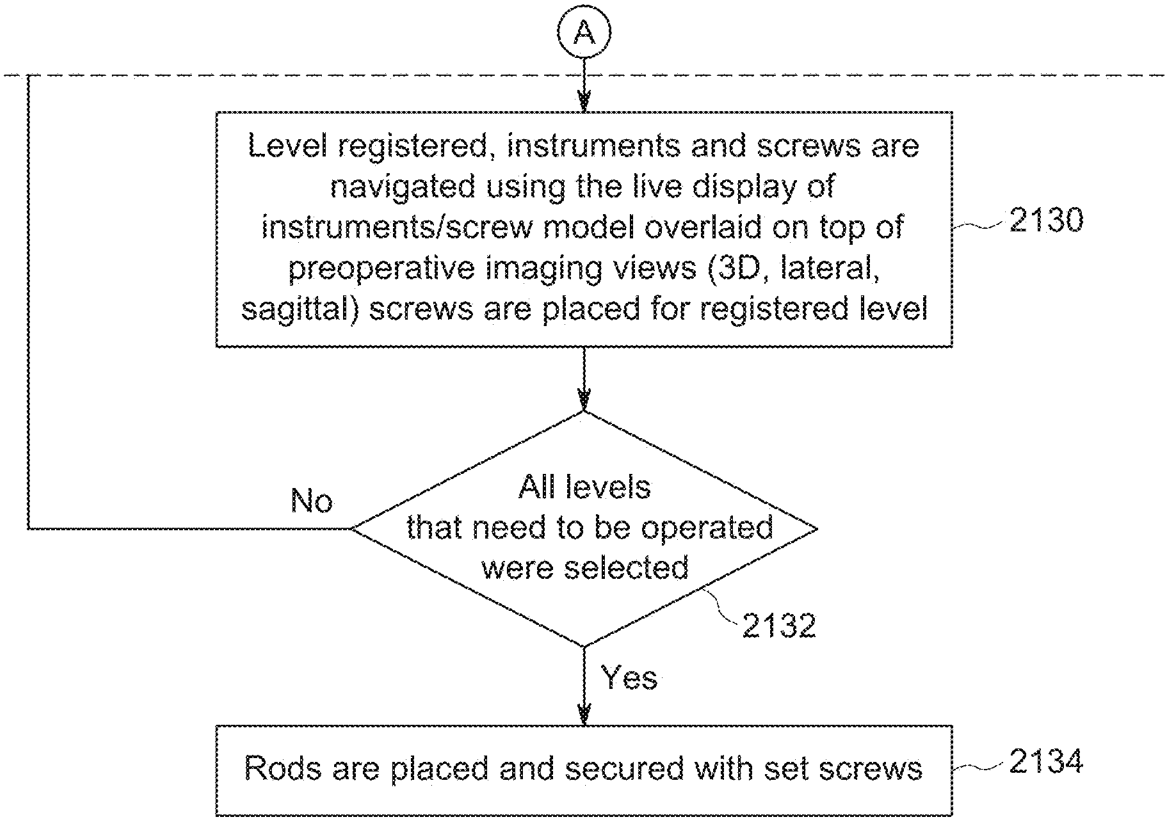

FIGS. 21A-21B show a flowchart illustrating events that may be carried out for registering a patient and tracking for an open surgical procedure on the spine, according to an embodiment of the present invention. At event 2102 (FIG. 21A) the patient 1 is prepared for the surgery, to include all events needing to be performed before the surgical procedure can start, including, but not necessarily limited to: sterilizing where appropriate, draping the patient, loading preoperative imaging to the computer system 200, etc.

At event 2104 a DNM 400 is attached to at least one instrument to be navigated during the procedure. FIG. 10A shows an example of an instrument 920 having a DNM 400 attached thereto.

At event 2106, the camera tracking system 300 is set up, including turning on the camera system 300, positioning it correctly above the patient 1, and checking the communication between the camera (tracking) system 300 and computing system 200. Reference frame 600, including DNM 400 is fixed close to the levels to be instrumented, for example, on a spinous process close to the levels to be instrumented within the viewing field of the camera system 300 at event 2108. At event 2110 communication between the DNMs 400 to be used in the procedure and the navigation system 100, including camera system 300 and computing system 200 is established.

At event 2112 preoperative image data (from a preoperative 3D imaging scan) of the spine 2 is obtained as a reference to which intraoperative images of the spine 2 will be registered. As noted previously CT scan images are preferred, but other alternatives could be used.

At event 2114, from the preoperative imaging obtained at event 2112, posterior surfaces left and right of spinal processes of the spine are iteratively extracted as $SL_i$ and $SR_i$ from prelected vertebrae $V_i$ respectively, using known techniques such as ray-casting/thresholding/segmentation, etc., where i=1, 2 . . . n and n is the number of vertebrae/spinal processes in the target area to be operated on.

Prior to incision of the patient 1 (i.e., before the skin is cut to provide access beneath it to the spine 2), tracked ultrasound transducer 502 is used at event 2116 to sweep at least the vertebrae $V_i$ to be operated on plus an additional vertebra from each end immediately adjacent to the vertebra $V_i$. As the sweep is performed, an ultrasound volume (USV) of the vertebrae being swept is formed at event 2118. Volume coverage criteria are checked at event 1312. Volume coverage acceptance criteria are based on volume global size, volume coverage of the vertebrae $V_i$, and/or percentage of high brightness points that correspond to the $PSL_i$ and $PSR_i$ extracted from the preoperative scan, as described above with regard to FIG. 13A, event 1312. The theoretical $PSL_i$ and $PSR_i$ are compared to the high brightness point in the formed USV. If the acceptance criteria are not met at event 2118, then the ultrasound sweep and formation of USV are repeated at events 2116 and 2118, and are iterated until volume coverage acceptance criteria are met.

Once acceptance criteria of the current USV have been met, an initialization phase is carried out at event 2120, where an initial rotation and translation are applied to $SL_i$ and $SR_i$, wherein the initial rotation and translation values are calculated from values in the USV and sweep direction. An initial rotation and translation is applied to the whole volume of the preoperative CT scan from which $SL_i$ and $SR_i$ are extracted, in the same manner as described above with regard to FIG. 13A, event 1314.

At event 2122 the surgeon exposes bony structures of the levels (vertebrae) of the spine that are to be instrumented. At event 2124 a registration refinement phase is initiated, during which a navigated probe (such as probe 920 shown in FIG. 10A, for example) is used to designate a vertebra $V_i$ to be registered.

At event 2126, camera system 300 is used to image the designated vertebra $V_i$ to obtain a 3D point cloud image of the designated vertebra $V_i$. As noted previously, the camera system 300 preferably uses optical cameras sensitive to visible light, although cameras sensitive to other wavelengths could be used. The 3D point cloud is filtered to remove clutter in the data caused by remining soft tissue or other objects that are not bone tissue.

Currently available systems that register a vertebra to a preoperative image using a 3D imaging system to capture a 3D point cloud, have a drawback that the whole surface of the designated vertebra posterior structure cannot be obtained since parts of the spinous process are obstructed (cannot be in the field of view of both cameras). This results in (void) patches of the 3D point cloud for the left and right side of the spinous process. An additional shortcoming of currently available systems is that, because of the similarities in the topology of the exterior surface between consecutive vertebrae, the ICP algorithm can fail in registering the 3D point cloud patches with extracted surfaces from preoperative imaging if enough points from the two surfaces cannot be matched and/or if the algorithm is stuck in what is known as local minima. Attempts at addressing these issues often result in trying to match the patches of the 3D point cloud from the designated vertebra with the extracted surface from the identified corresponding level in the preoperative imaging, but also with the levels above and below it. Also, because of the local minima issue the patches are compared (initialization phase) to the extracted surface taken from the left to the right and from the right to the left of the spinous process.

The present system overcomes these shortcomings and drawbacks by first using ultrasound coarse registration in patient registration for radiation-free open surgeries (event 2120), then using 3D camera (such as optical) imaging for registration refinement for each level (events 2124-2130). The ultrasound coarse registration streamlines the registration process as a first transformation (coarse registration) brings the preoperative imaging in the correct orientation and close enough to the different point clouds, to be captured later, before any incision and before exposing the bony structures that need to be operated on. This facilitates the robustness and fast convergence of a matching algorithm like ICP when a good initialization is provided, as made possible by the coarse registration. Because of the close advantageous initialization conditions, the issue of local minima is avoided. Also extended and/or iterations of exposure procedures of bony structures is minimized, as the matching algorithm can converge quickly even with limited overlap. This potentially reduces infection risk, as well as surgery time and potentially reduces pain during recovery. Also, blood loss is significantly reduced, relative to currently available methods, since the iterations often required by the current solutions for registration "try and fail" are eliminated and the registration process is faster after incision.

At event 2130 (FIG. 21B) the current level is $V_i$ is Instruments 900 and screws 70 are navigated using the live display (in a 3D view on display 210, for example) of the instruments/screws model overlaid on top of preoperative imaging views (3D, sagittal, transversal) of the current level $V_i$ to carry out the implantation/placement of the screws 70 in the current registered level $V_i$.

Figure 33:
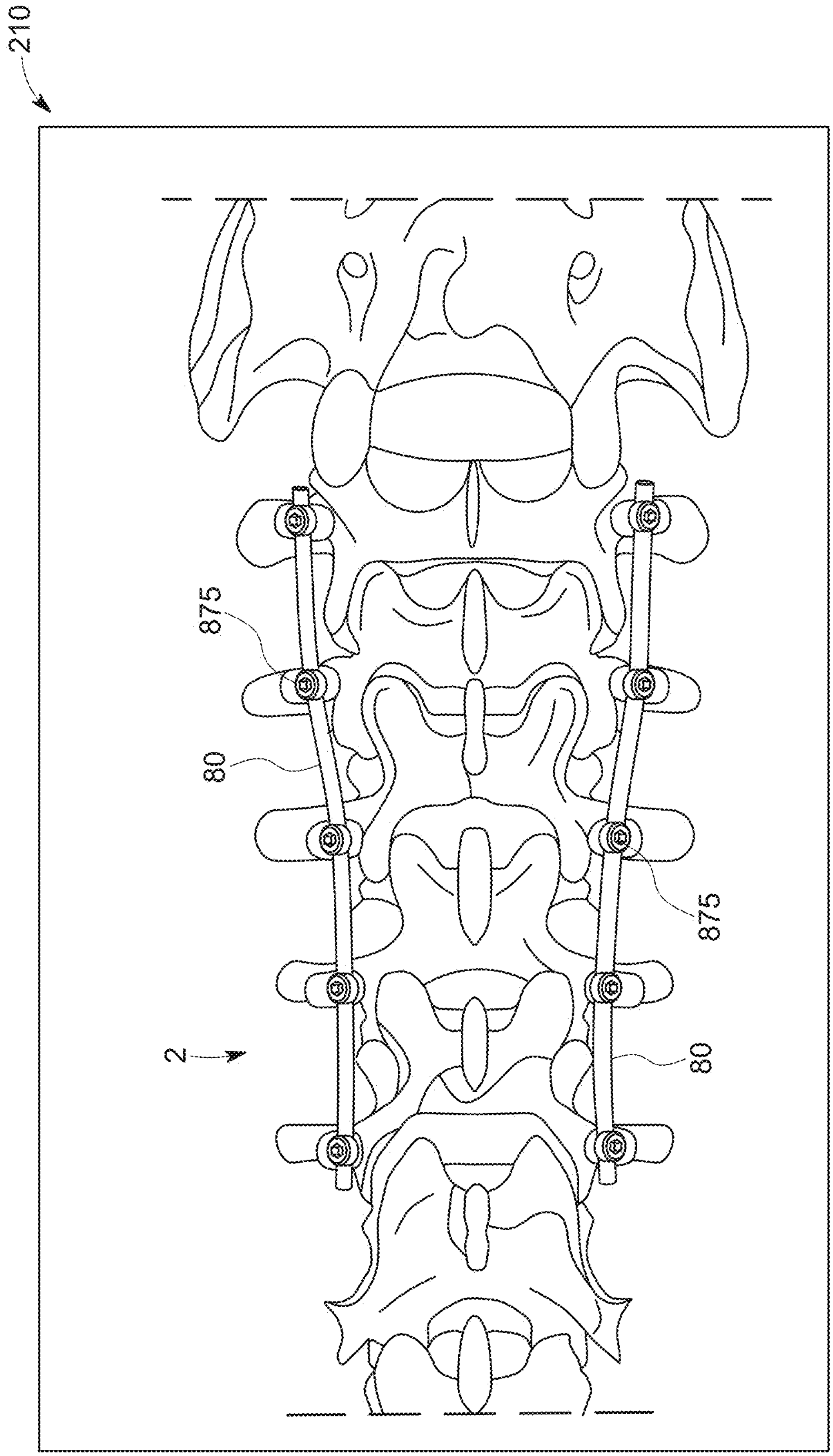
FIG. 33 illustrates rods having been installed in place and secured with set screws according to an embodiment of the present invention.

At event 2132 it is determined whether all levels that need to be operated on/instrumented, were selected/designated. If not all of the vertebrae $V_i$ that were designated to be instrumented have yet been selected, registered and instrumented, the next vertebra $V_i$ to be instrumented is designated and events 2120-2132 are iterated until all levels that need to be operated on/instrumented have been operated on/instrumented. When it is determined at event 2132 that all designated levels $V_i$ have been operated on/instrumented, then rods 80 are placed and secured with set screws 875. FIG. 33 shows the rods 80 having been installed in place and secured with set screws 875. After securement of the rods 80 as described, the patient 1 can be closed according to known standards and the surgery concludes.

Figure 22:
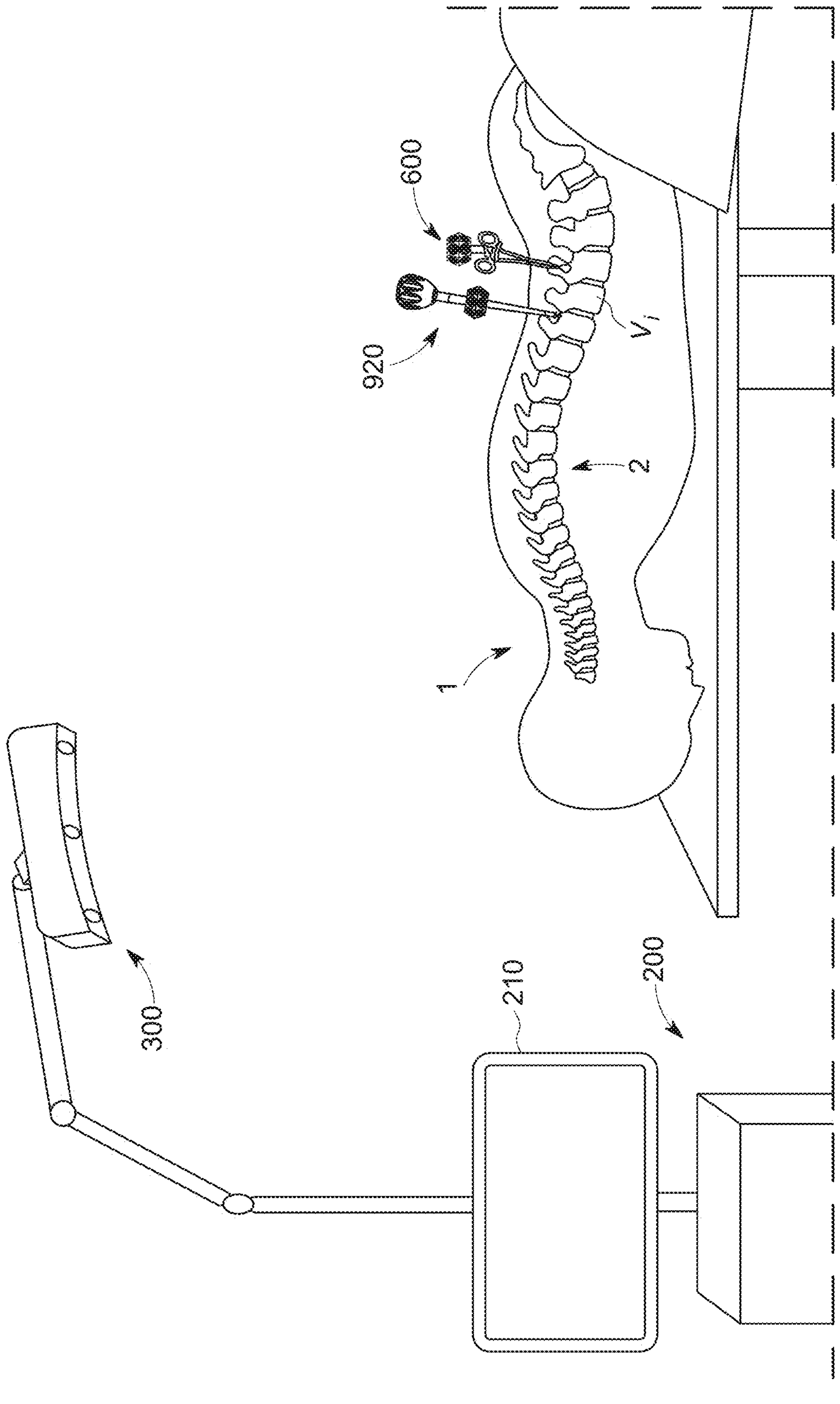
FIG. 22 illustrates a navigated probe inserted into a patient to designate a vertebra to be instrumented, according to an embodiment of the present invention.

As noted above navigated probe 920 can be used to designate the location of a vertebral level to be instrumented. FIG. 22 illustrates a navigated probe 920 inserted into patient 1 to designate a vertebra to be instrumented. Also, reference frame 600 equipped with DNM 400 has been clipped onto a spinous process of the patient 1.

Figure 23A:
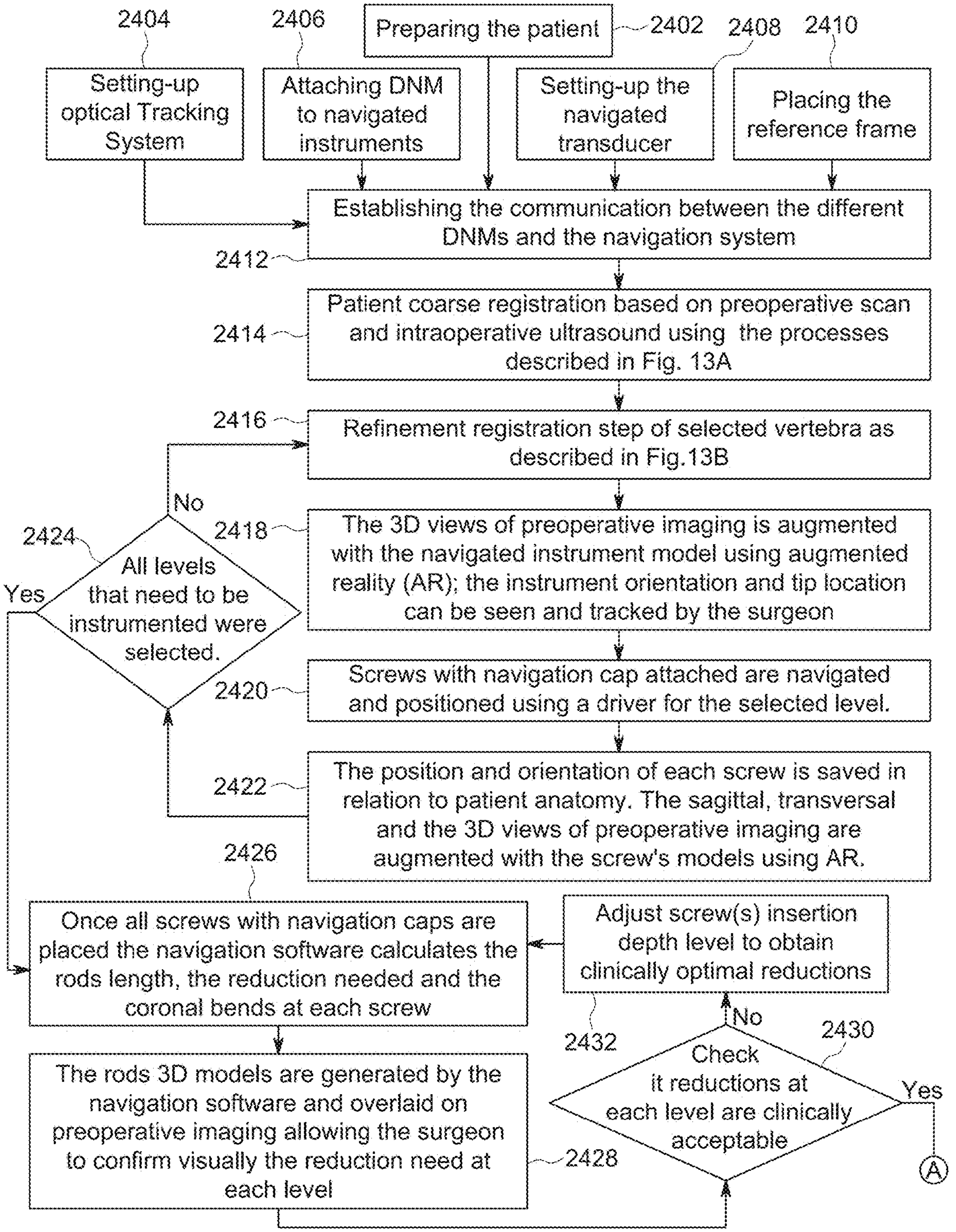
FIGS. 23A-23B show a flowchart illustrating events that may be carried out for an MIS surgical procedure on the spine, with registration and tracking based on preoperative scan imaging and intraoperative ultrasound scan imaging, according to an embodiment of the present invention.
Figure 23B:
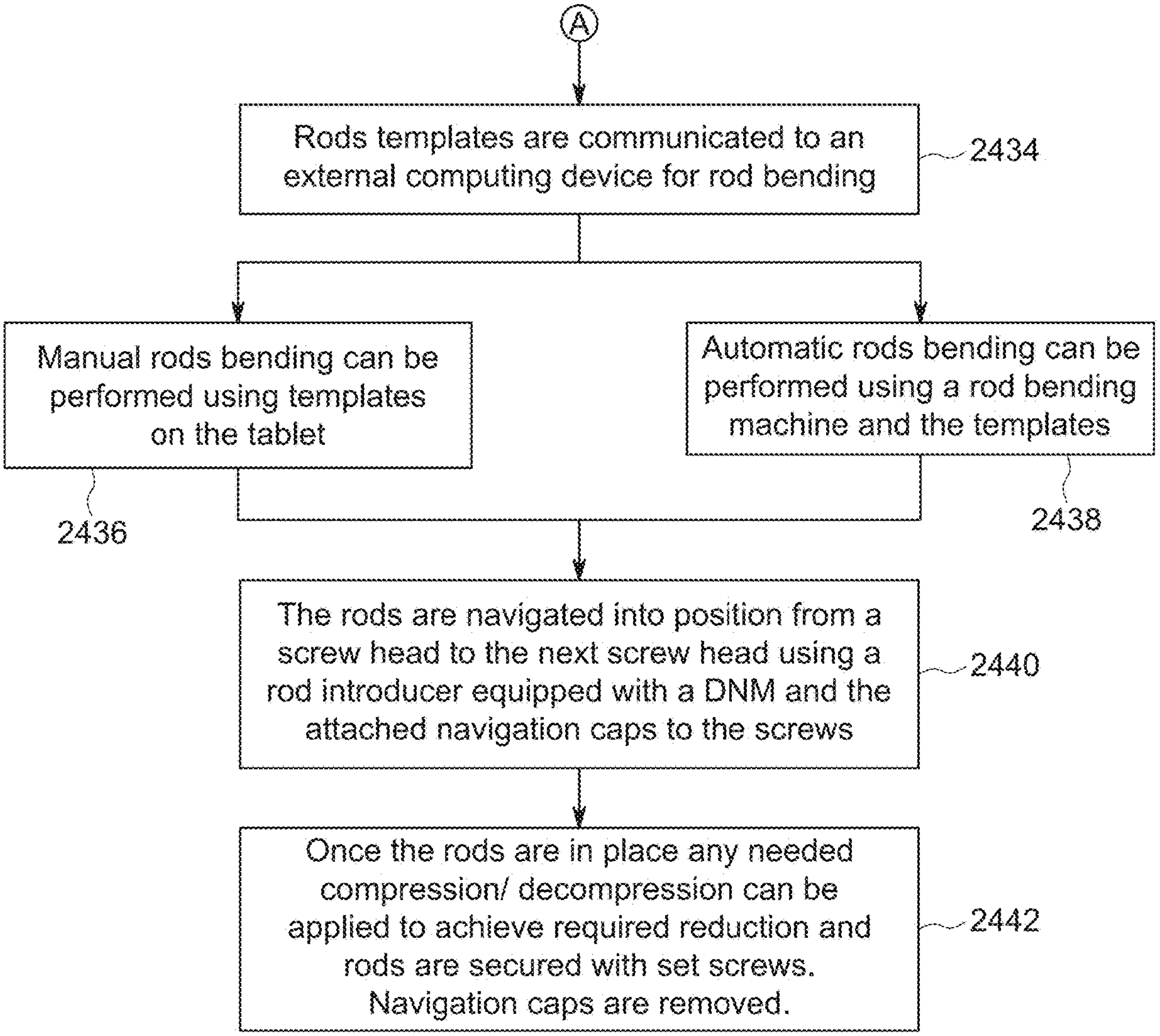
Figure 26A:
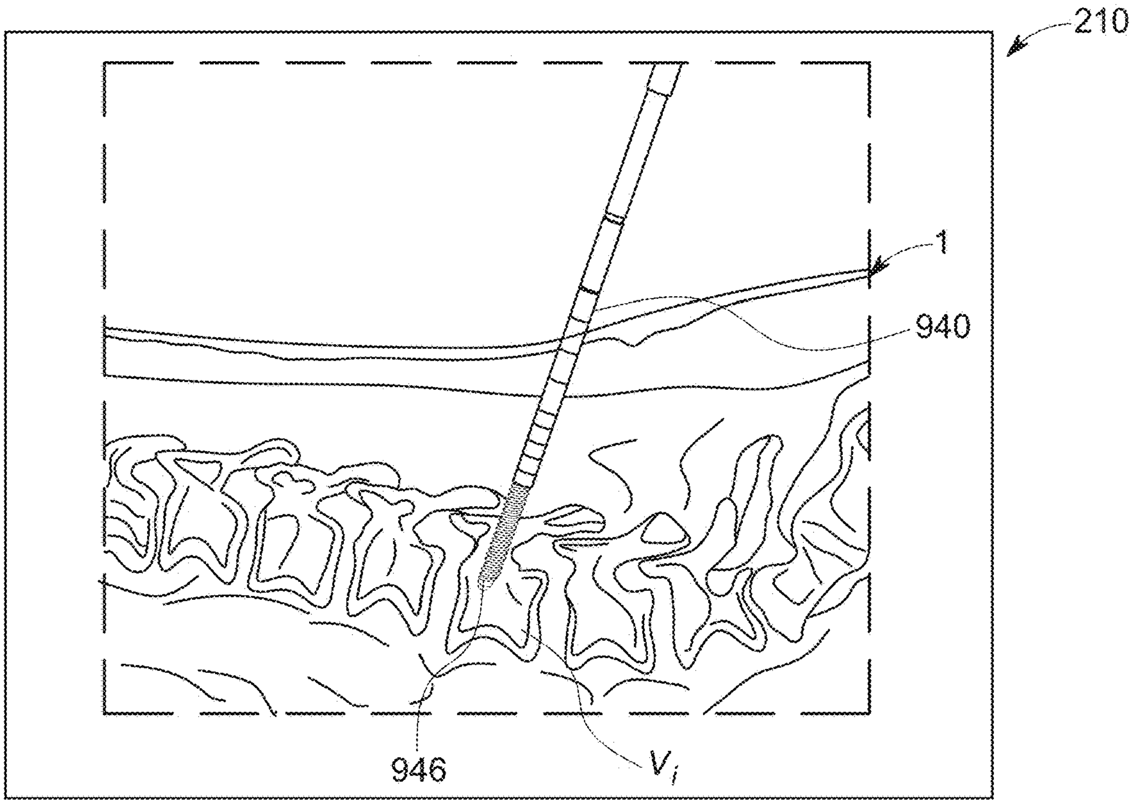
FIGS. 26A-26C show a navigated instrument overlaid on top of preoperative imaging by the computer system using augmented reality (AR), according to an embodiment of the present invention.
Figure 26B:
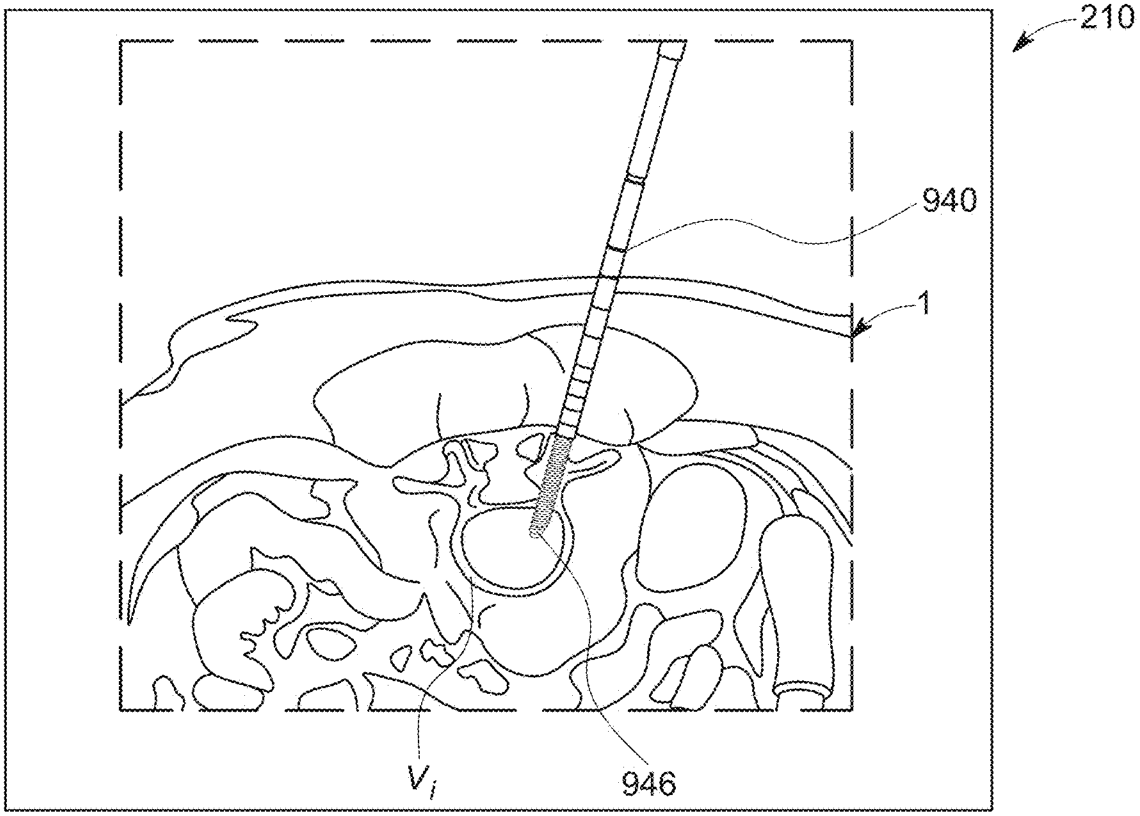
Figure 26C:
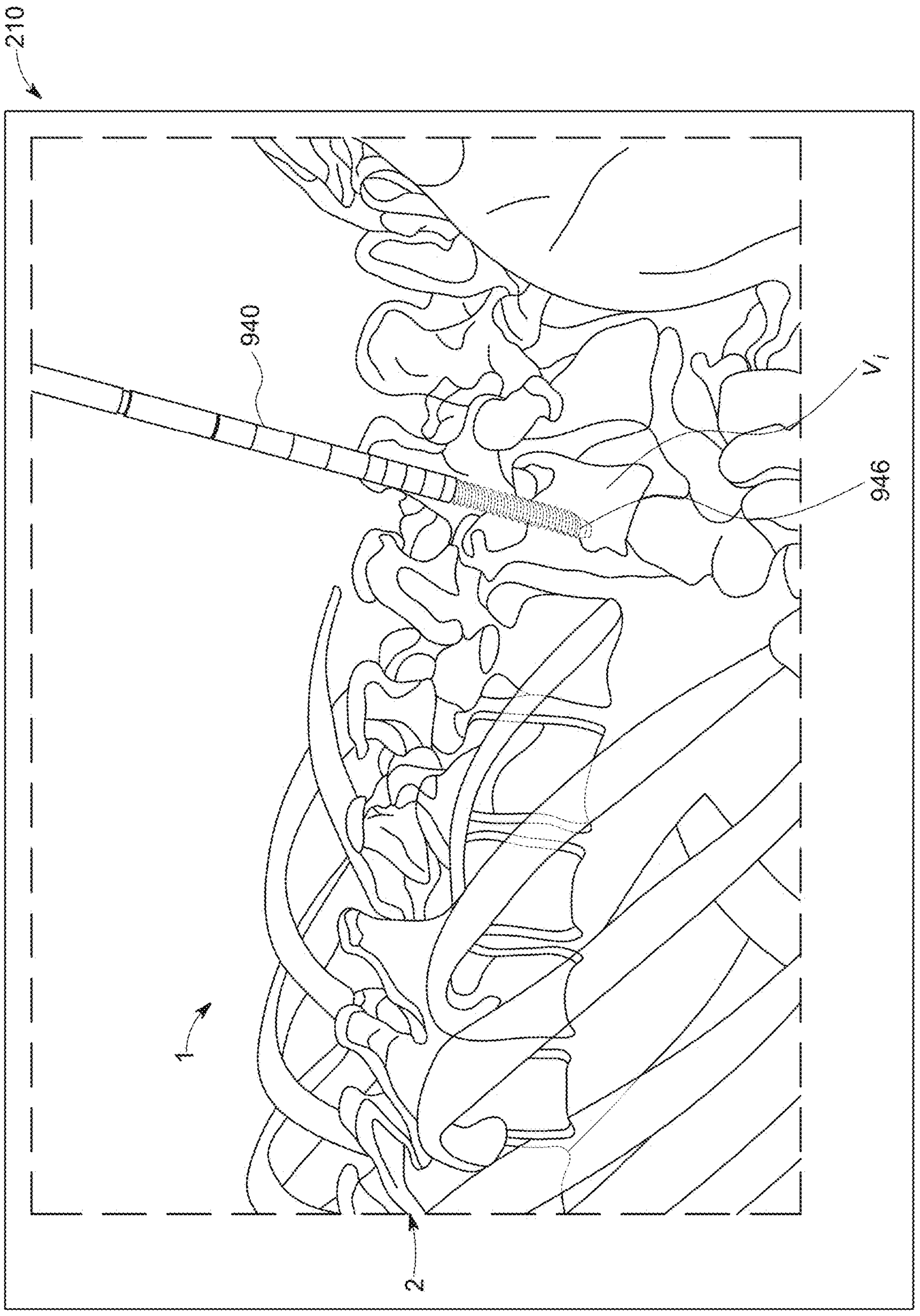
Figure 26D:
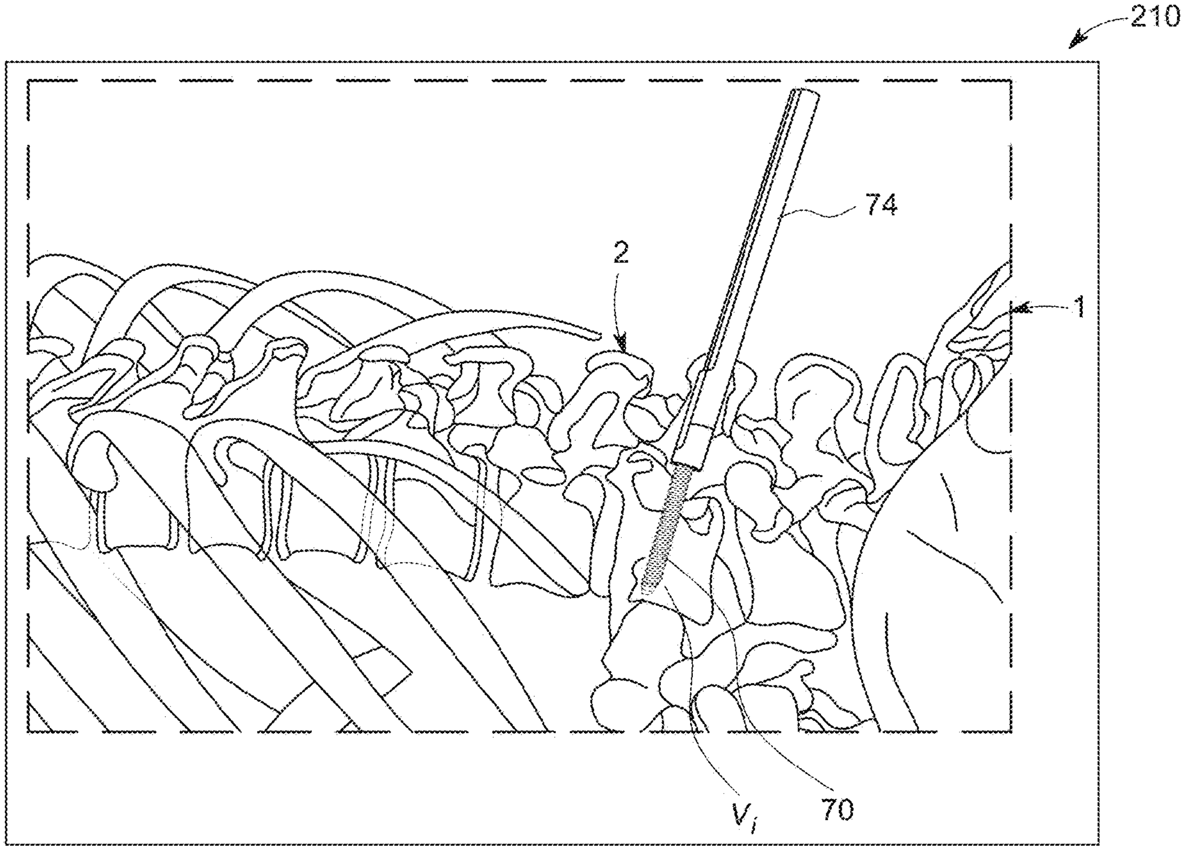
FIG. 26D shows a 3D view of a patient with a 3D rendering of the spine of the patient having been augmented with an extended screw model after the screw was implanted into vertebra $V_i$, according to an embodiment of the present invention.

FIG. 26A shows an example of an instrument 940 displayed in a view of a patient 1 on display 210. The tip 946 of instrument is shown within the vertebrae $V_i$ of the current level being addressed by the procedure. FIG. 26A is a sagittal view from the preoperative imaging augmented with the instrument model. FIG. 26B is a transversal view at $V_i$ of FIG. 26A. FIG. 26C is a 3D view of the patient 1 that represents a 3D rendering of the spine 2, augmented with the instrument 940 model. FIGS. 26A-26C represent a navigated instrument 900, which in this example, is a tap 940, overlaid on top of preoperative imaging or intraoperative imaging by the computer system 200 using augmented reality (AR). Of course, other instruments 900, or any other object that needs to be visualized during the procedure can be similarly overlaid. In FIGS. 26A-26C the model rendering of tap 940 is added by the navigation software to the imaging to allow a surgeon or other user to know that the tap 940 is being placed in the intended vertebra $V_i$ and that the orientation of the instrument 940 in relation to the anatomy/orientation of the vertebra $V_i$ is as intended, and that the placement of the tip 946 of the instrument 940 is placed at the intended depth/location. FIG. 26D shows a 3D view of a patient 1 with a 3D rendering of the spine 2 of the patient having been augmented with an extended screw model 74, 70 after the screw 70 was implanted into vertebra $V_i$, according to an embodiment of the present invention FIGS. 23A-23B show a flowchart illustrating events that may be carried out for an MIS surgical procedure on the spine, with registration and tracking based on preoperative scan imaging and intraoperative ultrasound scan imaging, according to an embodiment of the present invention. At event 2402 the patient 1 is prepared for the surgery, such as in a manner described previously with regard to event 2102. At event 2404, the camera system 300 is set up, like described previously with regard to event 2106. At event 2406 a DNM 400 is attached to at least one instrument to be navigated during the procedure. FIG. 10 shows an example of an instrument 920 having a DNM 400 attached thereto. At event 2408, a navigated transducer is set up. This set up includes establishing the communication between the computer system 200 and transducer 502 and communication between the attached DNM 400 with the computer system 200. The "navigated transducer", as used here refers to both transducer 502 and transducer 1000. Reference frame 600, including DNM 400 is fixed on a bony structure close to the levels to be operated on within the viewing field of the camera system 300 at event 2410. At event 2412 communication between the DNM's 400 to be used in the procedure and the navigation system 100, including camera system 300 and computing system 200 is established.

At event 2414 patient coarse registration based on preoperative scanning image data (CT scan preferred, but alternatives are possible) and intraoperative ultrasound scanning image data is performed. A more detailed description of this event can be found with reference to the description of FIG. 13A above.

At event 2416 patient refinement registration based on preoperative scanning image data (CT scan preferred, but alternatives are possible) and intraoperative ultrasound scanning image data is performed for a selected level. A more detailed description of this event can be found with reference to the description of FIG. 13B above.

At event 2418 a navigated instruments model is overlaid live on 3D views of preoperative imaging of one or more vertebra currently being operated on. A navigated instrument model refers to a 3D rendering of the instrument. Examples of this are shown in FIGS. 26A-26C. Using visual imaging of the markers 404 on the DNM 400 attached to the instrument being used, as well as the data provided by IMU 700 in DNM 400, the instrument tip location and orientation can be seen and tracked on the 3D preoperative view at event 2418.

Figure 24:
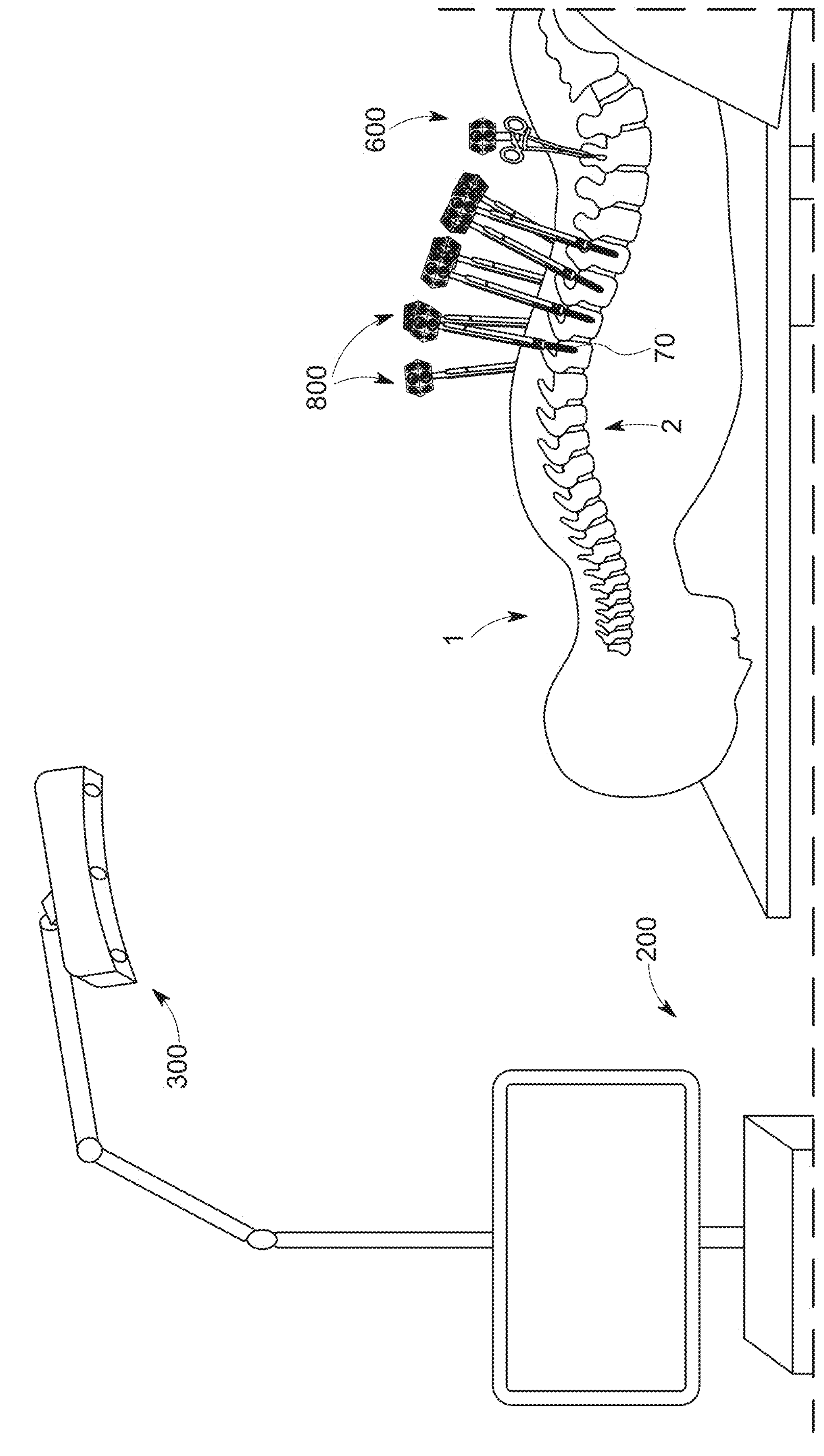
FIG. 24 illustrates navigation caps having been inserted into extended pedicle screws, according to an embodiment of the present invention.

At event 2420 the user/surgeon attaches the navigation caps 800 to pedicle screws 70 and navigates the pedicles screws, using a screw driver, into position on the selected vertebrae. FIG. 24 illustrates screws 70 with mounted navigation caps 800 having been inserted. The position and orientation of each screw 70 that has a navigation cap 800 attached to it is saved in relation to the patient anatomy and screw models are overlaid on the intraoperative 3D views provided by the optical tracking system and displayed on display 210, for example.

At event 2422, the position and orientation of each screw 70 that has a navigation cap 800 attached to it is saved in relation to the selected vertebra and screw models (used screw rendering) are overlaid on the preoperative 3D views on display 210, for example. "Used screw" refers to the characteristics (e.g., diameter and length) of a pedicle screw 72 that has been selected to be inserted in a particular location, such as by the surgeon. The characteristics of a "used screw" are provided as input to the navigation software and results in the related preloaded 3D model rendering of the used screw to be overlaid on top of the preoperative imaging.

If at event 2424 not all levels have yet been selected, processing continues to event 2416 where the next of vertebra to be instrumented is selected and a refinement registration step is completed. Events 2416-2422 are iterated until all levels to be instrumented have been registered and screws with mounted navigation caps placed, and then the procedure advances to event 2426 as noted hereafter.

Once all of the screws 70 with mounted navigation caps 800 have been inserted into the pedicles of levels to be instrumented, the computing system 200, executing the navigation software with input from the camera system 300

Figure 27:
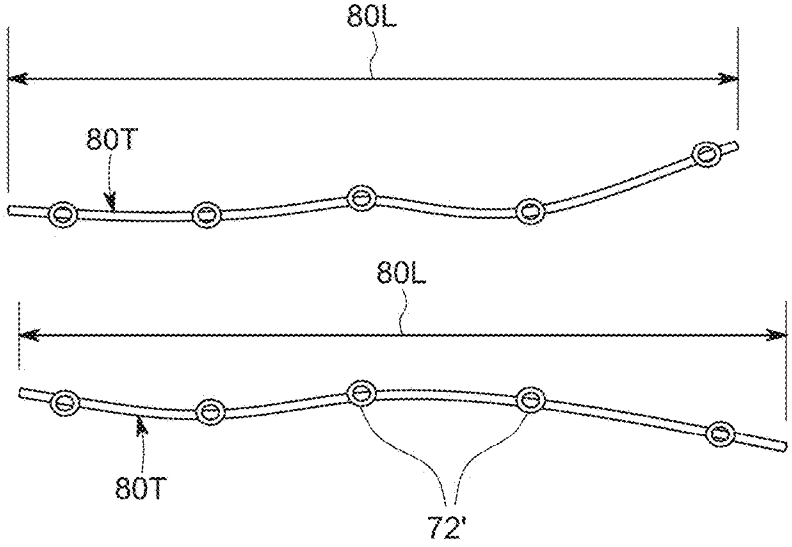
FIG. 27 illustrates rod templates 80T according to an embodiment of the present invention.

(including visual images from markers 400 and locations of the same calculated by fusing data from IMUs 700 therewith), at event 2426 calculates the rod length, and the rod bends in the coronal plane at each screw 70 location, and also the amount of reduction needed for optimal sagittal correction/alignment. The rod length 80L is calculated using the position and orientation of the screws 70 in the space of each screw 70. FIG. 27 illustrates rod templates 80T according to an embodiment of the present invention. The sagittal correction/alignment can be planned preoperatively by the surgeon using planning software (e.g. Surgimap, ASKyphoplan, etc.) to determine the optimal lordotic bend required based on the patient age, weight, sex, misalignment, etc. The sagittal alignment parameters or file are used as inputs for the navigation software in addition to the screw locations and orientations to determine the rod templates that conform to the patient 1 and preplanned corrections.

At event 2428, the rod templates that show the desired bends in rods to be implanted to carry out the preplanned amount of spinal conformation are overlaid on the different views (sagittal, antero-posterior and 3D view) of the preoperative imaging on display 210 allowing the surgeon to visually confirm if the reductions at the different levels being instrumented are within what is clinically acceptable at event 2432.

If any screw reduction is not within what is clinically acceptable (such as to avoid screw pulling out, for example), at event 2430, the surgeon can, at event 2432, introduce a screw driver through the bore 806 of the navigation cap 800 and adjust as required the insertion depth level of the screw 70 and consequently the extent of reduction at that level. Events 2426-2432 are iterated until the surgeon is satisfied that all the reduction levels are clinically acceptable.

Once all the reduction levels are clinically acceptable, at event 2434, the one or more rod templates can be communicated to an external device such as an external computing device like a tablet, laptop, desktop, smartphone, or other computing device equipped to receive data characterizing the rod templates. The rod template data in the external device can then be used to either manually bend one or more rods according to the specifications of the rod template(s) (event 2436) or can be inputted to a rod bending machine (event 2438) that can use the template data to automatically bend one or more rods to meet the specifications of the rod template(s). Alternatively rod template data can be inputted directly at event 2438 to an automatic rod bending machine where the external computing device is contained in the automatic rod bending machine.

Figure 28B:
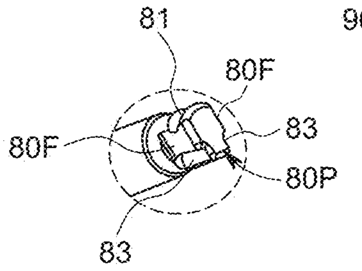
FIG. 28B is an enlarged, detailed view of the proximal end of the rod shown in circle 28BC of FIG. 28A.
Figure 28D:
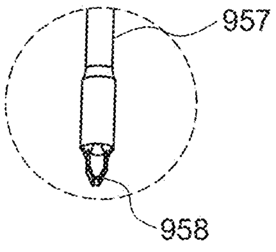
FIG. 28D is another enlarged, detailed view of the distal end portion of the rod introducer of FIG. 28A.
Figure 28C:
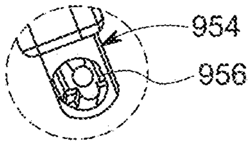
FIG. 28C is an enlarged, detailed view of the distal end portion of the rod introducer shown in circle 28BC of FIG. 28A.
Figure 28A:
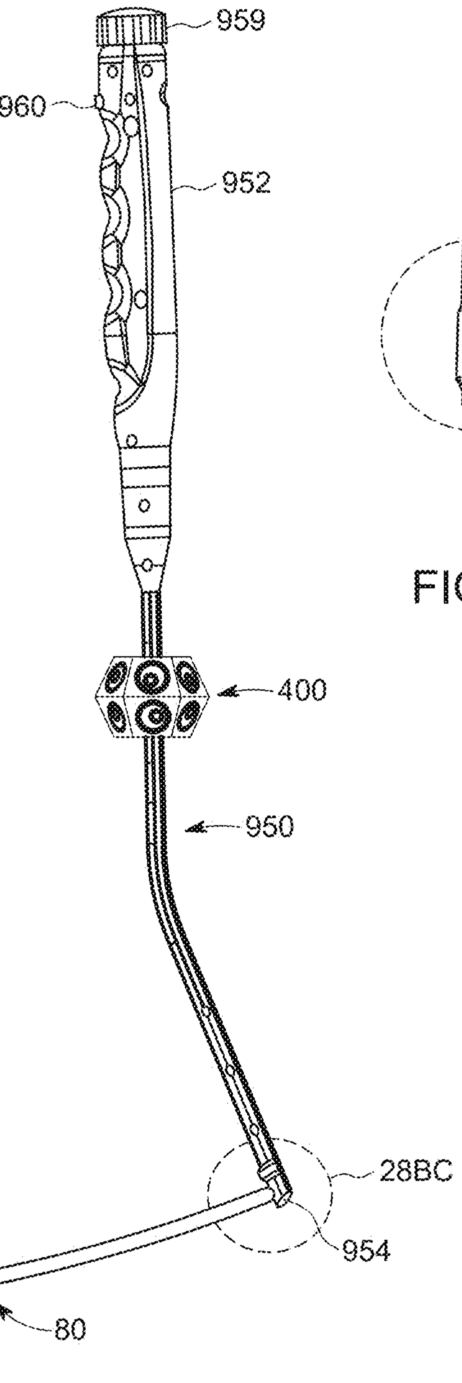
FIG. 28A shows a rod introducer instrument attached to a rod, according to an embodiment of the present invention.

At event 2440, for each bent rod 80, the surgeon attaches the rod 80 to a rod introducer 950 equipped with a DNM 400, see FIG. 28A. The surgeon can grasp the handle 952 of the rod introducer 950 and advance/manipulate the positioning of the rod, including distal end 80D, by manipulating and advancing the rod introducer 950 via handle 952. Since the connection between the rod introducer 950 and the rod 80 is at a fixed position at the flat end (proximal end) 80P (see FIG. 28B) of the rod 80, and since the connection is a rigid connection, the rod 80 can be navigated. The distal end portion 954 of the rod introducer 952 includes a mating feature 956 (see FIG. 28C), which, in the embodiment of FIG. 28A is a female receptacle with a matching perimeter and surfaces that fit with the perimeter and surfaces of the proximal end portion 80P of rod 80. The proximal end portion (see FIG. 28B) includes flat surfaces 80F which abut with matching flat surfaces inside the opening of mating feature 956. Grooves 83 are provided to mate with matching protruding features inside the opening of mating feature 956. Groove 81 is provided to mate with a sliding matching mechanism in the opening of the mating feature 956 that is actuatable to lock proximal end portion 80P in mating feature 956 of distal end portion 954, thereby forming a rigid connection between the rod 80 and rod introducer 950. FIG. 28D shows the distal end 958 of the sliding shaft 957 inside the rod introducer 950 with matching geometry features to the groove 81 on the rod 80. Rotation of knob 959 clockwise drives the shaft 957 to slide slides downward toward the rod 80 until the end 958 is completely inside the groove 81. Button 960 is then actuated to lock the rotation mechanism of knob 959 to prevent the shaft 957 from budging, thereby rigidly locking the rod 80 to the rod introducer 950. It is noted that the present invention is not limited to this arrangement as many other types of mating features could be substituted, that still perform the needed functions of maintaining the orientation and position of the rod 80 fixed relative to the rod introducer 950.

Figure 29:
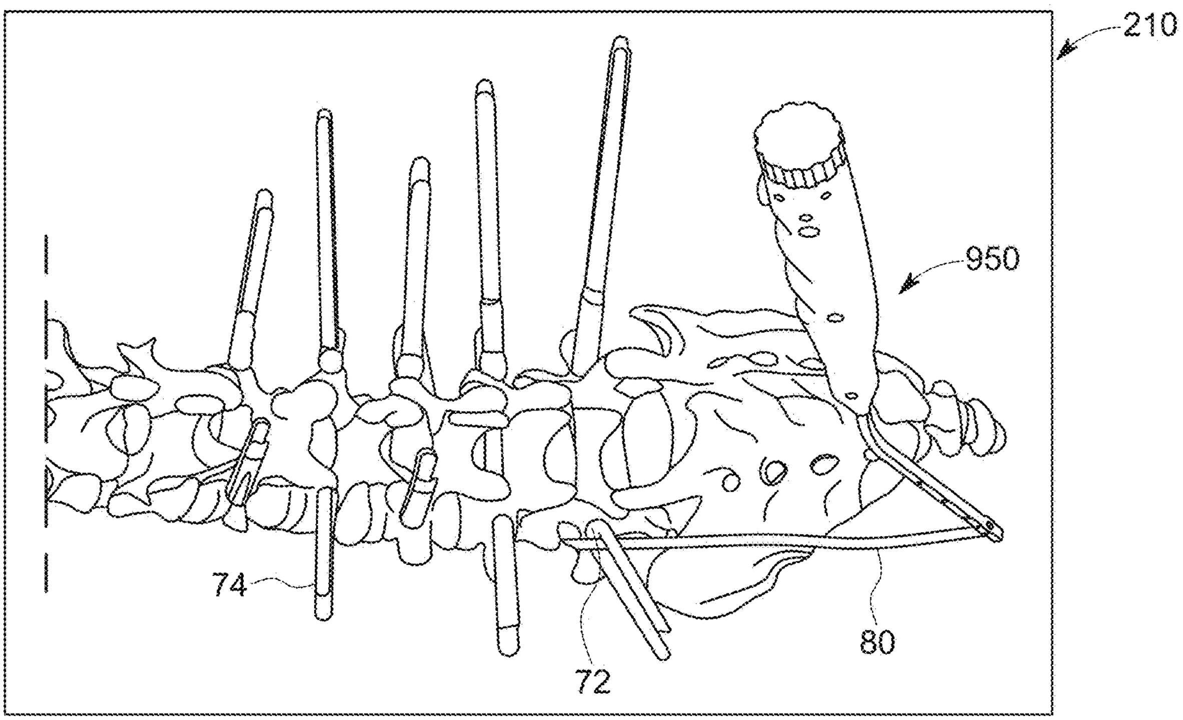
FIG. 29 illustrates the display of a rod navigation from a screw head to the next screw head a from caudal to cranial direction using a rod introducer, according to an embodiment of the present invention.
Figure 30:
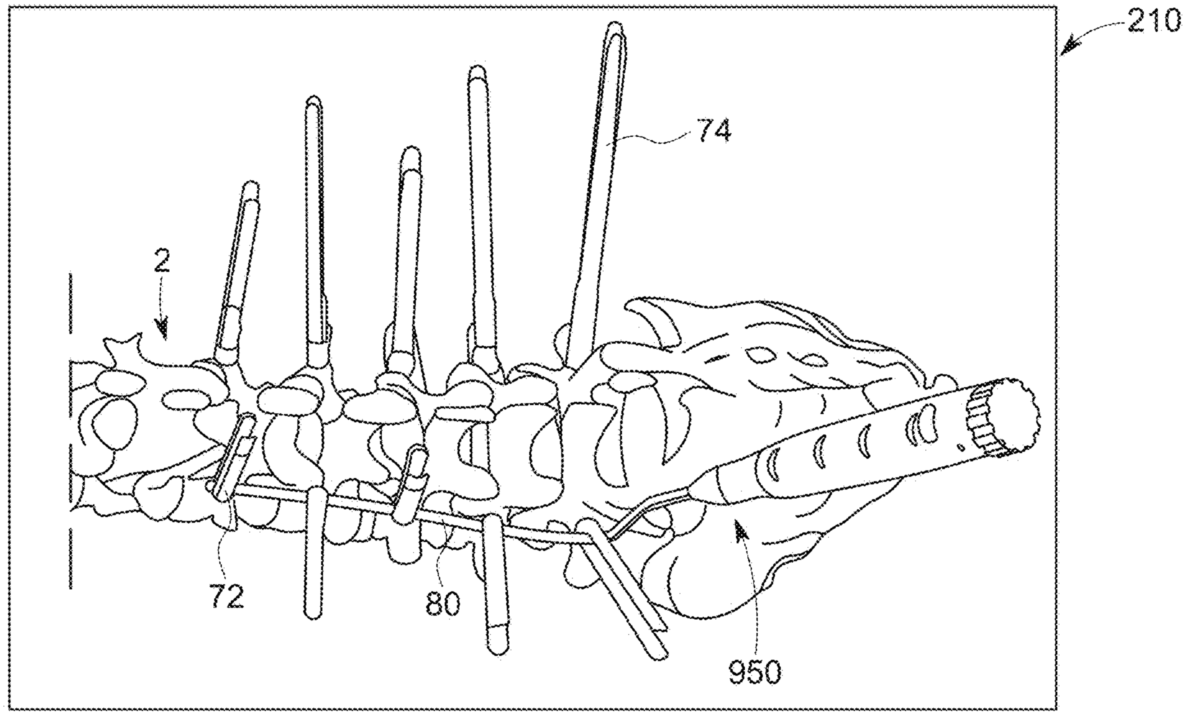
FIG. 30 illustrates the display of a rod navigated to the last cranially positioned screw according to an embodiment of the present invention.

FIG. 29 and FIG. 30 illustrate the system display 210 as the surgeon is introducing the rod 80 percutaneously. The insertion of the rod is navigated using the live display of overlaid models, on the preoperative imaging views, of the rod 80, rod introducer 950, and the screws tulips 72 and tabs 74 tracked by navigation caps 800 (navigation caps not shown in FIGS. 29-30). The navigation caps 800 facilitate the tracking of the orientation of the pedicle screws tabs 74 and/or the screws tulip 72, as the screw head can move around the screw shaft 76, the navigation software updates the orientation of overlaid model of screws heads, as they can be adjusted by the surgeon, while the rod is introduced, facilitating the insertion of the rod percutaneously. It is noted that, although models of the navigation caps 800 could be overlaid on the displays in FIGS. 29 and 30, they are typically not displayed, as there is no value in displaying them to the surgeon, as they can be more of a distraction and do not need to be visualized. The advancement of the rod 80 using the rod introducer 950 is shown in a live manner, via the advancement of the rod model. FIGS. 29 and 30 are excerpted views showing the beginning of the insertion (FIG. 29) and the fully inserted rod (FIG. 30), but positions therebetween are continuously displayed on 210 so that the surgeon can view the insertion in real time. The preoperative imaging is augmented with the 3D model rendering of the rod 80 and rod introducer 950, generated by the navigation software, in different views, as the surgeon is advancing the rod 80 from screw head 72 to consecutive screw head 72, from a caudal to cranial direction in the embodiment shown in FIGS. 29-30. However, insertion can alternatively be carried out from a cranial to caudal direction in another embodiment. Either way the visualization allows the surgeon to place the rods 80 in a safer and a faster manner than possible without navigation. The use of the DNM 400 to navigate the rod introducer 950 and rods 80 is possible since the DNM-based tracking continues uninterrupted even when the rod introducer 950 is held by the surgeon in orientations that would not be possible to track with the current tracking art (optical tracking). Navigating rods 80, in addition to saving time, can reduce muscle-tearing/weakening and thus can positively impact the healing process.

Figure 31:
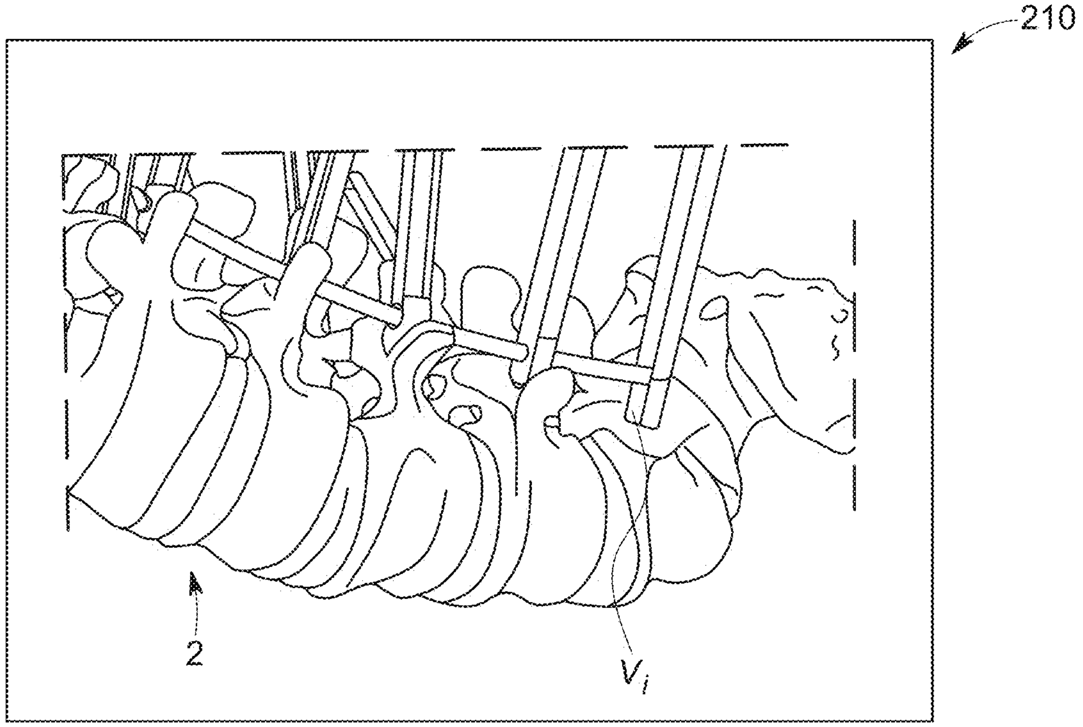
FIG. 31 illustrates the display of a rod placed and the reduction needed, at vertebral level Vi to conform to the desired correction in the sagittal plane according to an embodiment of the present invention.
Figure 32:
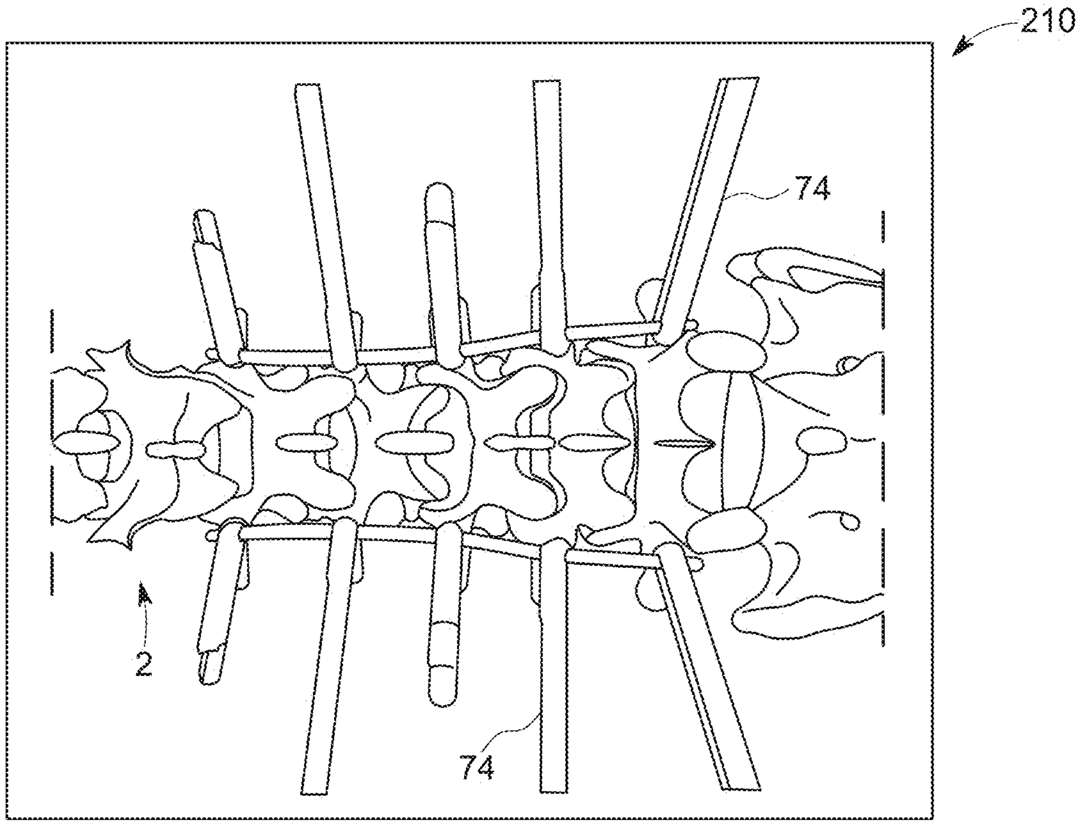
FIG. 32 illustrates the display of rods placed into position and secured with set screws after reduction is applied according to an embodiment of the present invention.

At event 2442, once a rod is passed through the last cranially (or caudally, depending upon the direction of advancement) positioned screw head 72, if reduction is needed, compression and/or distraction can be applied. FIG. 31 shows reduction needed at the last vertebra caudally in order to apply the desired correction in the sagittal plane. Once any needed compression and/or distraction has been completed, the rods 80 can be secured in place with set screws 875 using a screw driver 1200 through the bore 806 of the navigation caps 800. FIG. 32 illustrates extended tabs 74 through which set screws 875 can be delivered to the screw heads 72 to be threadedly engaged therewith. FIG. 33 illustrate the rods 80 having been installed in place and secured with set screws 875. When the securement by placement of the set screws has been completed, the navigation caps are removed and the tabs are removed, leaving the rods installed in place as shown in FIG. 33.

While the present invention has been described with reference to the specific embodiments thereof, it should be understood by those skilled in the art that various changes may be made and equivalents may be substituted without departing from the scope of the invention. In addition, many modifications may be made to adapt a particular situation, material, composition of matter, process, process step or steps, to the objective and scope of the present invention. All such modifications are intended to be within the scope of the claims appended hereto.

That which is claimed is:

1. A method of tracking and registration for a spine surgery; said method comprising:

providing volumetric image data obtained from a preoperative scan of at least a portion of a spine including preselected vertebrae of the spine;

processing the volumetric image data, including extracting surface data characterizing bone surfaces of the preselected vertebrae;

extracting partial surface data that can be captured by ultrasound from the extracted surface data characterizing bone surfaces of the preselected vertebrae;

sweeping, from locations external of a body in which the spine is located, at least the preselected vertebrae and processing data obtained therefrom to provide ultrasound volumetric image data;

correlating the ultrasound volumetric image data and the extracted partial surface data and identifying ultrasound surface data characterizing the bone surfaces of the preselected vertebrae that correspond to the surface data extracted from the volumetric image data from the preoperative scan and coarsely registering the identified ultrasound surface data with the surface data extracted from the volumetric image data for each vertebra of the preselected vertebrae by calculating rotation matrices and translation vectors that transform the surface data extracted from the volumetric image data to correlate with the ultrasound surface data;

making a least one incision to provide access to the preselected vertebrae;

obtaining post-incision image data for each of said preselected vertebrae;

for each of said preselected vertebrae, performing a registration refinement comprising processing said post-incision image data obtained after incision, calculating refinement of said rotation matrices and translation vectors, based on said post-incision image data obtained;

applying said rotation matrices and translation vectors and generating and displaying at least one model of an instrument, screw or device overlaid on an image generated from said volumetric image data obtained from said preoperative scan.

2. The method of claim 1, wherein said sweeping from locations external of the body is performed using an ultrasound probe tracked at least in part by using a directional navigation module integral therewith or attached thereto.

3. The method of claim 1, wherein ultrasound sweep acceptance criteria is checked as said sweeping is performed and size, coverage, and percentage of bright points of the ultrasound volumetric image data are calculated.

4. The method of claim 1, wherein said sweeping is performed manually.

5. The method of claim 1, wherein said sweeping is performed by a robotic arm.

6. The method of claim 1, wherein said registration refinement comprises:

inserting an ultrasound probe through one or more incisions on left and right sides of the preselected vertebrae to capture local ultrasound volumetric image data;

tracking said ultrasound probe during said capture process;

extracting local surface data characterizing bone surfaces corresponding to the bone surfaces of the local ultrasound volumetric data from said volumetric image data; and for each of said preselected vertebrae, refining said registering of said ultrasound surface data with said surface data by calculating refinement of said rotation matrices and translation vectors, based on said local surface data extracted;

wherein image resolution of said local ultrasound volumetric image data is higher than image resolution of said ultrasound volumetric image data.

7. The method of claim 6, wherein the spine surgery is an MIS surgical procedure.

8. The method of claim 1, wherein said registration refinement comprises:

obtaining said post-incision image data by imaging exposed bony structures of the preselected vertebrae via a camera system; and wherein said registration refinement comprises matching a 3D surface of said post-incision imaging data of exposed bony structures to said surface data characterizing bone surfaces of the preselected vertebrae extracted from said volumetric image data.

9. The method of claim 8, wherein, for each of said preselected vertebrae, said post-incision image data comprises a 3D point cloud.

10. The method of claim 8, wherein the spine surgery is an open surgical procedure.

11. The method of claim 8, wherein the volumetric image data obtained from the preoperative scan is provided from a CT preoperative scan.

12. The method of claim 8, wherein said applying said refinement rotation matrices and refinement translation vectors and generating and displaying comprises displaying a 3D image of at least the preselected vertebrae, said method further comprising:

installing navigation caps having directional navigation modules on pedicle screws;

for each of the pedicle screws, inserting a screw driving instrument through a bore of the navigation cap installed on the pedicle screw, and driving the pedicle screw into one of the preselected vertebrae;

calculating positions and orientations of the pedicle screws installed in the preselected vertebrae, based on inputs received from image data of the navigation caps and data received from the directional navigation modules, respectively;

calculating a rod length, rod bends in a coronal plan at each location of each of the pedicle screws and reduction needed at each of the pedicle screws, based on the calculated positions and orientations of the pedicle screws to create a rod bending template; and outputting the rod bending template for use in making a custom bent rod.

13. The method of claim 12, further comprising:

overlaying a model of a rod bent according to specifications of the rod bending template, a rod inserter and the pedicle screws on an image of the selected vertebrae generated from said volumetric image data obtained from said preoperative scan; and advancing the rod while tracking advancement of the rod by the rod inserter through heads of the pedicle screws via the overlaid models of pedicle screws and the rod.

14. The method of claim 13, comprising confirming, by view on the display, whether reductions to be accomplished at each of the pedicle screws are within predefined acceptance levels, and when one or more of the reductions is not within the predefined acceptance level, for each of the pedicle screws where reduction is not within the predefined acceptance level, introducing a screw driver through the bore of the navigation cap, adjusting the pedicle screw insertion level, viewing the screw having been adjusted and the resultant reduction having been achieved, and repeating said adjusting and viewing as needed, until reductions accomplished by each of the pedicle screws are within said predefined acceptance levels.

15. The method of claim 12, further comprising manually bending a rod according to specifications of the rod bending template having been outputted.

16. A rod bent by the method of claim 15.

17. The method of claim 12, wherein the rod bending template is outputted to a rod bending machine, and said method further comprises automatically bending a rod according to specifications of the rod bending template.

18. A rod bent by the method of claim 17.

* * * * *